United States Patent
Beardsley et al.

(10) Patent No.: US 12,156,863 B2
(45) Date of Patent: *Dec. 3, 2024

(54) COMBINATION CANCER THERAPY WITH PENTAAZA MACROCYCLIC RING COMPLEX AND ASCORBATE COMPOUND

(71) Applicant: Galera Labs, LLC, Creve Coeur, MO (US)

(72) Inventors: Robert A. Beardsley, University City, MO (US); Dennis P. Riley, Chesterfield, MO (US); Douglas R. Spitz, Jr., Iowa City, IA (US); Collin Heer, Coralville, IA (US); Melissa Fath, Iowa City, IA (US)

(73) Assignee: Galera Labs, LLC, Malvern, PA (US)

( * ) Notice: Subject to any disclaimer, the term of this patent is extended or adjusted under 35 U.S.C. 154(b) by 79 days.

This patent is subject to a terminal disclaimer.

(21) Appl. No.: 17/538,790

(22) Filed: Nov. 30, 2021

(65) Prior Publication Data

US 2022/0304977 A1 Sep. 29, 2022

Related U.S. Application Data

(63) Continuation of application No. 16/329,900, filed as application No. PCT/US2017/049960 on Sep. 1, 2017, now Pat. No. 11,219,614.

(60) Provisional application No. 62/382,667, filed on Sep. 1, 2016.

(51) Int. Cl.
| | |
|---|---|
| *A61K 31/375* | (2006.01) |
| *A61K 31/198* | (2006.01) |
| *A61K 31/555* | (2006.01) |
| *A61K 31/635* | (2006.01) |
| *A61K 31/7135* | (2006.01) |
| *A61K 33/242* | (2019.01) |
| *A61K 33/32* | (2006.01) |
| *A61K 45/06* | (2006.01) |
| *A61P 35/00* | (2006.01) |

(52) U.S. Cl.
CPC .......... *A61K 31/375* (2013.01); *A61K 31/198* (2013.01); *A61K 31/555* (2013.01); *A61K 31/635* (2013.01); *A61K 31/7135* (2013.01); *A61K 33/242* (2019.01); *A61K 33/32* (2013.01); *A61K 45/06* (2013.01); *A61P 35/00* (2018.01)

(58) Field of Classification Search
CPC .................................................. A61K 31/375
See application file for complete search history.

(56) References Cited

U.S. PATENT DOCUMENTS

| | | |
|---|---|---|
| 3,930,867 A | 1/1976 | Bigelow |
| 4,001,212 A | 1/1977 | Richman |
| 4,702,998 A | 10/1987 | Tanaka et al. |
| 5,096,724 A | 3/1992 | Zenner et al. |
| 5,610,293 A | 3/1997 | Riley et al. |
| 5,637,578 A | 6/1997 | Riley et al. |
| 5,874,421 A | 2/1999 | Riley et al. |
| 5,976,498 A | 11/1999 | Newumann et al. |
| 6,040,330 A | 3/2000 | Hausheer et al. |
| 6,084,093 A | 7/2000 | Riley et al. |
| 6,177,419 B1 | 1/2001 | Campbell et al. |
| 6,180,620 B1 | 1/2001 | Salvemini |
| 6,204,259 B1 | 3/2001 | Riley et al. |
| 6,214,817 B1 | 4/2001 | Riley et al. |
| 6,245,758 B1 | 6/2001 | Stern et al. |
| 6,395,725 B1 | 5/2002 | Salvemini |
| 6,525,041 B1 | 2/2003 | Neumann et al. |

(Continued)

FOREIGN PATENT DOCUMENTS

| | | |
|---|---|---|
| CN | 1215919 | 5/1999 |
| CN | 2870352 | 2/2007 |

(Continued)

OTHER PUBLICATIONS

Du et al., Glutathione and glutaredoxin act as a backup of human thioredoxin reductase 1 to reduce thioredoxin 1 preventing cell death by aurothioglucose, J. Biol Chem, 287(45), 38210-38219 2012.

(Continued)

*Primary Examiner* — Rei Tsang Shiao

(74) *Attorney, Agent, or Firm* — Bryan Cave Leighton Paisner LLP

(57) ABSTRACT

A method of treating cancer in a subject includes administering an active agent selected from ascorbic acid, an ascorbic acid derivative, and/or a pharmaceutically acceptable salt thereof and administering a pentaaza macrocyclic ring complex corresponding to formula (I) below:

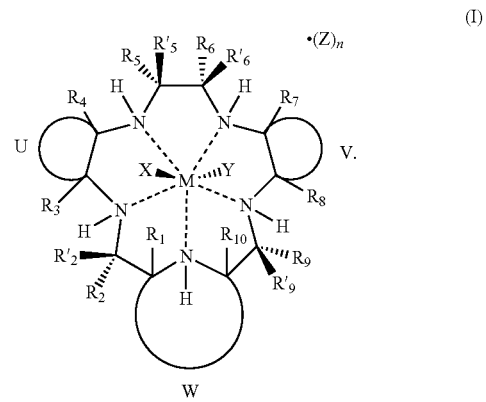

32 Claims, 6 Drawing Sheets

(56) References Cited

U.S. PATENT DOCUMENTS

| | | |
|---|---|---|
| 6,552,040 B1 | 4/2003 | Bernstein |
| 6,781,231 B2 | 8/2004 | Minervini |
| 6,916,799 B2 | 7/2005 | Fridovich et al. |
| 7,102,214 B1 | 9/2006 | Miks et al. |
| 7,166,910 B2 | 1/2007 | Minervini |
| 7,242,089 B2 | 7/2007 | Minervini |
| 7,407,645 B2 | 8/2008 | Neumann et al. |
| 7,445,641 B1 | 11/2008 | Ornberg et al. |
| 7,981,421 B2 | 7/2011 | Zhou et al. |
| 8,263,568 B2 | 9/2012 | Slomczynska et al. |
| 8,444,856 B2 | 5/2013 | Slomczynska et al. |
| 8,808,545 B2 | 8/2014 | Slomczynska et al. |
| 9,149,483 B2 | 10/2015 | Keene et al. |
| 9,198,893 B2 | 12/2015 | Keene et al. |
| 9,642,861 B2 | 5/2017 | Rothstein et al. |
| 9,738,669 B2 | 8/2017 | Keene et al. |
| 9,738,670 B2 | 8/2017 | Keene et al. |
| 9,855,279 B2 | 1/2018 | Rothstein et al. |
| 10,137,133 B2 | 11/2018 | Keene et al. |
| 10,493,081 B2 | 12/2019 | Keene et al. |
| 10,597,415 B2 | 3/2020 | Keene et al. |
| 10,610,533 B2 | 4/2020 | Rothstein et al. |
| 11,066,433 B2 | 4/2021 | Keene et al. |
| 11,219,614 B2 * | 1/2022 | Beardsley ............ A61K 31/198 |
| 11,246,950 B2 | 2/2022 | Beardsley et al. |
| 11,612,608 B2 | 3/2023 | Rothstein et al. |
| 2002/0072512 A1 | 6/2002 | Salvemini |
| 2002/0128248 A1 | 9/2002 | Salvemini |
| 2003/0050297 A1 | 3/2003 | Crapo |
| 2004/0132706 A1 | 7/2004 | Salvemini |
| 2004/0219138 A1 | 11/2004 | Salvemini |
| 2005/0101581 A1 | 5/2005 | Reading et al. |
| 2005/0171198 A1 | 8/2005 | Salvemini |
| 2005/0175580 A1 | 8/2005 | Salvemini |
| 2005/0222250 A1 | 10/2005 | Rezvani |
| 2006/0081994 A1 | 4/2006 | Craig et al. |
| 2006/0089710 A1 | 4/2006 | Ornberg et al. |
| 2006/0140953 A1 | 6/2006 | Newell et al. |
| 2006/0199792 A1 | 9/2006 | Groves et al. |
| 2006/0223808 A1 | 10/2006 | Chackalamannil et al. |
| 2007/0148154 A1 | 6/2007 | Weill et al. |
| 2008/0161324 A1 | 7/2008 | Johansen et al. |
| 2008/0166000 A1 | 7/2008 | Hsiao |
| 2008/0269185 A1 | 10/2008 | Rothstein et al. |
| 2008/0318917 A1 | 12/2008 | Salvemini et al. |
| 2009/0131377 A1 | 5/2009 | Salvemini |
| 2009/0221622 A1 | 9/2009 | Teja et al. |
| 2009/0257979 A1 | 10/2009 | Beigelman et al. |
| 2010/0304415 A1 | 12/2010 | Slomczynska et al. |
| 2011/0136756 A1 | 6/2011 | Keene et al. |
| 2013/0079317 A1 | 3/2013 | Keene et al. |
| 2014/0142065 A1 | 5/2014 | Che et al. |
| 2017/0044193 A1 | 2/2017 | Keene et al. |
| 2018/0237462 A1 | 8/2018 | Keene et al. |
| 2019/0151331 A1 | 5/2019 | Beardsley et al. |
| 2019/0209524 A1 | 7/2019 | Beardsley et al. |
| 2019/0350867 A1 | 11/2019 | Hahn |
| 2020/0000793 A1 | 1/2020 | Falo, Jr. et al. |
| 2020/0215077 A1 | 7/2020 | Rothstein et al. |
| 2020/0376148 A1 | 12/2020 | Beardsley et al. |
| 2021/0338686 A1 | 11/2021 | Keene et al. |
| 2021/0347796 A1 | 11/2021 | Keene et al. |
| 2021/0361701 A1 | 11/2021 | Keene et al. |
| 2022/0088030 A1 | 3/2022 | Keene et al. |
| 2022/0118119 A1 | 4/2022 | Beardsley et al. |

FOREIGN PATENT DOCUMENTS

| | | |
|---|---|---|
| CN | 103906756 | 7/2014 |
| EA | 010834 | 12/2008 |
| EP | 0524161 | 1/1993 |
| EP | 0598753 | 3/1998 |
| EP | 2760874 | 8/2014 |
| EP | 3388082 | 10/2018 |
| JP | H06509566 | 10/1994 |
| JP | 1996040941 | 2/1996 |
| JP | 2002506445 | 2/2002 |
| JP | 2002534382 | 10/2002 |
| JP | 2003509423 | 3/2003 |
| JP | 2004507487 | 3/2004 |
| JP | 2004517113 | 6/2004 |
| JP | 2011513333 | 4/2011 |
| JP | 2011516610 | 5/2011 |
| JP | 2014526562 | 10/2014 |
| RU | 2313368 | 9/2011 |
| WO | 1991010645 | 7/1991 |
| WO | 1993002090 | 2/1993 |
| WO | 1994015925 | 7/1994 |
| WO | 95028968 | 11/1995 |
| WO | 1996039396 | 12/1996 |
| WO | 97006830 | 2/1997 |
| WO | 98058636 | 12/1998 |
| WO | 00072893 | 12/2000 |
| WO | 01019823 | 3/2001 |
| WO | 200158458 | 8/2001 |
| WO | 2002053142 | 7/2002 |
| WO | 2002058686 | 8/2002 |
| WO | 2002071054 | 9/2002 |
| WO | 2002100395 | 12/2002 |
| WO | 2003024434 | 3/2003 |
| WO | 2005042718 | 5/2005 |
| WO | 2005060976 A2 | 7/2005 |
| WO | 2006078713 | 7/2006 |
| WO | 2006083508 | 8/2006 |
| WO | 2007139897 | 12/2007 |
| WO | 2008027547 | 3/2008 |
| WO | 2008045559 | 4/2008 |
| WO | 2009111294 | 9/2009 |
| WO | 2009134616 | 11/2009 |
| WO | 2009143454 | 11/2009 |
| WO | 2011113019 | 9/2011 |
| WO | 2013048965 | 4/2013 |
| WO | 2017027728 | 2/2017 |
| WO | 2017192740 | 11/2017 |
| WO | 2018191676 | 10/2018 |

OTHER PUBLICATIONS

Fan et al., Enhancement of auranofin-induced lung cancer cell apoptosis by selenocystine, a natural inhibitor of TrxR1 in vitro and in vivo, Cell Death & Disease, 5, e1191 2018.

Kurosawa et al., Cytotoxicity induced by inhibition of thioredoxin reductases via multiple signaling pathways: Role of cytosolic phospholipase A2alpha-dependent and -independent release of arachidonic acid, Journal of Cell Physiology, 219(3): 606-616 2009.

Li et al., Auranofin-mediated inhibition of PI3K/AKT/mTOR axis and anticancer activity in non-small cell lung cancer cells. Oncotarget, 7(3): 3548-3558 2016.

Meng, et al. "Potentiation of Endogenous Nitric Oxide With Superoxide Dismutase Inhibits Platelet-Mediated Thrombosis in Injured and Stenotic Arteries," JACC vol. 25, No. Jan. 1, 1995:269-75.

Black, et al. "Inhibition of in vivo myocardial ischemic and reperfusion injury by a synthetic manganese-based superoxide dismutase mimetic," Journal of Pharmacology and Experimental Therapeutics, Sep. 1994, 270 (3) 1208-1215.

GEMZAR product Sheet 1996.

Dennis, et al. "NADPH oxidases and reactive oxygen species at different stages of chronic hypoxia-induced pulmonary hypertension in newborn piglets," Am J Physiol Lung Cell Mol Physiol 297: L596-L607, 2009.

Cuzzocrea, et al. "Superoxide: a key player in hypertension," FASEB Journal vol. Jan. 18, 2004 pp. 94-101.

Wang, et al. "Blockade of Phencyclidine-Induced Cortical Apoptosis and Deficits in Prepulse Inhibition by M40403, a Superoxide Dismutase Mimetic," JPET, vol. 304, No. 1 pp. 266-272.

Sosman & Mier, "Biological drug duo delivers one-two tumor punch," Nature Medicine, vol. 9, No. 6, Jun. 2003 pp. 649-650.

Adringa, et al. "SOD mimics as adjuvants to chemotherapy protocols involving Adriamycin," Oxygen Society Meeting, San Antonio, TX Nov. 2002.

(56) References Cited

OTHER PUBLICATIONS

Coppey, et al. "Effect of M40403 treatment of diabetic rats on endoneurial blood flow, motor nerve conduction velocity and vacular function of epineurial arterioles of the sciatic nerve," British Journal of Pharmacology (2001) 134, 21-29.
Ansel, et al. Pharmaceutical Dosage Forms and Drug Delivery Systems, Published by Lippincott Williams & Wilkins p. 48-5.
Zhang et al. Thioredoxin reductase inhibitors: a patent review, Expert Opinion on Therapeutic Patents, 27(5): 547-556 2017.
Elting et al., The Burdens of Cancer Therapy, Cancer, 98(7): 1531-1539 2003.
Epperly et al., Manganese Superoxide Dismutase-Plasmid/Liposome (MnSOD-PL) Administration Protects Mice from Esophagitis Associated with Fractionated Radiation, Int. J. Cancer (Radiat. Oncol. Invest), 96: 221-231 2001.
Epperly et al., Intraoral Manganese Superoxide Dismutase-Plasmid/Liposome (MnSOD-PL) Radioprotective Gene Therapy Decreases Ionizing Irradiation-induced Murine Mucosal Cell Cycling and Apoptosis, In Vivo, 18:401-410 2004.
Guo et al., Gene Transfer of Human Manganese Superoxide Dismutase Protects Small Intestinal Villi From Radiation Injury, J Gastrointest Surg., 7(2): 229-235 2003.
Lalla et al., Treatment of Mucositis, Including New Medications, Palliative and Supportive Care, 12(5): 348-354 2006.
Murakami, The Chemical Society of Japan, editions, Separation of Optical Isomer quarterly journal, chemical review No. 6, Scientific Societies Press, p. 212-213 (translation) 1989.
Anderson, et al. Two-Year Tumor Outcomes of Phase 2B, Randomized, Double-Blind Trial of Avasopasem Manganese (GC4419) Versus Placebo to Reduce Severe Oral Mucositis Due to Concurrent Radiation Therapy and Cisplatin for Head and Neck Cancer Published:Jun. 17, 2022DOI:https://doi.org/10.1016/j.ijrobp.2022.06.063.
Anderson, et al. Phase IIb, Randomized, Double-Blind Trial of GC4419 Versus Placebo to Reduce Severe Oral Mucositis Due to Concurrent Radiotherapy and Cisplatin for Head and Neck Cancer, Journal of Clinical Oncology 37, No. 34 (Dec. 1, 2019) 3256-3265.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., vol. 100, Issue 2, p. 427-435, Feb. 1, 2018.
ASCO Abstract Effects of GC4419 (avasopasem manganese) on chronic kidney disease in head and neck cancer patients treated with radiation and cisplatin, American Society of Clinical Oncology, 2020 2 pages.
Mapuskar, et al. Mitochondrial Superoxide Dismutase in Cisplatin-Induced Kidney Injury, Antioxidants 2021, 10, 1329 16 pages.
O'Leary, et al. Loss of SOD3 (EcSOD) Expression Promotes an Aggressive Phenotype in Human Pancreatic Ductal Adenocarcinoma, Downloaded from www.clincancerres.aacrjournals.org on Jul. 17, 2020 pp. 1741-1751.
Sishc, et al. Avasopasem manganese synergizes with hypofractionated radiation to ablate tumors through the generation of hydrogen peroxide, Sci. Transl. Med. 13, May 12, 2021 pp. 1-13.
Sishc, et al. Avasopasem Manganese Protects Against Radiation Induced Oral Mucositis and Enhances the Response of Squomous Cell Carcinoma of the Head and Neck to Ionizing Radiation and Radioimmune Therapy, Astro, vol. 108, Issue 3, Suppl. S159, Nov. 1, 2020.
Sishc, et al. Abstract: The radioprotector GC4419 enhances the response of pancreatic ductal adenocarcinoma tumors to high dose per fraction radiation exposure, AACR PDAC Meeting 2019.
Steinbach, et al. Effects of GC4419 (Avasopasem Manganese) on Chronic Kidney Disease in Head and Neck Cancer Patients Treated with Radiation and Cisplatin, ASCO20 May 2020 1 pages.
Kasten et al., Potentiation of Nitric Oxide-Mediated Vascular Relaxation by SC52608, a Superoxide Dismustas Mimic, 1995.
Patent Cooperation Treaty, International Search Report for PCT/US2018/027588, 5 pages Aug. 27, 2018.
Park et al., Synthesis and SOD activity of manganese complexes of pentaaza macrocycles containing amino-and guanidino-auxiliary, Bulletin of the Korean Chemical Society, 32(10): 3787-3789 2011.
Patent Cooperation Treaty, International Search Report for PCT/US2018/018407, 6 pages Sep. 17, 2018.
Tabata et al., Ion-Pair Extraction of Metalloporphyrins into Acetonitrile for Determination of Copper(II), Anal. Chem., 68: 758-762 1996.
Mazzucotelli, et al., Determination of trace amounts of Metalloprotein Species in Marine Mussel Samples by High Performance Liquid Chromatography with Inductively Coupled Plasma Atomic Emission Spectrometric Detection, Analyst., 116: 605-608 1991.
Furuya et al., Determination of Pheophytinatoiron(III) Chlorides by Reverse Phase High Performance Liquid Chromatography, Analytical Sciences, 3: 353-357 1987.
Zhang et al., Quantitative determination of SC-68328 in dog plasma using flow injection and tandem mass spectroscopy, Journal of Mass Spectrometry, 35(3): 354-360 2000.
Sakai et al., Liquid-Chromatographic Separation and Determination of Coproporphyrins I & III in Urine, Clinical Chemistry, 29(2): 350-353 1983.
Riley, Functional Mimics of Supeoxide Dismutase Enzymes and Therapeutic Agents, Chem. Rev., 2572-2587 1999.
Berge et al., Pharmaceutical Salts, J. Pharm. Sci., 66: 1-19 1977.
European Patent Office, European Search Report issued for EP 10179542, 4 pages Aug. 5, 2011.
Patent Cooperation Treaty, International Search Report for PCT/US2017/049960, 5pgs. Feb. 21, 2019.
Fritz et al., Intravenous vitamin C and cancer: A systematic review, Integrative Cancer Therapies, 13(4): 280-300 2014.
McConnell et al., Ascorbate combination therapy: New tool in the anticancer toolbox?, Science Translational Medicine, 6(222): 1-3 2014.
European Patent Office, Extended European Search Report for 16835928.9, publication 3334744, 10 pgs. Feb. 4, 2019.
Cornwell et al., Glyceryl monocaprylate/caprate as a moderate skin penetration enhancer, International Journal of Pharmaceutics, 171: 243-255 1998.
Patent Cooperation Treaty, International Search Report for PCT/US2019/016071, 4pgs. May 14, 2019.
Mapuskar et al., Mitochondrial Superoxide Increases Age-Associated Susceptability of Human Dermal Fibroblasts to Radiation and Chemotherapy, Cancer Research, 77(18): 5054-5067 2017.
Eurasian Patent Office, Search Report for 201892510, 1 page May 28, 2019.
European Patent Office, Extended Search Report for EP App. 18215666.1, 12 pages Jul. 19, 2019.
Di Paolo et al., Reduced development of experimental periodontitis by treatment with M40403, a superoxide dismutase mimetic, European Journal of Pharmacology, 51: 151-157 2005.
McFadden et al., M40403, a superoxide dismutase mimetic, protects cochlear hair cells from gentamicin, but not cisplatin toxicity, Toxicology and Applied Pharmacology, 186: 46-54 2003.
European Patent Office, Extended Search Report for EP App. 17793268.8, 8 pages Nov. 29, 2019.
Fath et al., Enhancement of Carboplatin-Mediated Lung Cancer Cell Killing by Simultaneous Disruption of Glutathione and Thioredoxin Metabolism, Clinical Cancer Research, 17(19): 6206-6217 2011.
Jungwirth et al., Anticancer Activity of Metal Complexes: Involvement, Antioxidants & Redox Signaling, 15(4): 1085-1127 2011.
Cao et al., Mechanisms of ferroptosis, Cell. Mol. Life Sci., 2016, 11:2195-2209 2016.
Rodman III, et al., Enhancement of Radiation Response in Breast Cancer Stem Cells by Inhibition of Thioredoxin and Glutathione Dependent Metabolism, Radiat Res., 2016, 186(4): 385-395 2016.
Raj et al., Selective killing of cancer cells by a small molecule targeting the stress response to ROS, Nature, 475: 231-234 2016.
Samlowski et al., Evaluation of a Superoxide Dismutase Mimetic as an Adjunct to Interleukin 2 Based Cancer Therapy, Madame Curie Report, 230-249 2006.
Samlowski et al., A nonpeptidyl mimic of superoxide dismutase, M40403, inhibits dose-limiting hypotension associated with interleukin-2 and increases its antitumor effects, Nature Medicine, 9:750-755 2003.

(56) References Cited

OTHER PUBLICATIONS

Sishc et al., Superoxide dismutase mimetic GC4419 protects against radiation induced lung fibrosis, exhibits anti-tumor effects, and enhances radiation induced cell killing, 1 pg 2015.
Sishc et al., Superoxide dismutase mimetic GC4419 sensitizes non-small cell lung cancer tumors to high dose per fraction radiation and ameliorates radiation induced lung fibrosis, 1 pg 2016.
Scarbrough, P.M., Inhibitors of glucose and hydroperoxide metabolism potentiate 17AAG-induced cancer cell killing via metabolic oxidative stress, University of Iowa Theses and Dissertations 2011.
Sobhakumari et al., Susceptibility of Human Head and Neck Cancer Cells to Combined Inhibition of Glutathione and Thioredoxin Metabolism, PLOS, 7(10): e48175, 10 pgs 2012.
European Patent Office, Extended Search Report for EP App. 17847659.4, 12 pages Mar. 6, 2020.
Salvemini et al., Reply to Role of manganese superoxide dismutase in cancer, Nature Medicine, 9(9): 1103-1103 Sep. 1, 2003.
Tovmasyan et al., Radiation-Mediated tumor growth inhibition is significantly enhanced with redox-active compounds that cycle with ascorbate, Antioxidants and Redox Signaling, 29(13): 1196-1214 Nov. 1, 2018.
Sishc et al., The radioprotector GC4419 ameliorates radiation induced lung fibrosis while enhancing the response of non-small cell lung cancer tumors to high dose per fraction radiation exposures, American Association of Cancer Research, 1 pg. 2018.
Sichc et al. The superoxide dismutase mimetic GC4419 enhances tumor killing when combined with stereotactic ablative radition, BioRxiv Mar. 11, 2020.
Zhu et al. Lysine 68 acetylation directs MnSOD as a tetrameric detoxification complex versus a monomeric tumor promoter, Nature Communications Jun. 3, 2019.
European Patent Office, Extended European Search Report for 20168046.9, 16 pages Oct. 16, 2020.
Jiang et al., Role of IL-2 in cancer immunotherapy, Oncoimmunology, 5(6);E1163462 Apr. 25, 2016.
Lasry et al., Inflammatory networks underlying colorectal cancer, Nature Immunology, 17(3):230-240 Feb. 16, 2016.
Mikirova et al., Effect of high-dose intravenous vitamin C on inflammation in cancer patients, Journal of Translational Medicine, 10(189): 2 pages 2012.
Riley et al., Manganese Macrocyclic Ligand Complexes as Mimics of Superoxide Dismutase, J. Am. Chem. Soc. 116: 387-388 1994.
Pannala et al., Mechanistic Characterization of the Thioredoxin System in the Removal of Hydrogen Peroxide, Free Radic Biol Med., 78: 42-55 2015.
Kelso et al., A Mitochondria-Targeted Macrocyclic Mn(II) Superoxide Dismutase Mimetic, Chemistry & Biology, 19: 1237-1246 2012.
European Patent Office, Extended European Search Report issued for 18785213.2, 16 pages Feb. 8, 2021.
Laurent et al. Controlling Tumor Growth by Modulating Endogenous Production of Reactive Oxygen Species, Cancer Research, 65(3): 948-956 2005.
Tovmasyan et al., Anticancer therapeutic potential of Mn porphyrin/ ascorbate system, Free Radical Biology and Medicine, 89:1231-1247 2015.
Rawal et al., Manganoporphyrins Increase Ascorbate-Induced Cytotoxicity by Enhancing H2O2 Generation, Cancer Research, 73(16):5232-5241 2013.
Batinic-Haberle et al., An educational overview of the chemistry, biochemistry and therapeutic aspects of Mn porphyrins—From superoxide dismutation to H2O2-driven pathways, Redox Biology, 5:43-65 2015.
Marzano et al., Inhibition of thioredoxin reductase by auranofin induces apoptosis in cisplatin-resistant human ovarian cancer cells, Free Radical Biology & Medicine 42: 872-881 2007.
U.S. Department of Health and Human Services, Food and Drug Administration, Center for Drug Evaluation and Research (CDER), Guidance for Industry Estimating the Maximum Safe Starting Dose in Initial Clinical Trials for Therapeutics in Adult Healthy Volunteers, 30 pages 2005.

Qian et al., Advances in the study of effects of vitamin C on tumor prevention, Youjiang Medical Journal, 36(6): 741-743 2008.
Ghosh et al., A novel manganese complex, Mn-(II) N-(2-hydroxy acetophenone) glycinate overcomes multidrug-resistance in cancer, European Journal of Pharmaceutical Sciences, 49: 737-747 2013.
Serafim et al., Regulating mitochondrial respiration in cancer in: Kanner S. (eds) Tumor Metabolome Targeting and Drug Development, Cancer Drug Discovery and Development, 45 pages 2014.
Liu et al., Mechanisms of the CDK4/6 inhibitor palbociclib (PD 0332991) and its future application in cancer treatment (Review), Oncology Reports, 36: 901-911 2018.
Friend, D. R., Review article: Issues in oral administration of locally acting glucocorticosteroids for treatment of inflammatory bowel disease, Aliment Pharmacol Therapy, 12: 591-603 1998.
Shadad et al., Gastrointestinal radiation injury: Symptoms, risk factors and mechanisms, World Journal of Gastroenterology, 19(2): 185-198 2013.
Yu et al., Intestinal stem cell injury and protection during cancer therapy, Transl Cancer Research, 2(5): 384-396 2013.
Kim et al., Antiproliferative effect of gold(I) compound auranofin through inhibition of STAT3 and telomerase activity in MDA-MB 231 human breast cancer cells, BMB Rep., 46(1): 59-64 2013.
Zou et al., Auranofin induces apoptosis by ROS-mediated ER stress and mitochondrial dysfunction and displayed synergistic lethality with piperlongumine in gastric cancer, Oncotarget, 6(34): 36505-36521 2015.
Declaration under 37 C.F.R. 1.132 of Dennis P. Riley, dated Mar. 7, 2014, and filed in U.S. Appl. No. 11/871,848, filed Mar. 3, 2014.
Declaration under 37 C.F.R. 1.132 of Douglas R. Spitz, dated Feb. 6, 2014, and filed in U.S. Appl. No. 11/871,848, filed Feb. 6, 2014.
Keene, J. L., Declaration under 37 C.F.R. 1.132 May 14, 2014 May 14, 2014.
Mikirova, et al. CAS: 158, 290966, 2012 2012.
Alexandre, et al. "Improvement of the therapeutic index of anti-cancer drugs by the superoxide dismutase mimic mangafodipir," Journal of the National Cancer Institute, vol. 98, No. 4, Feb. 15, 2006, pp. 236-244 Feb. 15, 2006.
Belotte, et al. "Abstract B01: Superoxide dismutase significantly reversed the development of cisplatin resistance in epithelial ovarian cancer," Acquired Resistance, Feb. 13, 2015 pp. B01-B01 Feb. 13, 2015.
Karlsson, et al. "Calmangafodipir [Ca4Mn (DPDP) 5], mangafodipir (MnDPDP) and MnPLED with special reference to their SOD mimetic and therapeutic properties," Drug Discovery Today, vol. 20, No. 4, Apr. 1, 2015 Apr. 1, 2015.
Ahmed, et al. "Tempol, a Superoxide Dismutase Mimetic Agent, Ameliorates Cisplatin-Induced Nephrotoxicity through Alleviation of Mitochondrial Dysfunction in Mice," PLOS ONE, vol. 9, No. 10, Jan. 1, 2014 Jan. 1, 2014.
Wangila, et al. Prevention of cisplatin-induced kidney epithelial cell apoptosis with a Cu superoxide dismutase-mimetic [copper 2/\I/\| (3,5-ditertiarybutylsalicylate) "4(ethanol) "4], Toxicology In Vitro, Elsevier Science, vol. 20, No. 8 Dec. 1, 2006 pp. 1300-1312 Dec. 1, 2006.
Kobayashi, et al. "Enhancement of Anti-Cancer Activity of Cisdiaminedichloroplatinum by the Protein-Bound Polysaccharide of Coriolus Versicolor QUEL (PS-K) In Vitro," Cancer Biotherapy, vol. 9, No. 4 Jan. 1, 1994 pp. 351-358 Jan. 1, 1994.
Karlsson, et al. "First clinical expeirence with the magnetic resonance imaging contrast agent and superoxide dismutase mimetic mangafodipir as an adjunct in cancer chemotherapy—a translational study," Translational Oncology, Feb. 1, 2012 pp. 32-38 Feb. 1, 2012.
Karlsson, et al. "Superior therapeutic index of calmangafodipir in comparison to mangafodipir as a chemotherapy adjunct," Translational Oncology, Dec. 1, 2012 p. 492 Dec. 1, 2012.
Davis, et al. "Manganese Superoxide Dismutase Attenuates Cisplatin-Induced Renal Injury: Importance of Suproxide," Journal of the American Society of Nephrology, vol. 12, No. 12, Dec. 1, 2001 pp. 2683-2690 Dec. 1, 2001.
Mohanty, et al. "Abstract 2929: GC4419 enhances the response of non-small cell lung carcinoma cell lines to cisplatin and cisplatin plus radiation through a ROS-mediated pathway : Cancer Research," AACR Annual Meeting 2018, Jul. 1, 2018 pp. 1-4 Jul. 1, 2018.

(56) References Cited

OTHER PUBLICATIONS

Mapuskar, et al. "Mitochondrial Superoxide Dismutase in Cisplatin-Induced Kidney Injury," Antioxidants, vol. 10, No. 9, Aug. 24, 2021 p. 1329 Aug. 24, 2001.

European Patent Office, Extended European Search Report for 19747505.6 publication 3746085 21 pgs. Feb. 9, 2022 Feb. 9, 2022.

Galera Therapeutics, Inc., A Phase 1 Dose Escalation Study of GC4419 in Combination With Chemoradiation for Squamous Cell Cancer of the Head & Neck, NIH U.S. National Library of Medicine, ClinicalTrials.gov,, 8 pages 2013.

Dyck et al., Immune checkpoints and their inhibition in cancer and infectious diseases, European Journal of Immunology, 47: 765-779 2017.

Wagner, B. A., et al., Myeloperoxidase is involved in H2O2-induced apoptosis of HL-60 human leukemia cells, J. Biol. Chem, 2000, 272(29), 22461-9.

Chen, Q., et al., Pharmacologic ascorbic acid concentrations selectively kill cancer cells: action as a pro-drug to deliver hydrogen peroxide to tissues, PNAS, 2005, 102(38), 13604-9.

Rodriguez, et al., Mitochondrial or cytosolic catalase reverses the MnSOD-dependent inhibition of proliferation by enhancing respiratory chain activity, net ATP production, and decreasing the steady state levels of H2O2, Free Rad. Bio. & Med.

Alexandre, J., et al., Novel Action of Paclitaxel against Cancer Cells: Bystander Effect Mediated by Reactive Oxygen Species, Cancer Research, 2007, 67(8), 3512-3517.

Muscoli, C., et al., On the selectivity of superoxide dismutase mimetics and its importance in pharmacological studies, British Journal of Pharmacology, 2003, 140(3), 445-460.

Sawyer, D. T. et al., How super is superoxide?, Acc. Chem. Res., 1981, 14, 393-400.

Li, S., et al., The Role of Cellular Glutathione Peroxidase Redox Regulation in the Suppression of Tumor Cell Growth by Manganese Superoxide Dismutase, Cancer Res., 2000, 60(14), 3927-3939.

Buettner, G. R., et al., A New Paradigm: Manganese Superoxide Dismutase Influences the Production of H2O2 in Cells and Thereby Their Biological State, Free Radical Biology and Medicine, 2006, 41(8), 1338-50.

Day, B. J., Catalase and glutathione peroxidase mimics, Biochem Pharmacol, 2009, 77(3), 285-296.

Day, B. J. et al., Manganic Porphyrins Possess Catalase Activity and Protect Endothelial Cells against Hydrogen Peroxide-Mediated Injury, Arch. Biochem. & Biophysics, 1997, 347(2), 256-262.

Oberley, L. W., Mechanism of the tumor suppressive effect of MnSOD overexpression, Biomedicine & Pharmacotherapy, 2005, 59, 143-48 Mar. 19, 2005.

Rocklage et al., Manganese(II) N ,N'-Dipyridoxylethylenediamine-N ,N'-diacetate 5,5'-Bis(phosphate). Synthesis and Characterization of a Paramagnetic Chelate for Magnetic Resonance Imaging Enhancement, Inorg. Chem., 1989, 28, 477-485 Sep. 29, 1988.

European Patent Office, Extended Search Report issued for 12835035. 2, dated Mar. 9, 2015.

Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.

McCarthy, A., Metaphore Pharmaceuticals, Chemistry & Biology, 2003, 10(12): 1139-1140.

MacArthur et al., Modulation of serum cytokine levels by a novel superoxide dismutase mimetic, M40401, in an *Escherichia coli* model of septic shock: Correlation with preserved circulating catecholamines, Crit. Care Med., 2003, 31(1): 237245.

Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.

Salvemini et al., Nonpeptidyl mimetics of superoxide dismutase in clinical therapies for diseases, Cell and Mol Life Sci, 2000, 57: 1489-1492.

MacArthur et al., Inactivation of catecholamines by superoxide gives new insights on the pathogenesis of septic shock, PNAS, 2000, 97(17): 9753-9758.

Riley, P.A., Free radicals in biology: oxidative stress and the effects of ionizing radiation, Int. J. Radiat. Biol, 1994, 65(1): 27-33.

Shimizu et al., Neuroprotection against hypoxia-ischemia in neonatal rat brain by novel superoxide dismutase mimetics, Neuroscience Letters, 2003, 346: 41-44.

Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.

Fike et al., Reactive oxygen species from NADPH oxidase contribute to altered pulmonary vascular responses in piglets with chronic hypoxia-induced pulmonary hypertension, 2008, 295(5): L881-L888.

Batinic-Haberle et al., The ortho effect makes manganese(III) meso-tetrakis(N-methylpyridinium-2-yl)porphyrin a powerful and potentially useful superoxide dismutase mimic, J Biol Chem, 1998, 273: 24521-24528.

Batinic-Haberle et al., Pure MnTBAP selectively scavenges peroxynitrite over superoxide: , Free Radic Biol Med, 2009, 46:192-201.

Day et al., Metalloporphyrins are potent inhibitors of lipid peroxidation, Free Radic Biol Med, 1999, 26: 730-736.

Day et al., A metalloporphyrin superoxide dismutase mimetic protects against paraquat-induced endothelial cell injury, in vitro, J Pharmacol Exp Ther, 1995, 275: 1227-1232.

Ferrer-Sueta et al., Reactions of Manganese Porphyrins with Peroxynitrite and Carbonate Radical Anion, J Biol Chem, 2003, 278: 27432-27438.

Kachadourian et al., Flavin-dependent antioxidant properties of a new series of meso-N,N'-dialkyl-imidazolium substituted manganese(III) porphyrins, Biochem Pharmacol, 2004, 67:77-85.

Szabo et al., Evaluation of the relative contribution of nitric oxide and peroxynitrite to the suppression of mitochondrial respiration in immunostimulated macrophages using a manganese, FEBS Letters, 1996, 381:82-86.

Murphy et al., Efficacy of Superoxide Dismutase Mimetic M40403 in Attenuating Radiation-Induced Oral Mucositis in Hamsters, Clin Cancer Res, 2008, 14(13): 4292-4297.

Thompson et al., The manganese superoxide dismutase mimetic, M40403, protects adult mice from lethal total body irradiation, Free Radical Research, 2010; 44(5): 529-540.

Patent Cooperation Treaty, International Search Report issued for PCT/US2012/056921 on Feb. 22, 2013, 5 pages.

Simic et al., Oxygen radicals in biology and medicine, Basic Life Sciences, 1988, vol. 49, Plenum Press, New York and London.

Weiss et al., Catalytic Efficacies of agents that dismutate superoxide, 1991, J. Cell, Biochem, Suppl. 15C, 216 Abstract C110.

Petkau, Scientific basis for the clinical use of superoxide dismutase, 1986, Cancer Treat. Rev. 13, 17.

McCord, Superoxide dismutase: Rationale for use in ruperfusion injury and inflammation, 1986, J. Free Radicals Biol. Med, 2, 307.

Palmer et al., Nitric oxide release accounts for the biological activity of endothelium derived relaxing factor, 1987, Nature, 327, 523-526.

Riley et al., Structure-activity studies and the design of synthetic superoxide dismutase (SOD) mimetics as therapeutics, 2006, Advances in Inorganic Chemistry, 59, 233-263.

Riley et al., Synthesis, characterization, and stability of manganese(II) C-Substituted 1, 4, 7, 10, 12-Pentaazacyclopentadecane complexes exhibity superoxide dismutase activity, J. Inorg. Chem. 1996, 35: 5213-5231.

Riley et al., Toward the rational design of superoxide dismutase mimics: mechanistic studies for the elucidation of substituent effects on the catalytic activity of macrocyclic manganese(II) complexes, JACS, 1997, 119(28): 6522-6528.

Salvemini et al., M40403: Superoxied dismutase mimic, Drugs of the Future, 2000, 25(10): 1027-1033.

Salvemini et al., SOD Mimetics are coming of age, Nature Reviews, 2002, 1: 367-374.

Aykin-Burns et al., Increased levels of superoxide and H2O2 mediate the differential susceptibility of cancer cells versus normal cells to glucose deprivation, Biochem. J., 2009, 418: 29-37 2009.

(56) References Cited

OTHER PUBLICATIONS

Fretland et al., Superoxide Dismutase (SOD) Modulates Acetic Acid-Induced Colitis in Rodents, Gastroenterology, 1991, 100: A581 1991.
Gryglewski et al., Superoxide Anion is involved in the breakdown of Endothelium-Derived Vascular Relaxing Factor, Nature, 1986, 320: 454-456 1986.
Bannister et al., Aspects of the structure, function, and applications of Superoxide Dismutase, CRC Critical Reviews in Biochemistry, 1987, 22(2): 111-180 1987.
Newton et al., Synthesis and characterization of the Mn(II) complex of [15]aneN.sub.5, J. Coord. Chem., 1988, 19: 265-277 1988.
Bradshaw et al., A simple crab-like cyclization procedure to prepare polyaza-crowns and cyclams with one or two unsubstitute macroring Nitrogen atoms or with a Hydroxy group, J. Heterocyclic Chem, 1989, 26: 1431-1435 1989.
Krakowiak et al., Preparation of Triaza-, Tetraaza- and Peraza-Crown Compounds containing Aminoalkyl Side Groups or Unsubstituted Rin Nitrogen Atoms, J. Org. Chem, 1990, 55(10): 3364-3368 1990.
Riley et al., Stopped-flow Kinetic Analysis for Monitoring superoxide decay in aqueous systems, Analytical Biochemistry, 1991, 196: 344-349 1991.
Eldor et al., Perturbation of endothelial functions by ionizing irradiation: effects on prostaglandins, chemoattractants and mitogens, Semin Thromb Hemost, 1989, 15(2): 215-225 1989.
Escribano et al., Aerosol Orgotein (Ontosein) for the Prevention of Radiotherapy-Induced Adverse Effects in Head and Neck Cancer Patients: A feasibility study, Neoplasma, 2002, 49(3): 201-209 2002.
Gridley et al., Chapter 16, Therapeutic Application of Superoxide Dismutase (SOD) (Salvemini and Cuzzocrea, eds.), 2004, 1-20 2004.
Guo et al., Prevention of Radiation-Induced Oral Cavity Mucositis by Plasmid/Liposome Delivery of the Human Manganese Superoxide Dismutase (SOD2) Transgene, Radiat. Red., 2003, 159(3): 361-370 2003.
Knox, et al., Chemotherapy-induced oral mucositis. Prevention and Management, Drugs Aging, 2000, 17(4): 257-267 2000.
Leussink et al., Pathways of Proximal Tubular Cell Death in Bismuth Nephrotoxicity, Toxicol. Appl. Pharmacol., 2002, 180(2): 100-109 2002.
Orrell, R.W., AEOL-10150 (Aeolus), Current Opinion Investig. Drugs, 2006, 7(1): 70-80 2006.
Peterson, D. E. Research advances in oral mucositis. Current Opinion Oncol., 1999, 11(4): 261-266 1999.
Plevova, P. Prevention and treatment of chemotherapy- and radiotherapy-induced oral mucositis: a review. Oral Oncol. 1999; 35(5): 453-470 1999.
Salvemini et al., Amelioration of Joint Disease in a Rat Model of Collagen-Induced Arthritis by M40403, a Superoxide Dismutase Mimetic, Arthritis & Rheumatism, 2001, 44: 2909-2921 2001.
Slikkerveer et al., Pharmacokinetics and Toxicity of Bismuth Compounds, Med. Toxicol. Adverse Drug Exp, 1989, 4(5): 303-323 1989.
Sonis, Oral Mucositis in Cancer Therapy, Support. Oncol., 2004, 2 (supple.3): 3-8 2004.
Sonis et al., Mitigating Effects of Interleukin 11 on Consecutive Courses of 5-Fluorouracil-Induced Ulcerative Mucositis in Hamsters, Cytokine, 1997, 9(8): 605-612 1997.
Ahmad et al., Mitochondrial O.sub2. and H2O2 Mediate Glucose Deprivation-induced Cytotoxicity and Oxidative Stress in Human Cancer Cells, J. Bio. Chem, 2005, 280(6): 4254-4263 2005.
Sonis et al., Transforming Growth Factor-B3 Mediated Modulation of Cell Cycling and Attenuation of 5-Fiuorouracil Induced Oral Mucositis, Oral Oncol., 1997, 33(1): 47-54 1997.
Sonis et al., Defining Mechanisms of action of interleukin-11 on the progression of radiation-induced oral mucositis in hamsters, Oral Oncology, 2000, 36(4): 373-381 2000.
Cuzzocrea et al., C. Tempol, a membrane-permeable radical scavenger, reduces dinitrobenzene sulfonic acid-induced colitis, Eur J Pharmacol., 2000, 406:127-137 2001.
Goodman & Gilman's The Pharmacological Basis of Therapeutics, 10th Edition, McGraw Hill, 1996 1996.
Salvemini et al., A nonpeptidyl mimic of superoxide dismutase with therapeutic activity in rats, Science, 1999, 286: 304-306 1999.
Suenderhauf et al., A Physiologically Based Pharmacokinetic Model of the Minipig: Data Compilation and Model Implementation, Pharm. Res., 2013, 30(1): 1-15 2013.
Cuzzocrea et al., Protective effects of M40401, a selective superoxide dismutase mimetic, on zymosan-induced nonseptic shock, Crit. Care Med., 2004, 21(1): 157-167 2004.
Cuzzocrea et al., Reduction in the development of Cerulein-induced acute pancreatitis by treatment with M40401, a new selective superoxide dismutase mimetic, Shock, 2004, 22(3): 254-261 2004.
Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015) 2015.
Cotton et al., Advanced Inorganic Chemistry, Chapter 5, "Coordination Compounds", 2nd revised edn., Interscience Publishers, 1966, 139 1966.
Cotton et al., Advanced Inorganic Chemistry, Chapter 2, "Coordination Compounds", 2nd revised edn., Interscience Publishers, 1966, 35-36, 45-49 1966.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., 2016, 94(4): 869-870 2016.
Wang et al., Evidence of d-phenylglycine as delivering tool for improving I-dopa absorption, J. Biomed. Sci., 2010, 17: 71-79 2010.
Wikipedia, Cefalexin, retrieved Nov. 2, 2016, from en.wikipedia.org/wiki/Cefalexin, 6 pages 2016.
Hironaka et al., Quantitative Evaluation of PEPT1 Contribution to Oral Absorption of Cephalexin in Rats, Pharm. Res., 2009, 26(1): 40-50 2009.
Knütter et al., Transport of Angiotensin-Converting Enzyme Inhibitors by H+/Peptide Transporters Revisited, J. Pharma. Exp. Thera., 2008, 327(2): 432-441 2008.
Patent Cooperation Treaty, International Search Report for PCT/US2016/046599, dated Nov. 17, 2016, 5 pages Nov. 17, 2016.
Park et al., Facility case volume and outcomes for intensity-modulated radiotherapy in head and neck cancer, Department of Therapeutic Radiology, Yale School of Medicine, 1 pg. Sep. 26, 2016.
Boero et al., Importance of Radiation Oncologist Experience Among Patients With Head-and-Neck Cancer Treated With Intensity-Modulated Radiation Therapy, Journal of Clinical Oncology, 2016, 34(7): 684-696 Mar. 1, 2015.
Ferreira et al., Effect of radiotherapy delay in overall treatment time on local control and survival in head and neck cancer: Review of the literature, Reports of Practical Oncology and Radiotherapy, 2015, 20: 328-339 May 24, 2015.
Anderson et al., Phase 1b Trial of Superoxide Dismutase Mimetic GC4419 to Reduce Chemoradiotherapy-induced Oral Mucositis in Patients with Oral Cavity or Oropharyngeal Carcinoma, Multidisciplinary Head and Neck Cancer Symposium, Scottsdale, Arizona, 17 pgs Feb. 18, 2016.
Hussan et al., A review on recent advances of enteric coating, Journal of Pharmacy, 2012, 2(6): 5-11 2012.
Strickley, R. G., Solubilizing Excipience in Oral and Injectable Formulations, Pharmaceutical Research, 2004, 21(2): 201-230 2004.
Salvemini et al., Pharmacological manipulation of the inammatory cascade by the superoxide dismutase mimetic, M40403, British Journal of Pharmacology, 2001, 132: 815-827 2001.
Masini et al., Reduction of antigen-induced respiratory abnormalities and airway inflammation in sensitized guinea pigs by a superoxide dismutase mimetic, Free Radical Biology & Medicine, 2005, 39: 520-531 2005.

(56) References Cited

OTHER PUBLICATIONS

Salvemini et al., Superoxide Dismutase Mimetics, Pulmonary Pharmacology & Therapeutics, 2002, 15: 439-447 2002.

Weiss et al., Manganese-based Superoxide Dismutase Mimetics Inhibit Neutrophil Infiltration in Vivo, Journal of Biological Chemistry, 1996, 271(42): 26149-26156 1996.

Udipi et al., Modification of inflammatory response to implated biomedical materials in vivo by surface bound superoxide dismutase mimics, Journal of Biomedical Materials Research, 1999, 1-12 1999.

Cuzzocrea et al., Protective effects of M40403, a superoxide dismutase mimetic, in a rodent model of colitis, European Journal of Pharmacology, 2001, 432: 79-89 2001.

Salvemini et al., Protective effects of superoxied dismutase mimetic nd peroxynitrite decomposition catalyst in endotoxin-indueced intestinal damage, 1999, British Journal of Pharmacology, 127(3):685-692 1999.

European Patent Office, Extended European Search Report issued for App. No. 17166668.8, 11 pages Sep. 27, 2017.

Sindoni et al., Combination of immune checkpoint inhibitors and radiotherapy: Review of the literature, Critical Reviews in Oncology/Hematology, 2017, 113: 63-70 2017.

Pardoll, D. M., The blockade of immune checkpoints in cancer immunotherapy, Nat Rev Cancer, 2012. 12(4): 252-264 Mar. 22, 2012.

Jin et al., Clinical Observation on Superoxide Dismutase in Respect of Resistance to Skin Damage Resulting from Radiation, Chinese Journal of Radiological Health, 1993, 2(3): 137 1993.

Zhou et al., Experimental Study on Superoxide Dismutase for Prophylaxis and Treatment of Inflammatory Damage to Mouth Mucosa in Animals, West China Journal of Stomatology, 1996, 14(2) 1996.

Salvemini et al., A nonpeptidyl mimic of superoxide dismutase with therapeutic activity in rats, Science, 1999, 286: 304-306.

Bannister et al., Aspects of the structure, function, and applications of superoxide dismutase, 1987, Crit. Rev. Biochem., 22, 111.

Gryglewski et al., Superoxide anion is involved in the breakdown of endothelium-derived vascular relaxing factor, 1986, Nature, 320, 454-456.

Samlowski et al., A nonpeptidyl mimic of superoxide dismutase, M40403, inhibits does-limiting hyptension associated with interleukin-2 and increases its antitumor effects, 2003, Nature Medicine, 9, 750-755.

Murphy et al., Efficacy of superoxide dismutase mimetic M40403 in attenuating radiation-induced oral mucosisis in hamsters, Clin. Can. Res., 2008, 14(13):4292-4297 2008.

\* cited by examiner

COMBINATION CANCER THERAPY WITH PENTAAZA MACROCYCLIC RING COMPLEX AND ASCORBATE COMPOUND

The present disclosure generally relates to combination therapies for cancer treatment, including administration of a pentaaza macrocyclic ring complex, and an active agent corresponding to an ascorbate compound selected from the group consisting of ascorbic acid, an ascorbic acid derivative, and/or a pharmaceutically acceptable salt thereof.

Transition metal-containing pentaaza macrocyclic ring complexes having the macrocyclic ring system corresponding to Formula A have been shown to be effective in a number of animal and cell models of human disease, as well as in treatment of conditions afflicting human patients.

FORMULA A

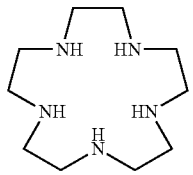

For example, in a rodent model of colitis, one such compound, GC4403, has been reported to very significantly reduce the injury to the colon of rats subjected to an experimental model of colitis (see Cuzzocrea et al., *Europ. J. Pharmacol.*, 432, 79-89 (2001)).

(4403)

GC4403 has also been reported to attenuate the radiation damage arising both in a clinically relevant hamster model of acute, radiation-induced oral mucositis (Murphy et al., *Clin. Can. Res.*, 14(13), 4292 (2008)), and lethal total body irradiation of adult mice (Thompson et al., *Free Radical Res.*, 44(5), 529-40 (2010)). Similarly, another such compound, GC4419, has been shown to attenuate VEGFr inhibitor-induced pulmonary disease in a rat model (Tuder, et al., *Am. J. Respir. Cell Mol. Biol.*, 29, 88-97 (2003)). Additionally, another such compound, GC4401 has been shown to provide protective effects in animal models of septic shock (S. Cuzzocrea, et. al., *Crit. Care Med.*, 32(1), 157 (2004) and pancreatitis (S. Cuzzocrea, et. al., *Shock*, 22(3), 254-61 (2004)).

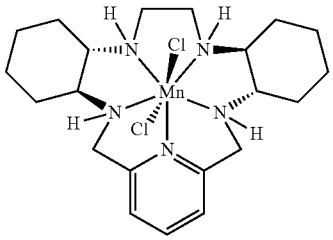

(4419)

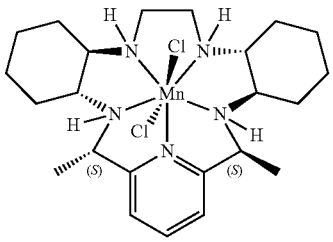

(4401)

Certain of these compounds have also been shown to possess potent anti-inflammatory activity and prevent oxidative damage in vivo. For example, GC4403 has been reported to inhibit inflammation in a rat model of inflammation (Salvemini, et. al., Science, 286, 304 (1999)), and prevent joint disease in a rat model of collagen-induced arthritis (Salvemini et al., *Arthritis & Rheumatism*, 44(12), 2009-2021 (2001)). Yet others of these compounds, MdPAM and MnBAM, have shown in vivo activity in the inhibition of colonic tissue injury and neutrophil accumulation into colonic tissue (Weiss et al., *The Journal of Biological Chemistry*, 271(42), 26149-26156 (1996)). In addition, these compounds have been reported to possess analgesic activity and to reduce inflammation and edema in the rat-paw carrageenan hyperalgesia model, see, e.g., U.S. Pat. No. 6,180,620.

Compounds of this class have also been shown to be safe and effective in the prevention and treatment of disease in human subjects. For example, GC4419 has been shown to reduce oral mucositis in head-and-neck cancer patients undergoing chemoradiation therapy (Anderson, C., *Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC)*, Oral Mucositis Research Workshop, MASCC/ISOO Annual Meeting on Supportive Care in Cancer, Copenhagen, Denmark (Jun. 25, 2015)).

In addition, transition metal-containing pentaaza macrocyclic ring complexes corresponding to this class have shown efficacy in the treatment of various cancers. For example, certain compounds corresponding to this class have been provided in combination with agents such as paclitaxel and gemcitabine to enhance cancer therapies, such as in the treatment of colorectal cancer and lung cancer (non-small cell lung cancer) (see, e.g., U.S. Pat. No. 9,998,893) The 4403 compound above has also been used for treatment in in vivo models of Meth A spindle cell squamous carcinoma and RENCA renal carcinoma (Sam lowski et al., *Nature Medicine*, 9(6), 750-755 (2003), and has also been used for treatment in in vivo models of spindle-cell squamous carcinoma metastasis (Sam lowski et al., *Madame Curie Bioscience Database (Internet)*, 230-249 (2006)). The 4419 compound above has also been used in combination with cancer therapies such as cisplatin and radiation therapy to enhance treatment in in vivo models (Sishc et al., poster for Radiation Reseach Society (2015)).

However, a need remains for enhanced methods for cancer treatment that provide improved efficacy in the killing of cancer cells, while also providing good selectivity in the killing of cancer cells as compared to normal cells. There also remains a need for enhanced methods of treatment to supplement cancer treatments such as radiation therapy and chemotherapy, to improve outcomes for patients receiving these treatments.

Among the various aspects of the present disclosure, therefore, is method of treating a cancer in a mammalian subject afflicted therewith. The method includes administering to the subject an active agent selected from the group consisting of ascorbic acid, an ascorbic acid derivative, and/or a pharmaceutically acceptable salt thereof, and administering to the subject a pentaaza macrocyclic ring complex corresponding to formula (I) below:

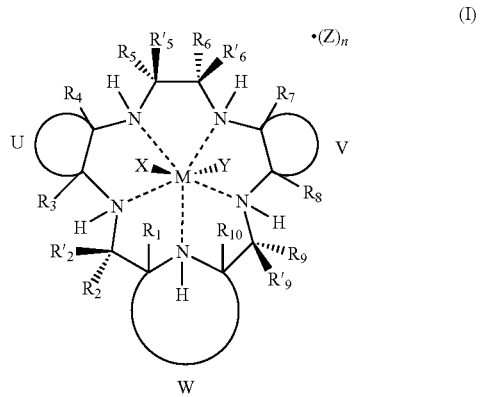

(I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

In another embodiment, among the various aspects of the present disclosure, is a method of treating a cancer in a mammalian subject afflicted therewith, the method including administering to the subject an active agent selected from the group consisting of ascorbic acid, an ascorbic acid derivative, and/or a pharmaceutically acceptable salt thereof, administering to the subject a pentaaza macrocyclic ring complex, and further administering to the subject a cancer therapy that is at least one of radiation therapy and chemotherapy. The pentaaza macrocyclic ring complex can correspond to the formula (I) below:

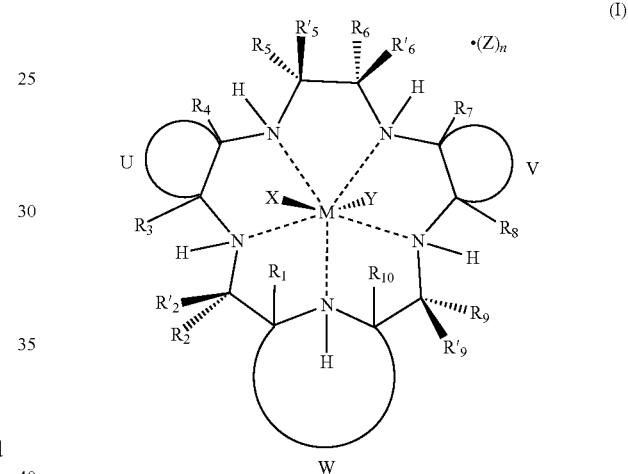

(I)

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

Other objects and features will be in part apparent and in part pointed out hereinafter.

ABBREVIATIONS AND DEFINITIONS

Figure 1:
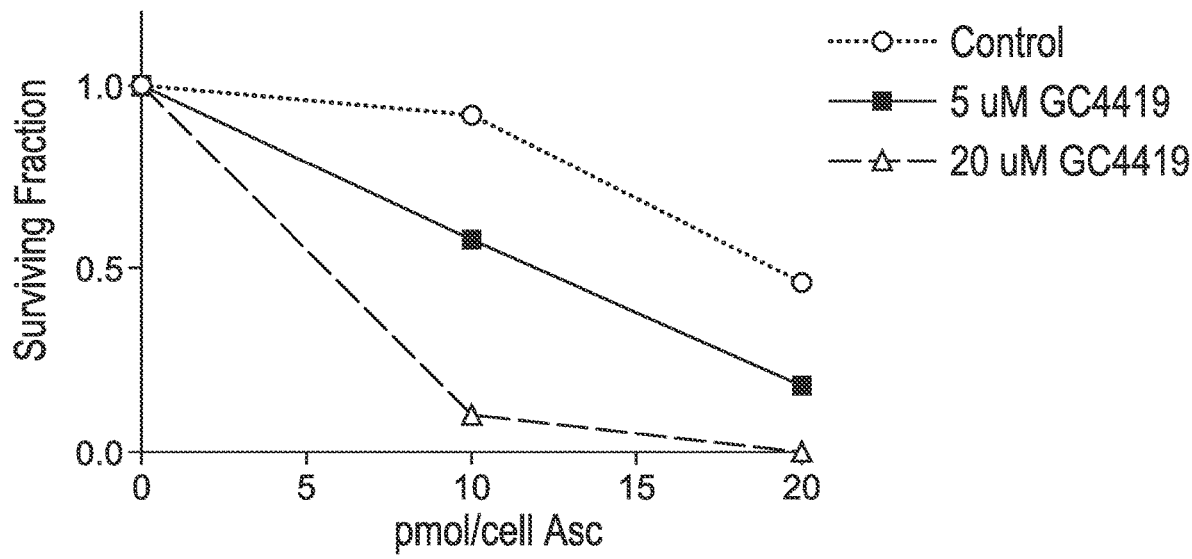
FIG. 1 is a plot showing the surviving fraction of H1299 cells for increasing amounts of ascorbate, as determined by a clonogenic cell survival assay used to determine the effects of the compound alone and in combination with a pentaaza macrocyclic ring complex (GC4419). Non-small cell lung cancer cells (H1299) were exponentially grown in culture for 48 hours. The cells were then treated with 5-20 µM GC4419 for 24 hours and ascorbate (Asc) for one hour, followed immediately by clonogenic assay. The cells were trypsinized, counted, replated at varying lower densities and incubated. Plates were stained and counted for clonogenic survival assays.

The following definitions and methods are provided to better define the present invention and to guide those of ordinary skill in the art in the practice of the present invention. Unless otherwise noted, terms are to be understood according to conventional usage by those of ordinary skill in the relevant art.

"Acyl" means a —COR moiety where R is alkyl, haloalkyl, optionally substituted aryl, or optionally substituted heteroaryl as defined herein, e.g., acetyl, trifluoroacetyl, benzoyl, and the like.

"Acyloxy" means a —OCOR moiety where R is alkyl, haloalkyl, optionally substituted aryl, or optionally substituted heteroaryl as defined herein, e.g., acetyl, trifluoroacetyl, benzoyl, and the like.

"Alkoxy" means a —OR moiety where R is alkyl as defined above, e.g., methoxy, ethoxy, propoxy, or 2-propoxy, n-, iso-, or tert-butoxy, and the like.

"Alkyl" means a linear saturated monovalent hydrocarbon moiety such as of one to six carbon atoms, or a branched saturated monovalent hydrocarbon moiety, such as of three to six carbon atoms, e.g., $C_1$-$C_6$ alkyl groups such as methyl, ethyl, propyl, 2-propyl, butyl (including all isomeric forms), pentyl (including all isomeric forms), and the like.

Moreover, unless otherwise indicated, the term "alkyl" as used herein is intended to include both "unsubstituted alkyls" and "substituted alkyls," the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as alkyl and aralkyl, is meant to include groups that contain from x to y carbons in the chain. For example, the term $C_{x-y}$ alkyl refers to substituted or unsubstituted saturated hydrocarbon groups, including straight chain alkyl and branched chain alkyl groups that contain from x to y carbon atoms in the chain.

"Alkylene" means a linear saturated divalent hydrocarbon moiety, such as of one to six carbon atoms, or a branched saturated divalent hydrocarbon moiety, such as of three to six carbon atoms, unless otherwise stated, e.g., methylene, ethylene, propylene, 1-methylpropylene, 2-methylpropylene, butylene, pentylene, and the like.

"Alkenyl" a linear unsaturated monovalent hydrocarbon moiety, such as of two to six carbon atoms, or a branched saturated monovalent hydrocarbon moiety, such as of three to six carbon atoms, e.g., ethenyl (vinyl), propenyl, 2-propenyl, butenyl (including all isomeric forms), pentenyl (including all isomeric forms), and the like.

"Alkaryl" means a monovalent moiety derived from an aryl moiety by replacing one or more hydrogen atoms with an alkyl group.

"Alkenylcycloalkenyl" means a monovalent moiety derived from an alkenyl moiety by replacing one or more hydrogen atoms with a cycloalkenyl group.

"Alkenylcycloalkyl" means a monovalent moiety derived from a cycloalkyl moiety by replacing one or more hydrogen atoms with an alkenyl group.

"Alkylcycloalkenyl" means a monovalent moiety derived from a cycloalkenyl moiety by replacing one or more hydrogen atoms with an alkyl group.

"Alkylcycloalkyl" means a monovalent moiety derived from a cycloalkyl moiety by replacing one or more hydrogen atoms with an alkyl group.

"Alkynyl" means a linear unsaturated monovalent hydrocarbon moiety, such of two to six carbon atoms, or a branched saturated monovalent hydrocarbon moiety, such as of three to six carbon atoms, e.g., ethynyl, propynyl, butynyl, isobutynyl, hexynyl, and the like.

"Alkoxy" means a monovalent moiety derived from an alkyl moiety by replacing one or more hydrogen atoms with a hydroxy group.

"Amino" means a —$NR^aR^b$ group where $R^a$ and $R^b$ are independently hydrogen, alkyl or aryl.

"Aralkyl" means a monovalent moiety derived from an alkyl moiety by replacing one or more hydrogen atoms with an aryl group.

"Aryl" means a monovalent monocyclic or bicyclic aromatic hydrocarbon moiety of 6 to 10 ring atoms e.g., phenyl or naphthyl.

"Cycle" means a carbocyclic saturated monovalent hydrocarbon moiety of three to ten carbon atoms.

"Cycloalkyl" means a cyclic saturated monovalent hydrocarbon moiety of three to ten carbon atoms, e.g., cyclopropyl, cyclobutyl, cyclopentyl, or cyclohexyl, and the like.

"Cycloalkylalkyl" means a monovalent moiety derived from an alkyl moiety by replacing one or more hydrogen atoms with a cycloalkyl group, e.g., cyclopropylmethyl, cyclobutylmethyl, cyclopentylethyl, or cyclohexylethyl, and the like.

"Cycloalkylcycloalkyl" means a monovalent moiety derived from a cycloalkyl moiety by replacing one or more hydrogen atoms with a cycloalkyl group.

"Cycloalkenyl" means a cyclic monounsaturated monovalent hydrocarbon moiety of three to ten carbon atoms, e.g., cyclopropenyl, cyclobutenyl, cyclopentenyl, or cyclohexenyl, and the like.

"Cycloalkenylalkyl" means a monovalent moiety derived from an alkyl moiety by replacing one or more hydrogen atoms with a cycloalkenyl group, e.g., cyclopropenylmethyl, cyclobutenylmethyl, cyclopentenylethyl, or cyclohexenylethyl, and the like.

"Ether" means a monovalent moiety derived from an alkyl moiety by replacing one or more hydrogen atoms with an alkoxy group.

"Halo" means fluoro, chloro, bromo, or iodo, preferably fluoro or chloro.

"Heterocycle" or "heterocyclyl" means a saturated or unsaturated monovalent monocyclic group of 4 to 8 ring atoms in which one or two ring atoms are heteroatom selected from N, O, or $S(O)_n$, where n is an integer from 0 to 2, the remaining ring atoms being C. The heterocyclyl ring is optionally fused to a (one) aryl or heteroaryl ring as defined herein provided the aryl and heteroaryl rings are monocyclic. The heterocyclyl ring fused to monocyclic aryl or heteroaryl ring is also referred to in this Application as "bicyclic heterocyclyl" ring. Additionally, one or two ring carbon atoms in the heterocyclyl ring can optionally be replaced by a —CO— group. More specifically the term heterocyclyl includes, but is not limited to, pyrrolidino, piperidino, homopiperidino, 2-oxopyrrolidinyl, 2-oxopiperidinyl, morpholino, piperazino, tetrahydropyranyl, thiomorpholino, and the like. When the heterocyclyl ring is unsaturated it can contain one or two ring double bonds provided that the ring is not aromatic. When the heterocyclyl group is a saturated ring and is not fused to aryl or heteroaryl ring as stated above, it is also referred to herein as saturated monocyclic heterocyclyl.

"Heteroaryl" means a monovalent monocyclic or bicyclic aromatic moiety of 5 to 10 ring atoms where one or more, preferably one, two, or three, ring atoms are heteroatom selected from N, O, or S, the remaining ring atoms being carbon. Representative examples include, but are not limited to, pyrrolyl, pyrazolyl, thienyl, thiazolyl, imidazolyl, furanyl, indolyl, isoindolyl, oxazolyl, isoxazolyl, benzothiazolyl, benzoxazolyl, benzimidazolyl, quinolinyl, isoquinolinyl, pyridinyl, pyrimidinyl, pyrazinyl, pyridazinyl, triazolyl, tetrazolyl, and the like.

"Nitro" means —$NO_2$.

"Organosulfur" means a monovalent moiety a —SR group where R is hydrogen, alkyl or aryl.

"Substituted alkyl," "substituted cycle," "substituted phenyl," "substituted aryl," "substituted heterocycle," and "substituted nitrogen heterocycles" means an alkyl, cycle, aryl, phenyl, heterocycle or nitrogen-containing heterocycle, respectively, optionally substituted with one, two, or three substituents, such as those independently selected from alkyl, alkoxy, alkoxyalkyl, halo, hydroxy, hydroxyalkyl, or organosulfur.

"Thioether" means a monovalent moiety derived from an alkyl moiety by replacing one or more hydrogen atoms with an —SR group wherein R is alkyl.

As used herein, (i) the compound referred to herein and in the Figures as compound 401, 4401 or GC4401 is a reference to the same compound, (ii) the compound referred to herein and in the Figures as compound 403, 4403 or GC4403 is a reference to the same compound, (iii) the compound referred to herein and in the Figures as compound 419, 4419 or GC4419 is a reference to the same compound, and (iv) the compound referred to herein and in the Figures as compound 444, 4444 or GC4444 is a reference to the same compound.

DETAILED DESCRIPTION

Aspects of the present disclosure are directed to the treatment of cancer by administration of a pentaaza macrocyclic ring complex according to Formula (I) with at least one active agent corresponding to an ascorbate compound, that is selected from the group consisting of ascorbic acid, an ascorbic acid derivative, and/or a pharmaceutically acceptable salt thereof. Embodiments of the treatment can provide for the enhanced killing of cancerous cells in patients in need thereof, as well as improved selectivity in the killing of cancer cells versus normal cells. The compounds may also be administered as a supplement to another cancer therapy, such as a radiation therapy and/or chemotherapy, to improve the efficacy thereof.

Without being limited to any particular theory, it is believed that the combination of the pentaaza macrocyclic ring complex of Formula (I) with the active agent corresponding to the ascorbate compound may result in an increase in intracellular $H_2O_2$ levels in cancer cells, thereby leading to increased oxidative stress and cytotoxicity. In particular, the pentaaza macrocylic ring complex of Formula (I) is capable of catalyzing the conversion of superoxide anion $O_2^-$ to $H_2O_2$ in cells, and thus is believed to promote cancer cell cytotoxicity at least in part due to the increased $H_2O_2$ production. Furthermore, the active agent corresponding to the ascorbate compound may be capable of providing synergistic effects when combined with the pentaaza macrocyclic ring complex of Formula (I), thereby increasing the cytotoxic effects to a level that is sufficient to impart significant therapeutic benefit. While the exact mechanism of this synergy is not currently known, according to one theory it is believed that the active agent corresponding to the ascorbate compound may generate increased levels of $H_2O_2$ in a manner complementary to the pentaaza macrocylic ring complex of Formula (I), thereby imparting unexpectedly good effects in terms of the selective killing of cancer cells for the combination, in comparison to either compound alone. According to yet another theory, the pentaaza macrocylic complex of Formula (I) may be capable of "regenerating" the active agent corresponding to the ascorbate compound, such that ascorbate compound that has been depleted in the reaction to form $H_2O_2$ can be replenished, thereby maintaining more continuous $H_2O_2$ production within the cancer cells at a level that is greater than that achievable by either compound alone.

Accordingly, by providing a combination of the pentaaza macrocyclic ring complex according to Formula (1) and the active agent corresponding to the ascorbate compound, it has been unexpectedly discovered that synergistic effects in the killing of cancer cells can be provided. The combination can thus be administered for the treatment of cancer, as well as to supplement conventional cancer treatment therapies, with improved treatment efficacy.

Transition Metal Pentaaza Macrocyclic Ring Complex

In one embodiment, the pentaaza macrocyclic ring complex corresponds to the complex of Formula (I):

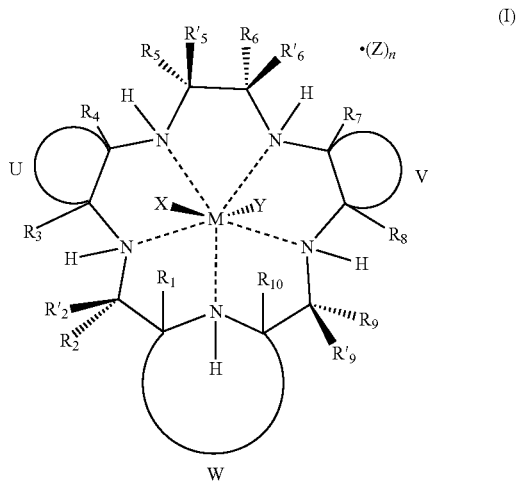

wherein

M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_1)(OR_{12})$, —$P(O)(OR_1)(R_{12})$, and —$OP(O)(OR_{11})(OR_{12})$, wherein $R_{11}$ and $R_{12}$ are independently hydrogen or alkyl;

U, together with the adjacent carbon atoms of the macrocycle, forms a fused substituted or unsubstituted, saturated, partially saturated or unsaturated, cycle or heterocycle having 3 to 20 ring carbon atoms;

V, together with the adjacent carbon atoms of the macrocycle, forms a fused substituted or unsubstituted, saturated, partially saturated or unsaturated, cycle or heterocycle having 3 to 20 ring carbon atoms;

W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;

X and Y represent suitable ligands which are derived from any monodentate or polydentate coordinating ligand or ligand system or the corresponding anion thereof;

Z is a counterion;

n is an integer from 0 to 3; and the dashed lines represent coordinating bonds between the nitrogen atoms of the macrocycle and the transition metal, manganese.

As noted above in connection with the pentaaza macrocyclic ring complex of Formula (I), M is $Mn^{2+}$ or $Mn^{3+}$. In one particular embodiment in which the pentaaza macrocyclic ring complex corresponds to Formula (I), M is $Mn^{2+}$. In another particular embodiment in which the pentaaza macrocyclic ring complex corresponds to Formula (I), M is $Mn^{3+}$.

In the embodiments in which one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are hydrocarbyl, for example, suitable hydrocarbyl moieties include, but are not limited to alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl. In one embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, or heterocyclyl. More preferably in this embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl (e.g., $C_1$-$C_6$ alkyl, more typically $C_1$-$C_4$ alkyl). Thus, for example, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ may be independently hydrogen, methyl, ethyl, propyl, or butyl (straight, branched, or cyclic). In one preferred embodiment, $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl.

In one preferred embodiment in which the pentaaza macrocyclic ring complex corresponds to Formula (I), $R_1$, $R_2$, $R'_2$, $R_3$, $R_4$, $R_5$, $R'_5$, $R_7$, $R_8$, $R_9$, $R'_9$, and $R_{10}$ are each hydrogen and one of $R_6$ and $R'_6$ is hydrogen and the other of $R_6$ and $R'_6$ is methyl. In this embodiment, for example, $R_1$, $R_2$, $R'_2$, $R_3$, $R_4$, $R_5$, $R'_5$, $R_6$, $R_7$, $R_8$, $R_9$, $R'_9$, and $R_{10}$ may each be hydrogen while $R'_6$ is methyl. Alternatively, for example, $R_1$, $R_2$, $R'_2$, $R_3$, $R_4$, $R_5$, $R'_5$, $R'_6$, $R_7$, $R_8$, $R_9$, $R'_9$, and $R_{10}$ may each be hydrogen while $R_6$ is methyl. In another preferred embodiment in which the pentaaza macrocyclic ring complex corresponds to Formula (I), $R_1$, $R_3$, $R_4$, $R_5$, $R'_5$, $R'_6$, $R_7$, $R_8$, and $R_{10}$ are each hydrogen, one of $R_2$ and $R'_2$ is hydrogen and the other of $R_2$ and $R'_2$ is methyl, and one of $R_9$ and $R'_9$ is hydrogen and the other of $R_9$ and $R'_9$ is methyl. In this embodiment, for example, $R_1$, $R'_2$, $R_3$, $R_4$, $R_5$, $R'_5$, $R_7$, $R_8$, $R_9$, and $R_{10}$ may each be hydrogen while $R_2$ and $R'_9$ are methyl. Alternatively, for example, $R_1$, $R_2$, $R_3$, $R_4$, $R_5$, $R'_5$, $R_7$, $R_8$, $R'_9$, and $R_{10}$ may each be hydrogen while $R'_2$ and $R_9$ are methyl. In another embodiment in which the pentaaza macrocyclic ring complex corresponds to Formula (I), $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

In certain embodiments the U and V moieties are independently substituted or unsubstituted fused cycloalkyl moieties having 3 to 20 ring carbon atoms, more preferably 4 to 10 ring carbon atoms. In a particular embodiment, the U and V moieties are each trans-cyclohexanyl fused rings.

In certain embodiments the W moiety is a substituted or unsubstituted fused heteroaromatic moiety. In a particular embodiment, the W moiety is a substituted or unsubstituted fused pyridino moiety. Where W is a substituted fused pyridino moiety, for example, the W moiety is typically substituted with a hydrocarbyl or substituted hydrocarbyl moiety (e.g., alkyl, substituted alkyl) at the ring carbon atom positioned para to the nitrogen atom of the heterocycle. In a one preferred embodiment, the W moiety is an unsubstituted fused pyridino moiety.

As noted above, X and Y represent suitable ligands which are derived from any monodentate or polydentate coordinating ligand or ligand system or the corresponding anion thereof (for example benzoic acid or benzoate anion, phenol or phenoxide anion, alcohol or alkoxide anion). For example, X and Y may be selected from the group consisting of halo, oxo, aquo, hydroxo, alcohol, phenol, dioxygen, peroxo, hydroperoxo, alkylperoxo, arylperoxo, ammonia, alkylamino, arylamino, heterocycloalkyl amino, heterocyloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof, among other possibilities. In one embodiment, X and Y if present, are independently selected from the group consisting of halo, nitrate, and bicarbonate ligands. For example, in this embodiment, X and Y, if present, are halo ligands, such as chloro ligands.

Furthermore, in one embodiment X and Y correspond to —O—C(O)—$X_1$, where each $X_1$ is —C($X_2$)($X_3$)($X_4$), and each $X_1$ is independently substituted or unsubstituted phenyl or —C(—$X_2$)(—$X_3$)(—$X_4$);

each $X_2$ is independently substituted or unsubstituted phenyl, methyl, ethyl or propyl;

each $X_3$ is independently hydrogen, hydroxyl, methyl, ethyl, propyl, amino, —$X_5$C(=O)$R_{13}$ where $X_5$ is NH or O, and $R_{13}$ is $C_1$-$C_{18}$ alkyl, substituted or unsubstituted aryl or $C_1$-$C_{18}$ aralkyl, or —O$R_{14}$, where $R_{14}$ is $C_1$-$C_{18}$ alkyl, substituted or unsubstituted aryl or $C_1$-$C_{18}$ aralkyl, or together with $X_4$ is (=O); and each $X_4$ is independently hydrogen or together with $X_3$ is (=O).

In yet another embodiment, X and Y are independently selected from the group consisting of charge-neutralizing anions which are derived from any monodentate or polydentate coordinating ligand and a ligand system and the corresponding anion thereof; or X and Y are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$.

In the pentaaza macrocyclic ring complex corresponding to Formula (I), Z is a counterion (e.g., a charge-neutralizing anion), wherein n is an integer from 0 to 3. In general, Z may correspond to counterions of the moieties recited above in connection for X and Y.

In combination, among certain preferred embodiments are pentaaza macrocyclic ring complexes corresponding to Formula (I) wherein M is $Mn^{2+}$ or $Mn^{3+}$;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or lower alkyl;

U and V are each trans-cyclohexanyl fused rings;

W is a substituted or unsubstituted fused pyridino moiety;

X and Y are ligands; and

Z, if present, is a charge-neutralizing anion.

More preferably in these embodiments, M is $Mn^{2+}$; $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen or methyl; U and V are each trans-cyclohexanyl fused rings; W is an unsubstituted fused pyridino moiety; and X and Y are independently halo ligands (e.g., fluoro, chloro, bromo, iodo). Z, if present, may be a halide anion (e.g., fluoride, chloride, bromide, iodide).

In yet another embodiment, the pentaaza macrocyclic ring complex is represented by formula (II) below:

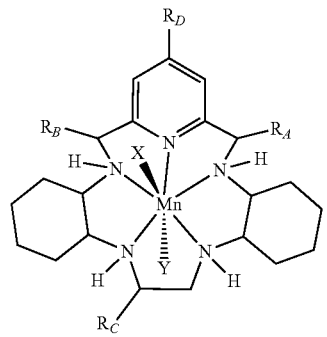

(II)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —O$R_{11}$, —N$R_{11}R_{12}$, —CO$R_{11}$, —CO$_2R_{11}$, —CON$R_{11}R_{12}$, —S$R_{11}$, —SO$R_{11}$, —SO$_2R_{11}$, —SO$_2$N$R_{11}R_{12}$, —N(O$R_{11}$)($R_{12}$), —P(O)(O$R_{11}$)(O$R_{12}$), —P(O)(O$R_{11}$)($R_{12}$), and —OP(O)(O$R_{11}$)(O$R_{12}$), wherein $R_{11}$ and $R_{12}$ are independently hydrogen or alkyl.

Furthermore, in one embodiment, the pentaaza macrocyclic ring complex is represented by formula (III) or formula (IV):

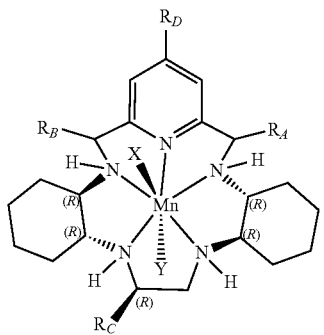

(III)

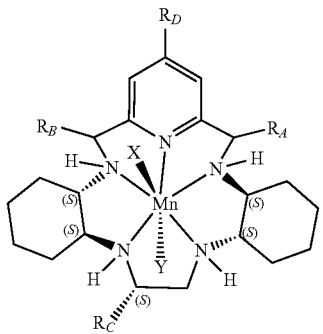

(IV)

wherein

X and Y represent suitable ligands which are derived from any monodentate or polydentate coordinating ligand or ligand system or the corresponding anion thereof; and $R_A$, $R_B$, $R_C$, and $R_D$ are independently hydrogen, hydrocarbyl, substituted hydrocarbyl, heterocyclyl, an amino acid side chain moiety, or a moiety selected from the group consisting of —OR$_{11}$, —NR$_{11}$R$_{12}$, —COR$_{11}$, —CO$_2$R$_{11}$, —CONR$_{11}$R$_{12}$, —SR$_{11}$, —SOR$_{11}$, —SO$_2$R$_{11}$, —SO$_2$NR$_{11}$R$_{12}$, —N(OR$_{11}$)(R$_{12}$), —P(O)(OR$_{11}$)(OR$_{12}$), —P(O)(OR$_{11}$)(R$_{12}$), and —OP(O)(OR$_{11}$)(OR$_{12}$), wherein R$_{11}$ and R$_{12}$ are independently hydrogen or alkyl.

In yet another embodiment, the pentaaza macrocyclic ring complex is a compound represented by a formula selected from the group consisting of formulae (V)—(XVI):

(V)
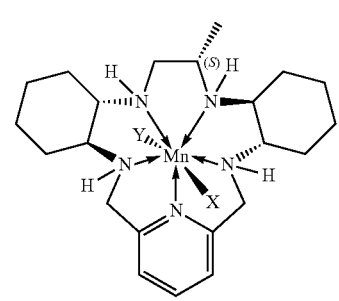

(VI)
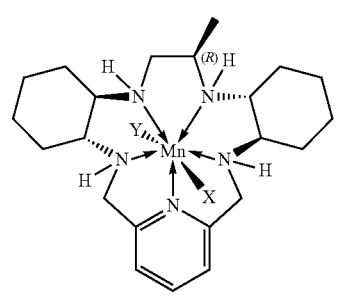

(VII)
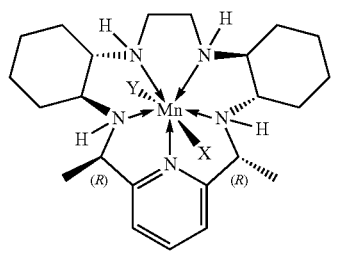

(VIII)
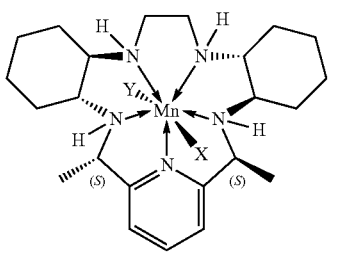

(IX)
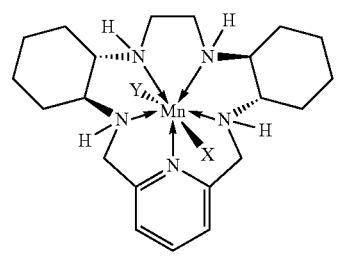

(X)
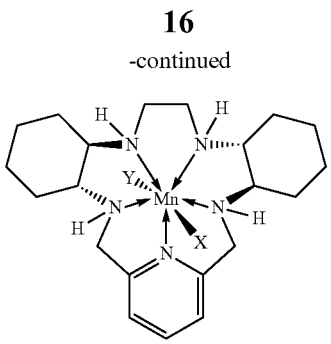

(XI)
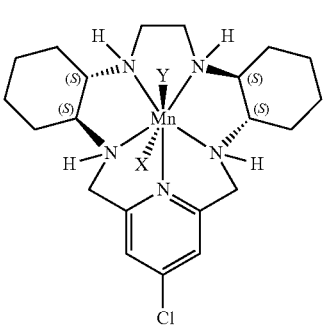

(XII)
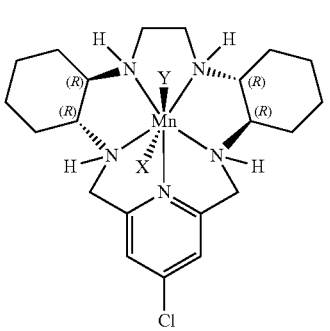

(XIII)
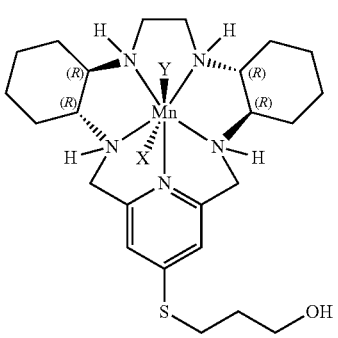

(XIV)
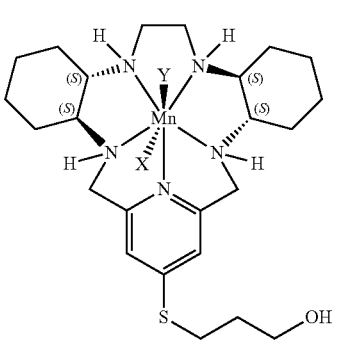

-continued (XV)

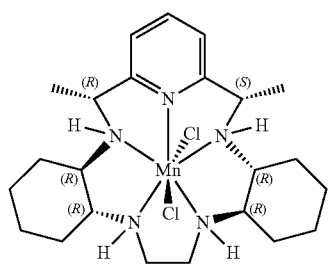

(XVI)

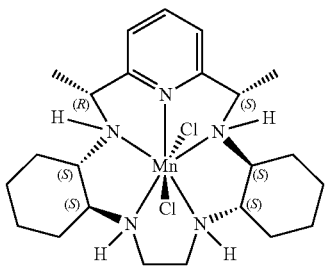

Certain particularly preferred pentaaza macrocyclic ring complexes for use in the methods and compositions described herein include those corresponding to Formulae (2), (3), (4), (5), (6), and (7):

2

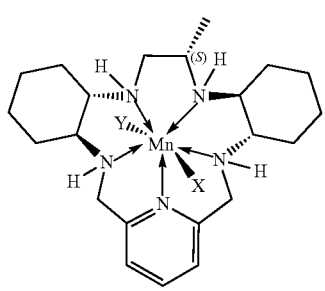

3

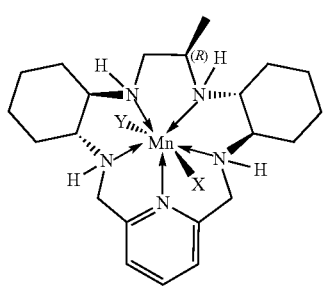

4

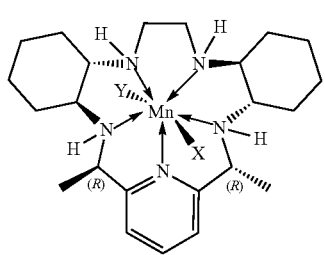

-continued

5

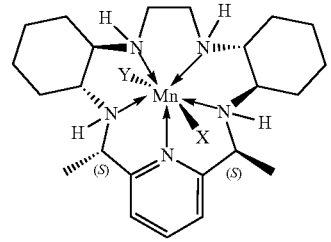

6

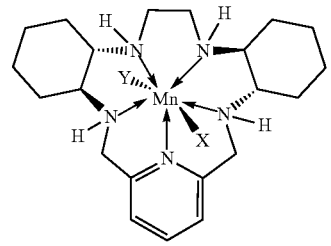

7

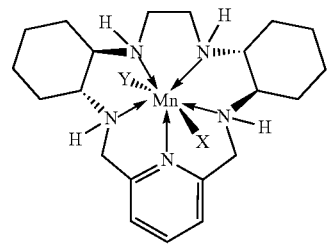

wherein X and Y in each of Formulae (2), (3), (4), (5), (6), and (7) are independently ligands. For example, according to one embodiment, the pentaaza macrocyclic ring complex for use in the methods and compositions described herein include those corresponding to Formulae (2), (3), (4), (5), (6), and (7) with X and Y in each of these formulae being halo, such as chloro. Alternatively, X and Y may be ligands other than chloro.

In a particularly preferred embodiment, the pentaaza macrocyclic ring complex corresponds to Formula (6) or Formula (7):

6

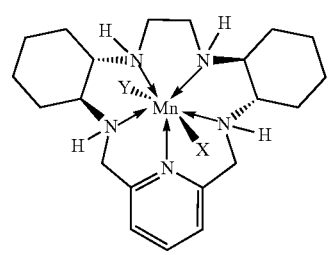

7

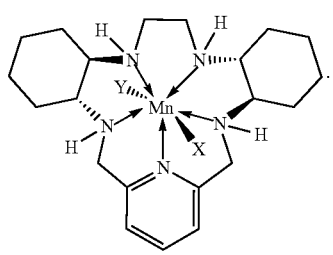

The chemical structures of 6 (such as the dichloro complex form described, for example, in Riley, D. P., Schall, O. F., 2007, *Advances in Inorganic Chemistry*, 59: 233-263) and of 7 herein (such as the dichloro complex form of 7), are identical except that they possess mirror image chirality; that is, the enantiomeric structures are non-superimposable.

For example, the pentaaza macrocyclic ring complex may correspond to at least one of the complexes below:

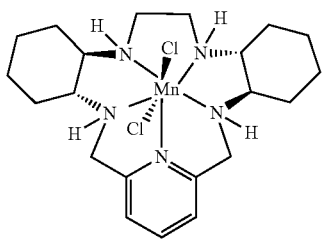
(4403)

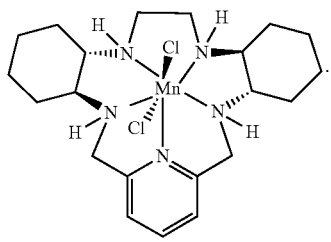
(4419)

In yet another embodiment, the pentaaza macrocyclic ring complex may correspond to at least one of the complexes below, and/or an enantiomer thereof:

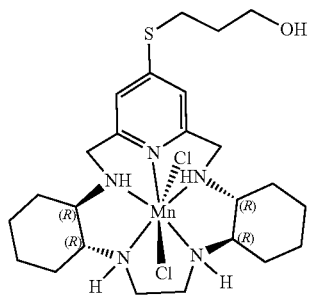
(4432)

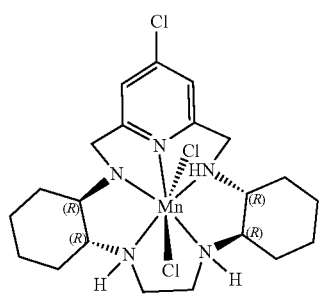
(4409)

In yet another embodiment, the pentaaza macrocyclic ring complex corresponds to Formula (8):

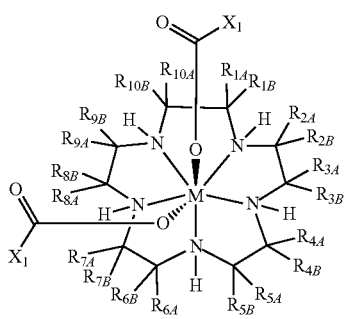
(8)

wherein

M is a transition metal (e.g., $Mn^{2+}$, $Mn^{3+}$);

$R_{1A}$, $R_{1B}$, $R_{2A}$, $R_{2B}$, $R_{3A}$, $R_{3B}$, $R_{4A}$, $R_{4B}$, $R_{5A}$, $R_{5B}$, $R_{6A}$, $R_{6B}$, $R_{7A}$, $R_{7B}$, $R_{8A}$, $R_{8B}$, $R_{9A}$, $R_{9B}$, $R_{10A}$, and $R_{10B}$ are independently:

(i) hydrogen;

(ii) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon of amino acids (i.e., α-amino acids); or (iii) a moiety independently selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, —$OP(O)(OR_{11})(OR_{12})$, and substituents attached to the α-carbon of amino acids (i.e., α-amino acids), wherein $R_{11}$ and $R_{12}$ are independently hydrogen or alkyl;

(iv) a member of a substituted or unsubstituted, saturated, partially saturated, or unsaturated cycle or heterocycle containing 3 to 20 carbon ring atoms comprising (a) $R_{1A}$ or $R_{1B}$ and $R_{2A}$ or $R_{2B}$; $R_{3A}$ or $R_{3B}$ and $R_{4A}$ or $R_{4B}$; $R_{5A}$ or $R_{5B}$ and $R_{6A}$ or $R_{6B}$; $R_{7A}$ or $R_{7B}$ and $R_{8A}$ or $R_{8B}$; $R_{9A}$ or $R_{9B}$ and $R_{10A}$ or $R_{10B}$ together with the carbon atoms to which they are respectively attached;

(b) $R_{10A}$ or $R_{10B}$ and $R_{1A}$ or $R_{1B}$; $R_{2A}$ or $R_{2B}$ and $R_{3A}$ or $R_{3B}$; $R_{4A}$ or $R_{4B}$ and $R_{5A}$ or $R_{5B}$; $R_{6A}$ or $R_{6B}$ and $R_{7A}$ or $R_{7B}$, or $R_{8A}$ or $R_{8B}$ and $R_{9A}$ or $R_{9B}$ together with the carbon atoms to which they are respectively attached; or (c) $R_{1A}$ and $R_{1B}$; $R_{2A}$ and $R_{2B}$; $R_{3A}$ and $R_{3B}$; $R_{4A}$ and $R_{4B}$; $R_{5A}$ and $R_{5B}$; $R_{6A}$ and $R_{6B}$; $R_{7A}$ and $R_{7B}$; $R_{8A}$ and $R_{8B}$, $R_{9A}$ and $R_{9B}$; or $R_{10A}$ and $R_{10B}$ together with the carbon atoms to which they are respectively attached; or (v) a combination of any of (i) through (iv) above;

each $X_1$ is independently substituted or unsubstituted phenyl or —$C(=X_2)(—X_3)(—X_4)$;

each $X_2$ is independently substituted or unsubstituted phenyl or substituted or unsubstituted alkyl;

each $X_3$ is independently hydrogen, hydroxyl, alkyl, amino, —$X_5C(O)R_{13}$ where $X_5$ is NH or O, and $R_{13}$ is $C_1$-$C_{18}$ alkyl, substituted or unsubstituted aryl or $C_1$-$C_{18}$ aralkyl, or —$OR_{14}$, where $R_{14}$ is $C_1$-$C_{18}$ alkyl, substituted or unsubstituted aryl or $C_1$-$C_{18}$ aralkyl, or together with $X_4$ is =O;

each $X_4$ is independently hydrogen or together with $X_3$ is =O; and the bonds between the transition metal, manganese, and the macrocyclic nitrogen atoms and the bonds between the transition metal, manganese, and the oxygen atoms of the axial ligands —OC(O)$X_1$ are coordinate covalent bonds.

In one embodiment, the pentaaza macrocyclic ring complex corresponding to Formula (8) is one of the complexes Formulae ($IE_{R1}$), ($IE_{S1}$), ($IE_{R2}$), ($IE_{S2}$), ($IE_{R3}$), or ($IE_{S3}$):

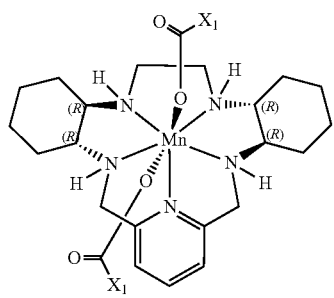
($IE_{R1}$)

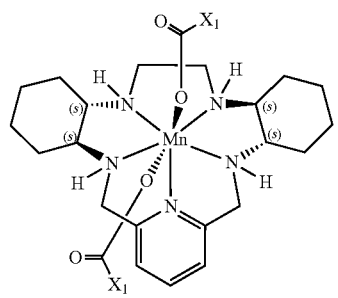
($IE_{S1}$)

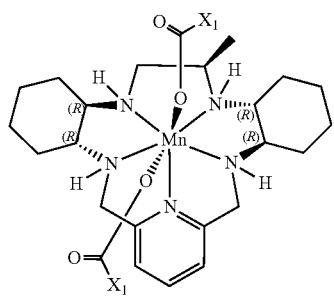
($IE_{R2}$)

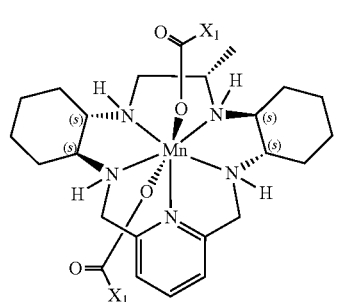
($IE_{S2}$)

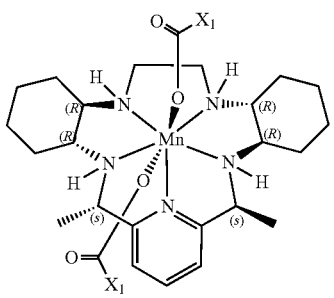
($IE_{R3}$)

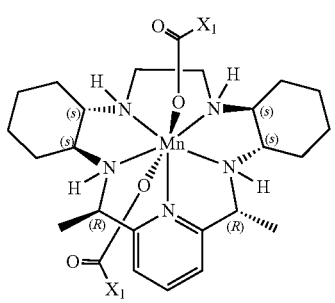
($IE_{S3}$)

wherein

M is $Mn^{+2}$ or $Mn^{+3}$;

each $X_1$ is independently substituted or unsubstituted phenyl or —C($X_2$)($X_3$)($X_4$);

each $X_2$ is independently substituted or unsubstituted phenyl, methyl, ethyl, or propyl;

each $X_3$ is independently hydrogen, hydroxyl, methyl, ethyl, propyl, amino, or together with $X_4$ is =O;

each $X_4$ is independently hydrogen or together with $X_3$ is =O; and the bonds between the manganese and the macrocyclic nitrogen atoms and the bonds between the manganese and the oxygen atoms of the axial ligands —OC(O)$X_1$ are coordinate covalent bonds.

In one embodiment, each $X_1$ is —C($X_2$)($X_3$)($X_4$) and each —C($X_2$)($X_3$)($X_4$) corresponds to any of combinations 1 to 9 appearing in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

In one embodiment, the pentaaza macrocyclic ring complex of formula 8 comprises a compound corresponding to the following formulas:

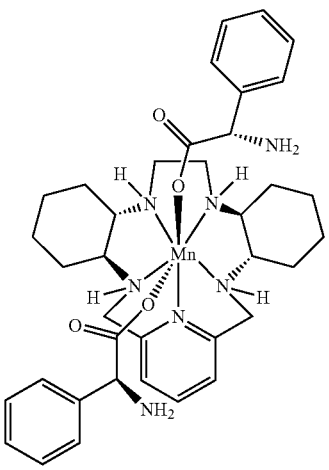

GC4702

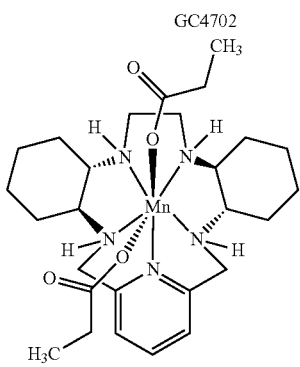

GC4711

In yet another embodiment, the X and Y in pentaaza macrocyclic ring complex of formula (1) correspond to the ligands in formula (8). For example, X and Y in the complex of formula (1) may correspond to —O—C(O)—$X_1$, where $X_1$ is as defined for the complex of Formula (8) above.

In one embodiment, the enantiomeric purity of the pentaaza macrocyclic ring complex is greater than 95%, more preferably greater than 98%, more preferably greater than 99%, and most preferably greater than 99.5%. As used herein, the term "enantiomeric purity" refers to the amount of a compound having the depicted absolute stereochemistry, expressed as a percentage of the total amount of the depicted compound and its enantiomer. In one embodiment, the diastereomeric purity of the pentaaza macrocyclic ring complex is greater than 98%, more preferably greater than 99%, and most preferably greater than 99.5%. As used herein, the term "diastereomeric purity" refers to the amount of a compound having the depicted absolute stereochemistry, expressed as a percentage of the total amount of the depicted compound and its diastereomers. Methods for determining diastereomeric and enantiomeric purity are well-known in the art. Diastereomeric purity can be determined by any analytical method capable of quantitatively distinguishing between a compound and its diastereomers, such as high performance liquid chromatography (HPLC). Similarly, enantiomeric purity can be determined by any analytical method capable of quantitatively distinguishing between a compound and its enantiomer. Examples of suitable analytical methods for determining enantiomeric purity include, without limitation, optical rotation of plane-polarized light using a polarimeter, and HPLC using a chiral column packing material.

In one embodiment, a therapeutically effective amount of the pentaaza macrocyclic ring complex may be an amount sufficient to provide a peak plasma concentration of at least 0.1 μM when administered to a patient. For example, in one embodiment, the pentaaza macrocyclic ring complex may be administered in an amount sufficient to provide a peak plasma concentration of at least 1 μM when administered to a patient. In yet another embodiment, the pentaaza macrocyclic ring complex may be administered in an amount sufficient to provide a peak plasma concentration of at least 10 μM when administered to a patient. Generally, the pentaaza macrocyclic ring complex will not be administered in an amount that would provide a peak plasma concentration greater than 40 μM when administered to a patient. For example, the pentaaza macrocyclic ring complex may be administered in an amount sufficient to provide a peak plasma concentration in the range of from 0.1 μM to 40 μM in a patient. As another example, the pentaaza macrocyclic ring complex may be administered in an amount sufficient to provide a peak plasma concentration in the range of from 0.5 μM to 20 μM in a patient. As another example, the pentaaza macrocyclic ring complex may be administered in an amount sufficient to provide a peak plasma concentration in the range of from 1 μM to 10 μM in a patient.

In yet another embodiment, a dose of the pentaaza macrocyclic ring complex that is administered per kg body weight of the patient may be at least 0.1 mg/kg. For example, the dose of the pentaaza macrocyclic ring complex that is administered per kg body weight of the patient may be at least 0.5 mg/kg. As another example, the dose of the pentaaza macrocyclic ring complex that is administered per kg body weight of the patient may be at least 1 mg/kg. Generally, the dose of the pentaaza macrocyclic ring complex that is administered per kg body weight of the patient will not exceed 10 mg/kg. For example the dose of the pentaaza macrocyclic ring complex that is administered per kg body weight of the patient may be in the range of from 0.1 to 10 mg/kg. As another example, the dose of the pentaaza macrocyclic ring complex that is administered per kg body weight of the patient may be in the range of from 0.5 to 5 mg/kg. As yet a further example, the dose of the pentaaza macrocyclic ring complex that is administered per kg body weight of the patient may be in the range of from 1 to 5 mg/kg.

In one embodiment, the dosages and/or plasma concentrations discussed above may be particularly suitable for the pentaaza macrocyclic ring complex corresponding to GC4419, although they may also be suitable for other pentaazamacrocylic compounds. In addition, one or ordinary skill in the art would recognize how to adjust the dosages and/or plasma concentrations based on factors such as the molecular weight and/or activity of the particular compound being used. For example, for a pentaazamacrocyclic ring complex having an activity twice that of GC4419, the dosage and/or plasma concentration may be halved, or for a pentaazamacrocyclic ring complex having a higher molecular weight that GC4419, a correspondingly higher dosage may be used.

Ascorbate Compound

In one embodiment, the active agent administered with the pentaaza macrocyclic ring complex corresponds to an ascorbate compound selected from the group consisting of ascorbic acid, an ascorbic acid derivative, and/or a pharmaceutically acceptable salt thereof. That is, the ascorbate compound may be in the form of at least one of ascorbic acid, a pharmaceutically acceptable salt form of ascorbic acid, a derivative form of ascorbic acid, and a pharmaceutically acceptable salt form of the ascorbic acid derivative. The ascorbate compound that is selected from the group consisting of ascorbic acid, the ascorbic acid derivative, and/or the pharmaceutically acceptable salt thereof may be capable of imparting synergistic effects in the killing of cancer cells when combined with the pentaaza macrocyclic ring complex of Formula (I) described herein.

Ascorbic acid is known by its IUPAC name as (5R)-[(1S)-1,2-Dihydroxyethyl]-3,4-dihydroxyfuran-2(5H)-one, and is also referred to by its common name vitamin C. The structural formula of ascorbic acid is shown below:

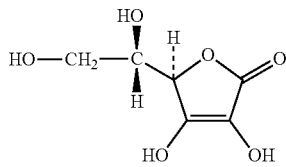

Ascorbic acid derivatives of ascorbic acid can encompass a variety of different compounds, including but not limited to ascorbic acid esters, phosphorylated ascorbic acid compounds, ascorbic acid analogs, and also stereoisomers of ascorbic acid, such as erythorbic acid (D-isoascorbic acid).

In one embodiment, the ascorbic acid derivative comprises an ascorbic acid ester, the general structure of which is shown below:

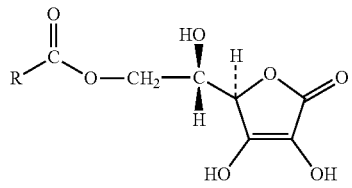

where R can be, for example, a branched or unbranched alkyl group having up to 25 carbon atoms. In one embodiment, the ascorbic acid ester may be a fatty acid ester having a saturated or unsaturated fatty acid chain for the group R. The fatty acid chain may be, for example at short chain fatty acid of less than 6 carbons, a medium chain fatty acid of 6-12 carbon atoms, or a long chain fatty acid of more than 12 carbon atoms. In one embodiment, the fatty acid that forms the ascorbyl ester is selected from the group consisting of caprylic acid, capric acid, lauric acid, myristic acid, palmitic acid, stearic acid, arachidic acid, behenic acid, palmitoleic acid, oleic acid, myristoleic acid, linoleic acid, arachidonic acid, and eicosapentaenoic acid. For example, the ascrobyl acid ester may be a medium to long chain fatty acid ester such as at least one of ascorbyl palmitate, ascorbyl stearate, ascorbyl laurate, ascorbyl myristate and ascorbyl behenate. The ascorbic acid ester can also comprise shorter chain esters such as ascorbyl acetate and ascorbyl propionate. In one embodiment, the ascorbic acid derivative can also comprise an ester of an ascorbic acid isomer, such as an erythorbic acid ester.

In yet another embodiment, the ascorbic acid derivative can comprise a phosphorylated form of ascorbic acid. For example, the phosphorylated derivative can be formed by replacing one or more of the OH groups of the ascorbic acid compound with a phosphate group, such as in the formation of 2-phospho-L-ascorbic acid. In one embodiment, the phosphorylated ascorbic acid derivative can comprise a phosphorylated ascorbic acid ester derivative, such as a phosphorylated derivative of the fatty acid esters of ascorbic acid and/or erythorbic acid described above. For example, the phosphorylated ascorbic acid derivative can comprise a phosphorylated ascorbic acid palmitate. In a further embodiment, the ascorbic acid derivative can comprise an ascorbic acid having a sulfur atom substituted at the C6 position that is conjugated to a triphenylphosphonium group via a linker moiety (e.g., an alkyl linker moiety such as a $C_3$-$C_{21}$ linking group), such as for example in the "MitoC" compounds described by Finichiu et al, *Free Radic. Biol. Med.* 89: 668-678 (2015).

In yet another embodiment, ascorbic acid derivatives can comprise derivatives of ascorbic acid having substitutions at the 2, 3, 4, 5 and 6 carbons of ascorbic acid. The substitutions may be, for example, amino, sulfato, fatty acid, isopropylidene, deoxy, fluoro, chloro, bromo, iodo, phenyl, nitrophenyl and trifluorophenyl substitutions. For example, the ascorbic acid derivatives can comprise at least one of 2-amino-1-ascorbic acid, 2-sulfato-1-ascorbic acid, 2-O-octadecyl-1-ascorbic acid, 2-O-myristyl-1-ascrobic acid, 3-O-benzyl-1-ascorbic acid, 3-O-octadecyl-1-ascorbic acid, 5,6-isopropylidene-1-ascorbic acid, 3-O-Methoxymethyl, 5,6-isopropylidene-1-ascorbic acid, 6-deoxy-1-ascorbic acid, 6-deoxyfluoro-1-ascorbic acid, 6-deoxychloro-1-ascorbic acid, 6-deoxybromo-1-ascorbic acid, 6-deoxyiodo-1-ascorbic acid, 6-deoxyphenyl-1-ascorbic acid, 6-deoxynitrophenyl-1-ascorbic acid, and 6-deoxytrifluorophenyl-1-ascorbic acid, as described by Rumset et al, *The Journal of Biological Chemistry* 274 (33): 23215-23222 (1999).

According to yet another embodiment, the ascorbic acid derivatives comprise lipophilic analogs of ascorbic acid comprising 4-benzoyl-3-hydroxyfuran-2-(5H)-ones and 4-acetyl-5-aryl-3,4-dihydro-furan-2(5H)-ones, as described by Weber et al, *J. Pharm. Pharmacol.* 52: 523-530 (2000). In particular, in one embodiment, the compounds can contain a substitution of hydrogen at the C4 carbon of ascorbic acid (instead of the moiety $CH_2(OH)$—$CH_2(OH)$), and a substitution of C(=O)—Ar at the $C_3$ carbon of ascorbic acid (instead of OH), where Ar can be any of 4-$OCH_3C_6H_4$, 3-$OCH_3C_6H_4$, 2-$OCH_3C_6H_4$, 3,4-$OCH_3C_6H_4$, 3,4,5-$OCH_3C_6H_2$, 4-OH $C_6H_4$, 3-OH $C_6H_4$, and/or 2-OH $C_6H_4$. In yet another embodiment, the compounds can contain a substitution of 2-OH $C_6H_4$ at the $C_4$ carbon of ascorbic acid (instead of the moiety $CH_2(OH)$—$CH_2(OH)$), and a substitution of C(=O)—Ar at the $C_3$ carbon of ascorbic acid (instead of OH), where Ar can be any of 3-OH $C_6H_4$, and/or 4-$OCH_3C_6H_4$. In yet another embodiment, the compounds can contain a substitution of Ar at the $C_4$ carbon of ascorbic acid (instead of the moiety $CH_2(OH)$—$CH_2(OH)$), and a substitution of C(=O)—$CH_3$ at the $C_3$ carbon of ascorbic acid (instead of OH), where Ar can be any of 4-$OCH_3C_6H_4$, 3-$OCH_3C_6H_4$, 2-$OCH_3C_6H_4$, 4-OH $C_6H_4$, 3-OH $C_6H_4$, and 4-OH-3,5-$OCH_3C_6H_2$.

In one embodiment, the pharmaceutically acceptable salt of the ascorbic acid and/or ascorbic acid derivative can comprise any salt form that is acceptable for administration to a patient. Examples of pharmaceutically acceptable salt forms can include alkali and/or alkaline metal salts, such as one or more of sodium salts, magnesium salts, calcium salts and potassium salts. For example, the pharmaceutically acceptable salt of ascorbic acid may be selected from the group consisting of sodium ascorbate, magnesium ascorbate, calcium ascorbate and potassium ascorbate. In one embodiment, the pharmaceutically acceptable salt may be sodium ascorbate. Other inorganic or organic salt forms of the ascorbic acid and/or ascorbic acid derivative may also be provided.

The active agent corresponding to the ascorbate compound may be administered in an amount that is sufficient to provide a therapeutic effect. For example, the ascorbate compound may be administered in an amount with respect to an amount of the pentaaza macrocylic ring complex of Formula (I) that provides for therapeutic effects in the treatment of cancer. In one embodiment, the active agent corresponding to the ascorbate compound is administered in a ratio by weight of the ascorbate compound to the pentaaza macrocyclic ring complex of Formula (I) of at least 20:1. In another embodiment, the active agent corresponding to the ascorbate compound is administered in a ratio by weight of the active agent corresponding to the ascorbate compound to the pentaaza macrocyclic ring complex of Formula (I) of at least 100:1. In yet another embodiment, a ratio by weight of the active agent corresponding to the ascorbate compound to the pentaaza macrocyclic ring complex of Formula (I) of at least 1,000:1. In yet another embodiment, a ratio by weight of the active agent corresponding to the ascorbate compound to the pentaaza macrocyclic ring complex of Formula (I) of at least 10,000:1. Generally, a ratio by weight of the active agent corresponding to the ascorbate compound to the pentaaza macrocyclic ring complex of Formula (I) will not exceed 50,000:1. For example, the ratio by weight of the ascorbate compound to the pentaaza macrocyclic ring complex of Formula (I) may be in the range of from 20:1 to 50,000:1. As another example, the ratio by weight of the ascorbate compound to the pentaaza macrocyclic ring complex of Formula (I) may be in the range of from 50:1 to 10,000:1. As yet another example, the ratio by weight of the ascorbate compound to the pentaaza macrocyclic ring complex of Formula (I) may be in the range of from 100:1 to 1,000:1.

In one embodiment, a therapeutically effective amount of the active agent corresponding to the ascorbate compound may be an amount sufficient to provide a peak plasma concentration of at least 1 mM when administered to a patient. For example, in one embodiment, the active agent corresponding to the ascorbate compound may be administered in an amount sufficient to provide a peak plasma concentration of at least 2 mM when administered to a patient. As another example, in one embodiment, the active agent corresponding to the ascorbate compound may be administered in an amount sufficient to provide a peak plasma concentration of at least 5 mM when administered to a patient. For example, in one embodiment, the active agent corresponding to the ascorbate compound may be administered in an amount sufficient to provide a peak plasma concentration of at least 10 mM when administered to a patient. In yet another embodiment, the active agent corresponding to the ascorbate compound may be administered in an amount sufficient to provide a peak plasma concentration of at least 20 mM when administered to a patient. Generally, the active agent corresponding to the ascorbate compound will not be administered in an amount that would provide a peak plasma concentration greater than 40 mM when administered to a patient. For example, the active agent corresponding to the ascorbate compound may be administered in an amount sufficient to provide a peak plasma concentration in the range of from 1 mM to 40 mM in a patient. As another example, the active agent corresponding to the ascorbate compound may be administered in an amount sufficient to provide a peak plasma concentration in the range of from 2 mM to 25 mM in a patient. As another example, the active agent corresponding to the ascorbate compound may be administered in an amount sufficient to provide a peak plasma concentration in the range of from 5 mM to 25 mM in a patient. As another example, the active agent corresponding to the ascorbate compound may be administered in an amount sufficient to provide a peak plasma concentration in the range of from 10 mM to 25 mM in a patient. As another example, the active agent corresponding to the ascorbate compound may be administered in an amount sufficient to provide a peak plasma concentration in the range of from 15 mM to 25 mM in a patient.

In yet another embodiment, a dose of the active agent corresponding to the ascorbate compound that is administered per kg body weight of the patient may be at least 100 mg/kg. For example, the dose of the active agent corresponding to the ascorbate compound that is administered per kg body weight of the patient may be at least 500 mg/kg. As another example, the dose of the active agent corresponding to the ascorbate compound that is administered per kg body weight of the patient may be at least 1,000 mg/kg. Generally, the dose of the active agent corresponding to the ascorbate compound that is administered per kg body weight of the patient will not exceed 2,000 mg/kg. For example the dose of the active agent corresponding to the ascorbate compound that is administered per kg body weight of the patient may be in the range of from 100 to 2,000 mg/kg. As another example, the dose of the active agent corresponding to the ascorbate compound that is administered per kg body weight of the patient may be in the range of from 500 to 1,500 mg/kg. As yet a further example, the dose of the active agent corresponding to the ascorbate compound that is administered per kg body weight of the patient may be in the range of from 1,000 to 1,500 mg/kg.

In one embodiment, the dosages and/or plasma concentrations discussed above may be particularly suitable for the ascorbate compound corresponding to ascorbic acid, although they may also be suitable for other ascorbate compounds. In addition, one or ordinary skill in the art would recognize how to adjust the dosages and/or plasma concentrations based on factors such as the molecular weight and/or activity of the particular compound being used. For example, for an ascorbate compound having an activity twice that of ascorbic acid, the dosage and/or plasma concentration may be halved, or for an ascorbate compound having a higher molecular weight that of ascorbic acid, a correspondingly higher dosage may be used. The ratio of ascorbate compound to pentaaza macrocyclic compound by weight may also be correspondingly adjusted in relation to the particular activities and/or molecular weights, as well as other properties, of the specific compounds being used.

Other Active Agents

In one embodiment, one or more other active agents can be combined in an administration regimen with the pentaazamacrocyclic ring complex of Formula (I) and the active agent corresponding to the ascorbate compound, to provide for improved treatment. For example, the other active agents can comprise one or more of a thioredoxin reductase inhibitor that inhibits the metabolism of $H_2O_2$, and a glutathione depleting agent that is capable of inhibiting glutathione dependent $H_2O_2$ pathways, so as to increase intracellular levels of $H_2O_2$, as well as other suitable active agents. The other active agents can be used as a part of a combination therapies and/or combination formulation with the pentaazamacrocyclic ring complex and active agent corresponding to the ascorbate compound, such as any of the combination therapy methods and/or formulations described herein.

Thioredoxin Reductase Inhibitor

In one embodiment, the thioredoxin reductase inhibitor is a compound that inhibits thioredoxin reductase, the enzyme that catalyzes the reduction of thioredoxin. Thioredoxin can act as a reducing agent to reduce levels of reactive oxygen species, such as $H_2O_2$. Accordingly, the inhibition of thioredoxin reductase maintains thioredoxin in its reduced state, thereby decreasing the ability of thioredoxin to remove reactive oxygen species such as $H_2O_2$. In one embodiment, a thioredoxin reductase inhibitor selected for combination with the pentaaza macrocyclic ring complex and ascorbate compound is a compound that exhibits the thioredoxin reductase inhibition effect while also being therapeutically acceptable to the patient receiving the compound. For example, the thioredoxin reductase inhibitor may be at least one of auranofin, auro-thio-glucose, chloro(triethylphosphine)gold(I) (TEPAu), aurothiomalate, gold sodium thiomalate, sodium aurothiosulfate, gold acetate, 1,2,5-selenadiazole and derivatives thereof (e.g., as described in Liang et al, *Eur. J. Med. Chem.*, 84, 335-342 (2014)), metal complexes with 2-acetylpyridine-N(4)-orthochlorophenylthiosemicarbazone, such as palladium (II), platinum (II), bismuth (III), antimony (III) and gold (III) metal complexes (e.g., as described in Parillha et al, *Eur. J. Med. Chem.*, 84, 537-544 (2014)), and/or a pharmaceutically acceptable salt thereof. By way of further example, the thioredoxin reductase inhibitor may be at least one of auranofin (gold (+1)cation; 3,4,5-triacetyloxy-6-(acetyloxymethyl)oxane-2-thiolate; triethylphosphanium) and auro-thio-glucose gold (1) (2S,3S,4R,5S)-3,4,5-trihydroxy-6-(hydroxymethyl)-oxane-2-thiolate).

Glutathione Depleting Agent

In one embodiment, the glutathione depleting agent is an agent that decreases levels of glutathione in the cancerous cells. The glutathione depleting agent may be a compound that acts to deplete glutathione by any of a number of different mechanisms. For example, in one embodiment, the glutathione depleting agent is a glutathione synthesis inhibitor, such as buthionine sulfoximine. In another embodiment, the glutathione depleting agent is an inhibitor of $x_c^-$ cysteine/glutamate antiporter, such as sulfasalazine. In yet another embodiment, the glutathione depleting agent is a glutathione reductase inhibitor, such as 2-acetylamino-3-[4-(2-acetylamino-2-carboxyethylsulfanylthiocarbonyamino) phenylthiocarbamolylsulfanyl] propionic acid (2-AAPA). In one embodiment, the glutathione depleting agent can comprise at least one of buthionine sulfoximine, sulfasalazine, piperlongumine, N-ethylmaleimide, N-pyrenylmaleimide, 2-AAPA, erastin, sorafenib, 1S,3R-RSL3, DPI19, DPI18, DPI17, DPI13, DPI12, DPI10 (ML210), DPI7(ML162) (Cao et al., *Cell Mol. Life Sci.*, (2016)), and altretamine, and/or pharmaceutically acceptable salts thereof. Structures of some of these suitable glutathione depleting agents are as follows:

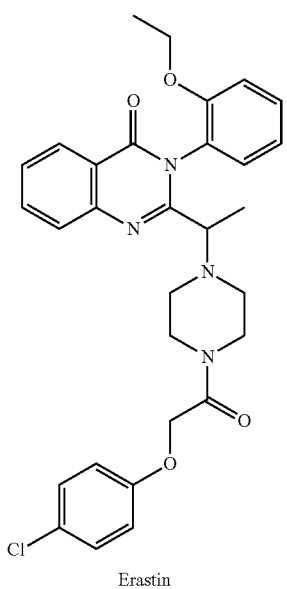

Erastin

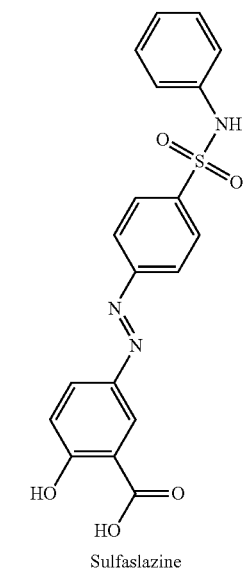

Sulfaslazine

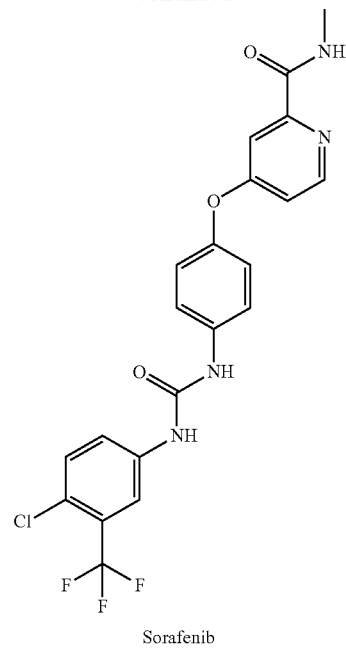

Sorafenib

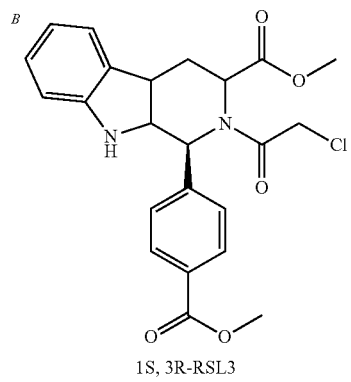

1S, 3R-RSL3

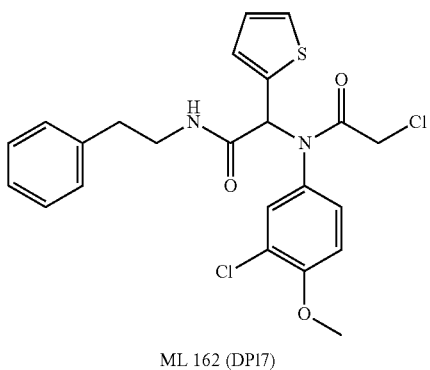

ML 162 (DPI7)

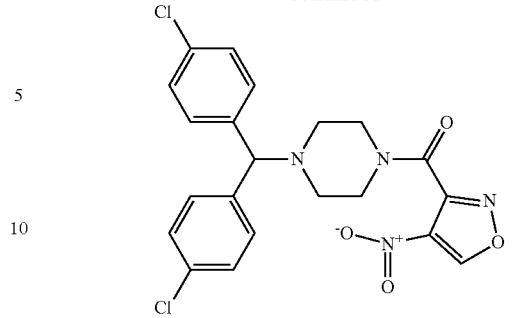

ML210 (DPI10)

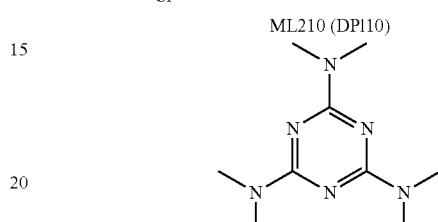

Altretamine

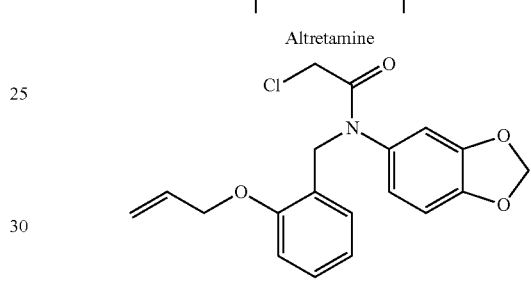

DPI13 = N-[2-(allyloxy)benzyl]-N-1,3-benzodioxol-5-yl-2-chloroacetamide

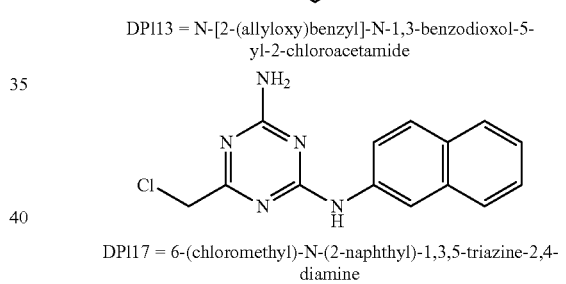

DPI17 = 6-(chloromethyl)-N-(2-naphthyl)-1,3,5-triazine-2,4-diamine

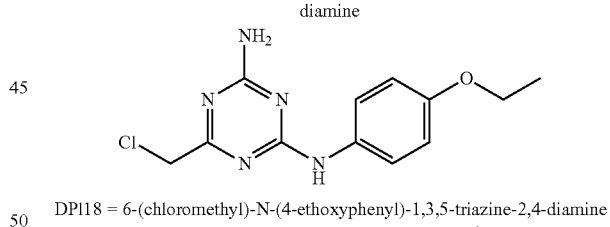

DPI18 = 6-(chloromethyl)-N-(4-ethoxyphenyl)-1,3,5-triazine-2,4-diamine

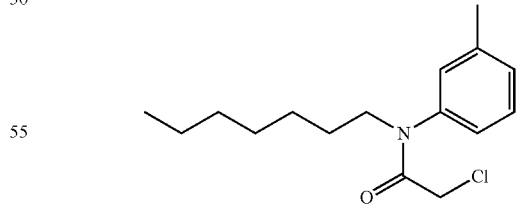

DPI19 = 2-chloro-N-heptyl-N-m-tolyl-acetamide

In one embodiment, the glutathione depleting agent comprises at least one of buthionine sulfoximine and sulfasalazine, and/or a pharmaceutically acceptable salt thereof.

Methods of Administration

According to one embodiment, the active agent corresponding to the ascorbate compound that is selected from the group consisting of ascorbic acid, an ascorbic acid derivative, and/or a pharmaceutically acceptable salt thereof, is administered as a co-therapy or combination therapy with the pentaaza macrocyclic ring complex. Co-therapy or combination therapy according to the methods described herein is intended to embrace administration of each compound in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent, or single or multiple parenteral administrations, or other routes of administration and dosage forms. When administered in combination, therefore, the therapeutic agents (i.e., the pentaaza macrocyclic ring complex and/or the active agent) can be formulated as separate compositions that are administered at the same time or sequentially at different times, or the therapeutic agents can be given as a single composition. Pharmaceutical compositions and formulations are discussed elsewhere herein. Furthermore, while the active agent corresponding to the ascorbate compound is referred to herein as being selected from the group consisting of ascorbic acid, an ascorbic acid derivative, or a pharmaceutically acceptable salt of ascorbic acid or an ascorbic acid derivative, it is noted that all combinations of these are also explicitly included herein. Furthermore, other active agents such as the thioredoxin reductase inhibitor and glutathione-depleting agent described above, can also be administered as a co-therapy or combination therapy with the pentaaza macrocyclic ring complex and ascorbate compound.

It is not necessary that the pentaaza macrocyclic ring complex and the active agent corresponding to the ascorbate compound be administered simultaneously or essentially simultaneously; the agents and compounds may be administered in sequence. The advantage of a simultaneous or essentially simultaneous administration, or sequential administration, is well within the determination of the skilled clinician. For instance, while a pharmaceutical composition or formulation comprising a pentaaza macrocyclic ring complex may be advantageous for administering first in the combination for one particular treatment, prior administration of the active agent corresponding to the ascorbate compound (or prior administration of the pentaaza macrocyclic ring complex) may be advantageous in another treatment. It is also understood that the instant combination of pentaaza macrocyclic ring complex and active agent corresponding to the ascorbate compound may be used in conjunction with other methods of treating cancer (typically cancerous tumors) including, but not limited to, radiation therapy and surgery, or other chemotherapy. It is further understood that another active agent, such as a cytostatic or quiescent agent, or antiemetic agent, if any, or thioredoxin reductase inhibitor or glutathione-depleting agent described above, may be administered sequentially or simultaneously with any or all of the other synergistic therapies.

Thus, embodiments of the therapeutic method include wherein a pentaaza macrocyclic ring complex and an active agent corresponding to the ascorbate compound selected from ascorbic acid, ascorbic acid derivatives, pharmaceutically acceptable salts of ascorbic acid, pharmaceutically acceptable salts of ascorbic acid derivatives, and combinations thereof, are administered simultaneously or sequentially. For instance, the present disclosure encompasses a method for the treatment of cancer wherein a pentaaza macrocyclic ring complex and an active agent corresponding to the ascorbate compound are administered simultaneously or sequentially. Other active agents can also be administered simultaneously or sequentially with the pentaaza macrocyclic ring complex and active agent corresponding to the ascorbate compound.

As noted above, if the pentaaza macrocyclic ring complex and active agent corresponding to the ascorbate compound are not administered simultaneously or essentially simultaneously, then the initial order of administration of the components may be varied.

Thus, for example, a pentaaza macrocyclic ring complex may be administered first, followed by the administration of an active agent (e.g., the ascorbate compound selected from the group consisting of ascorbic acid, and ascorbic acid derivative, and/or a pharmaceutically acceptable salt thereof); or an active agent (e.g., the ascorbate compound) may be administered first, followed by the administration of a pentaaza macrocyclic ring complex. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. By way of another example, the active agent (e.g. the ascorbate compound) may be administered initially (e.g., to increase the production of superoxide). The treatment is then continued with the administration of the pentaaza macrocyclic ring complex (e.g., to produce new to hydrogen peroxide from superoxide), until the treatment protocol is complete. Other sequences of administration to exploit the effects described herein are contemplated, and other sequences of administration of other active agents can also be provided.

In one embodiment, the subject is pre-treated with the pentaaza macrocyclic ring complex (i.e., the pentaaza macrocyclic ring complex is pre-administered), followed by administration of the active agent (e.g., ascorbate compound selected from the group consisting of ascorbic acid, ascorbic acid derivative and/or pharmaceutically acceptable salt thereof), or vice versa. In accordance with such embodiments, the active agent is preferably administered at least 1 hour, but no more than 3 days, after administration of the pentaaza macrocyclic ring complex, or vice versa. For example, in one embodiment, the active agent is administered between 1 hour and 2 days after administration of the pentaaza macrocyclic ring complex, or vice versa. In another embodiment, for example, the active agent is administered between 1 hour and 1 day after administration of the pentaaza macrocyclic ring complex, or vice versa. For example, the active agent may be administered within 1 hour, 2 hours, 3 hours, 4 hours, 5 hours, 6 hours, 12 hours, 18 hours, 24 hours, 36 hours, or 48 hours after administration of the pentaaza macrocyclic ring complex, or vice versa. In one particular embodiment, for example, the active agent is administered within 24 hours after administration of the pentaaza macrocyclic ring complex, or vice versa. In these and other embodiments, the pentaaza macrocyclic ring complex may be administered in multiple doses leading up to administration of the active agent.

Alternatively, the subject may be pre-treated with the active agent (e.g., ascorbate compound), followed by administration of the pentaaza macrocyclic ring complex, or vice versa. In accordance with such embodiments, the pentaaza macrocyclic ring complex is preferably administered within at least 1 plasma half-life of the other active agents, but no more than 4 plasma half-lives of the other active agents, or vice versa. For example, the pentaaza macrocyclic ring complex may be administered within 1, 2, or 3 plasma half-lives of the other active agents, or vice versa.

In other alternative embodiments, the subject may be pre-treated with the pentaaza macrocyclic ring complex, followed by administration of the active agent (e.g., ascorbate compound), which is further followed by an additional administration of the pentaaza macrocyclic ring complex. In accordance with this embodiment, for example, the standard pentaaza macrocyclic ring complex dose may be separated into two (or more) portions, one portion of which is administered prior to administration of the active agent, and the second portion of which is administered after administration of the active agent. This staggered therapy regime could also be employed where the active agents is administered first. In addition, the subject could be pre-treated with a partial or full dose of pentaaza macrocyclic ring complex, followed by administration of a first active agent (e.g., an ascorbate compound), which is then followed by the administration of additional (or partial) dose of penataaza macrocyclic ring complex, which may be further followed by administration of a second active agent (e.g., the same or different ascorbate compound). Further, the subject could be pre-treated with a partial or full dose of pentaaza macrocyclic ring complex, followed by administration of more than one active agent (e.g. more that one ascorbate compound), which is then followed by administration of an additional (or partial) does of pentaaza macrocyclic complex.

As described in further detail below, the combinations of the disclosure may also be co-administered with other well known therapeutic agents that are selected for their particular usefulness against the condition that is being treated. Combinations may alternatively be used sequentially with known pharmaceutically acceptable agent(s) when a multiple combination formulation is inappropriate.

The pentaaza macrocyclic ring complex and active agent (e.g., ascorbate compound) can generally be administered according to therapeutic protocols well known in the art. It will be apparent to those skilled in the art that the administration of the various components can be varied depending on the disease being treated and the effects of pentaaza macrocyclic ring complex and active agent on that disease. Also, in accordance with the knowledge of the skilled clinician, the therapeutic protocols (e.g., dosage amounts and times of administration) can be varied in view of the observed effects of the administered therapeutic agents (i.e., pentaaza macrocyclic ring complex, active agent) on the patient, and in view of the observed responses of the disease to the administered therapeutic agents.

Also, in general, the pentaaza macrocyclic ring complex and active agent (e.g., ascorbate compound) do not have to be administered in the same pharmaceutical composition, and may, because of different physical and chemical characteristics, have to be administered by different routes. For example, the pentaaza macrocyclic ring complex may be administered orally to generate and maintain good blood levels thereof, while the active agent (e.g., ascorbate compound) may be administered intravenously, or vice versa. The determination of the mode of administration and the advisability of administration, where possible, in the same pharmaceutical composition, or in separate pharmaceutical compositions (e.g., two or three separate compositions) is well within the knowledge of the skilled clinician. The initial administration can be made according to established protocols known in the art, and then, based upon the observed effects, the dosage, modes of administration and times of administration can be modified by the skilled clinician.

The particular choice of pentaaza macrocyclic ring complex and active agent (each of which are described in detail herein), and other related therapies (such as chemotherapy or radiation), will depend upon the diagnosis of the attending physicians and their judgment of the condition of the patient and the appropriate treatment protocol.

Thus, in accordance with experience and knowledge, the practicing physician can modify each protocol for the administration of a component (pentaaza macrocyclic ring complex and active agent(s)) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The products of which the combination are composed may be administered simultaneously, separately or spaced out over a period of time so as to obtain the maximum efficacy of the combination; it being possible for each administration to vary in its duration from a rapid administration to a relatively continuous perfusion of either component (in separate formulations or in a single formulation). As a result, for the purposes of the present disclosure, the combinations are not exclusively limited to those which are obtained by physical association of the constituents, but also to those which permit a separate administration, which can be simultaneous or spaced out over a period of time.

Accordingly, administration of the components described herein can occur as a single event or over a time course of treatment. For example, the pentaaza macrocyclic ring complex and one or more active agent(s) (e.g. ascorbate compound) can be administered (simultaneously or in sequence) hourly (e.g., every hour, every two hours, every three hours, every four hours, every five hours, every six hours, and so on), daily, weekly, bi-weekly, or monthly. For treatment of acute conditions, the time course of treatment may be at least several hours or days. Certain conditions could extend treatment from several days to several weeks. For example, treatment could extend over one week, two weeks, or three weeks. For more chronic conditions, treatment could extend from several weeks to several months, a year or more, or the lifetime of the patient in need of such treatment. Alternatively, the compounds and agents can be administered hourly, daily, weekly, bi-weekly, or monthly, for a period of several weeks, months, years, or over the lifetime of the patient as a prophylactic measure.

The dose or amount of pharmaceutical compositions including the pentaaza macrocyclic ring complex and active agent(s) (e.g., ascorbate compound) administered to the patient should be an effective amount for the intended purpose, i.e., treatment or prophylaxis of one or more of the diseases, pathological disorders, and medical conditions discussed herein, particularly cancer. Generally speaking, the effective amount of the composition administered can vary according to a variety of factors such as, for example, the age, weight, sex, diet, route of administration, and the medical condition of the patient in need of the treatment. Specifically preferred doses are discussed more fully below. It will be understood, however, that the total daily usage of the compositions described herein will be decided by the attending physician or veterinarian within the scope of sound medical judgment.

As noted above, the combinations can be co-administered (via a co-formulated dosage form or in separate dosage forms administered at about the same time). The combinations can also be administered separately, at different times, with each agent in a separate unit dosage form. Numerous approaches for administering active agents and pentaaza macrocyclic ring complex are known in the art, and can readily be adapted for use in the present disclosure. The pharmaceutical compositions may be delivered orally, e.g., in a tablet or capsule unit dosage form, or parenterally, e.g., in an injectable unit dosage form, or by some other route. For systemic administration, for example, the drugs can be administered by, for example, intravenous infusion (continuous or bolus). The compositions can be used for any therapeutic or prophylactic treatment where the patient benefits from treatment with the combination.

The specific therapeutically effective dose level for any particular patient will depend upon a variety of factors including the disorder being treated and the severity of the disorder; activity of the specific compound(s) employed; the age, body weight, general health, sex and diet of the patient; the time of administration; the route of administration; the rate of excretion of the specific compound(s) employed; the duration of the treatment; drugs used in combination or coincidental with the specific compound(s) employed and like factors well known in the medical and/or veterinary arts. For example, it is well within the skill of the art to start doses of the compound(s) at levels lower than those required to achieve the desired therapeutic effect and to gradually increase the dosage until the desired effect is achieved. If desired, the effective daily doses may be divided into multiple doses for purposes of administration. Consequently, single dose compositions may contain such amounts or submultiples to make up the daily dose.

In one embodiment, suitable or preferred doses for each of the components are employed in the methods or included in the compositions described herein. Preferred dosages for the pentaaza macrocyclic ring complex, for instance, may be within the range of 10 to 500 mg per patient per day. An example of a typical dose of ascorbate compound, can be a dose of 100 mg/kg body weight to 2000 mg/kg body weight per day. However, the dosage may vary depending on the dosing schedule, which can be adjusted as necessary to achieve the desired therapeutic effect. It should be noted that the ranges of effective doses provided herein are not intended to limit the disclosure and represent exemplary dose ranges. The most preferred dosage will be tailored to the individual subject, taking into account, among other things, the particular combinations employed, and the patient's age, sex, weight, physical condition, diet, etc., as is understood and determinable by one of ordinary skill in the art without undue experimentation.

Treatment of cancer, or cancer therapies, described herein includes achieving a therapeutic benefit and/or a prophylactic benefit. Therapeutic benefits generally refer to at least a partial eradication or amelioration of the underlying disorder being treated. For example, in a cancer patient, therapeutic benefit includes (partial or complete) eradication or amelioration of the underlying cancer. Also, a therapeutic benefit is achieved with at least partial, or complete, eradication or amelioration of one or more of the physiological symptoms associated with the underlying disorder such that an improvement is observed in the patient, notwithstanding the fact that the patient may still be afflicted with the underlying disorder. For prophylactic benefit, a method of the disclosure may be performed on, or a composition of the invention administered to, a patient at risk of developing cancer, or to a patient reporting one or more of the physiological symptoms of such conditions, even though a diagnosis of the condition may not have been made.

Cancer Treatment Methods

In general, any subject having, or suspected of having, a cancer or other proliferative disorder may be treated using the compositions and methods of the present disclosure. Subjects receiving treatment according to the methods described herein are mammalian subjects, and typically human patients. Other mammals that may be treated according to the present disclosure include companion animals such as dogs and cats, farm animals such as cows, horses, and swine, as well as birds and more exotic animals (e.g., those found in zoos or nature preserves). In one embodiment of the disclosure, a method is provided for the treatment of cancerous tumors, particularly solid tumors. Advantageously, the methods described herein may reduce the development of tumors, reduce tumor burden, or produce tumor regression in a mammalian host. Cancer patients and individuals desiring cancer prophylaxis can be treated with the combinations described herein.

Cancer and tumors generally refer to or describe the physiological condition in mammals that is typically characterized by unregulated cell growth. By means of the pharmaceutical combinations, co-formulations, and combination therapies of the present disclosure, various tumors can be treated such as tumors of the breast, heart, lung, small intestine, colon, spleen, kidney, bladder, head and neck, ovary, prostate, brain, pancreas, skin, bone, bone marrow, blood, thymus, uterus, testicles, cervix, and liver.

In one embodiment, the tumor or cancer is chosen from adenoma, angio-sarcoma, astrocytoma, epithelial carcinoma, germ inoma, glioblastoma, glioma, hamartoma, hemangioendothelioma, hemangiosarcoma, hematoma, hepato-blastoma, leukemia, lymphoma, medulloblastoma, melanoma, neuroblastoma, osteosarcoma, retinoblastoma, rhabdomyosarcoma, sarcoma, and teratoma. The tumor can be chosen from acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic, papillary serous adeno-carcinoma, pineal cell, pituitary tumors, plasmacytoma, pseudo-sarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor.

Thus, for example, the present disclosure provides methods for the treatment of a variety of cancers, including, but not limited to, the following: carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma); hematopoietic tumors of lymphoid lineage including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma; hematopoietic tumors of myeloid lineage including acute and chronic myelogenous leukemias, myelodysplastic syndrome, myeloid leukemia, and promyelocytic leukemia; tumors of the central and peripheral nervous system including astrocytoma, neuroblastoma, glioma, and schwannomas; tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

For example, particular leukemias that can be treated with the combinations and methods described herein include, but are not limited to, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

Lymphomas can also be treated with the combinations and methods described herein. Lymphomas are generally neoplastic transformations of cells that reside primarily in lymphoid tissue. Lymphomas are tumors of the immune system and generally are present as both T cell- and as B cell-associated disease. Among lymphomas, there are two major distinct groups: non-Hodgkin's lymphoma (NHL) and Hodgkin's disease. Bone marrow, lymph nodes, spleen and circulating cells, among others, may be involved. Treatment protocols include removal of bone marrow from the patient and purging it of tumor cells, often using antibodies directed against antigens present on the tumor cell type, followed by storage. The patient is then given a toxic dose of radiation or chemotherapy and the purged bone marrow is then re-infused in order to repopulate the patient's hematopoietic system.

Other hematological malignancies that can be treated with the combinations and methods described herein include myelodysplastic syndromes (MDS), myeloproliferative syndromes (MPS) and myelomas, such as solitary myeloma and multiple myeloma. Multiple myeloma (also called plasma cell myeloma) involves the skeletal system and is characterized by multiple tumorous masses of neoplastic plasma cells scattered throughout that system. It may also spread to lymph nodes and other sites such as the skin. Solitary myeloma involves solitary lesions that tend to occur in the same locations as multiple myeloma.

In one embodiment, the methods and pharmaceutical compositions described herein are used to treat a cancer that is any of breast cancer, oral squamous cell carcinoma, lung cancer including non-small cell lung cancer, renal cell carcinoma, spindle cell carcinoma, colorectal cancer, head and neck squamous cell carcinoma, and pancreatic cancer. In yet another embodiment, the methods and pharmaceutical compositions described herein are used to treat a cancer that is any of head and neck cancer and lung cancer.

Pharmaceutical Formulations

Another aspect of the present disclosure relates to the pharmaceutical compositions comprising the combinations described herein, together with a pharmaceutically acceptable excipient. The pharmaceutical compositions include the pentaaza macrocyclic ring complex (e.g., those corresponding to Formula (I)), and at least one active agent corresponding to an ascorbate compound selected from ascorbic acid, an ascorbic acid derivative, a pharmaceutically acceptable salt of ascorbic acid, a pharmaceutically acceptable salt of an ascorbic acid derivative, and combinations thereof, as discussed above, typically formulated as a pharmaceutical dosage form, optionally in combination with a pharmaceutically acceptable carrier, additive or excipient. In one embodiment, for example, the pharmaceutical composition comprises a pentaaza macrocyclic ring complex, ascorbic acid, and a pharmaceutically acceptable excipient. In another embodiment, the pharmaceutical composition comprises a pentaaza macrocyclic ring complex, an ascorbic acid derivative, and a pharmaceutically acceptable excipient. In yet another embodiment, the pharmaceutical composition comprises a pentaaza macrocyclic ring complex, a pharmaceutically acceptable salt of ascorbic acid, and a pharmaceutically acceptable excipient. In yet another embodiment, the pharmaceutical composition comprises a pentaaza macrocyclic ring complex, a pharmaceutically acceptable salt of an ascorbic acid derivative, and a pharmaceutically acceptable excipient. The pharmaceutical composition can also comprise one or more of a thioredoxin reductase inhibitor and a glutathione depleting agent in combination with the pentaaza macrocyclic ring complex and ascorbate compound. Pharmaceutical compositions according to the present disclosure may be used in the treatment of cancer.

The pharmaceutical compositions described herein are products that result from the mixing or combining of more than one active ingredient and includes both fixed and non-fixed combinations of the active ingredients. Fixed combinations are those in which the active ingredients, e.g., a pentaaza macrocyclic ring complex and an active agent corresponding to an ascorbate compound selected from the group consisting of ascorbic acid, an ascorbic acid derivative, and/or a pharmaceutically acceptable salt thereof, are administered to a patient simultaneously in the form of a single entity or dosage. Other active agents such as the thioredoxin reductase inhibitor and glutathione-depleting agent may also be administered as a part of the single entity or dosage, or may be separately administered Non-fixed combinations are those in which the active ingredients, e.g., a pentaaza macrocyclic ring complex and an ascorbate compound, optionally with a thioredoxin reductase inhibitor, and/or a glutathione depleting agent described herein, are administered to a patient as separate entities either simultaneously, concurrently or sequentially with no specific intervening time limits, wherein such administration provides effective levels of the compounds in the body of the patient. The latter also applies to cocktail therapy, e.g., the administration of three or more active ingredients.

The above-described pentaaza macrocyclic ring complex and active agent(s) (e.g., ascorbate compound) may be dispersed in a pharmaceutically acceptable carrier prior to administration to the mammal; i.e., the components described herein are preferably co-formulated. The carrier, also known in the art as an excipient, vehicle, auxiliary, adjuvant, or diluent, is typically a substance which is pharmaceutically inert, confers a suitable consistency or form to the composition, and does not diminish the efficacy of the compound. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the compositions of the described herein can be formulated for any route of administration so long as the blood circulation system is available via that route, and in accordance with the conventional route of administration. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in combination with the compositions of the present disclosure are well known to those of ordinary skill in the art and are selected based upon a number of factors: the particular compound(s) and agent(s) used, and its/their concentration, stability and intended bioavailability; the subject, its age, size and general condition; and the route of administration. Suitable non-aqueous, pharmaceutically-acceptable polar solvents include, but are not limited to, alcohols (e.g., a-glycerol formal, 6-glycerol formal, 1,3-butyleneglycol, aliphatic or aromatic alcohols having 2 to 30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(6-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di-, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di-, or tri-glycerides, fatty acid esters such as isopropyl myristate, fatty acid derived PEG esters such as PEG-hydroxyoleate and PEG-hydroxystearate, N-methyl pyrrolidinone, pluronic 60, polyoxyethylene sorbitol oleic polyester, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, DE, polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $O_4$ to $O_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2 to 30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3 to 30 carbon atoms (e.g., acetone, methyl ethyl ketone, methyl isobutyl ketone); aliphatic, cycloaliphatic or aromatic hydrocarbons having 4 to 30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, di methylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1 to 30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

In some embodiments, oils or non-aqueous solvents may be employed in the formulations, e.g., to bring one or more of the compounds into solution, due to, for example, the presence of large lipophilic moieties. Alternatively, emulsions, suspensions, or other preparations, for example, liposomal preparations, may be used. With respect to liposomal preparations, for example, any known methods for preparing liposomes may be used. See, for example, Bangham et al., J. Mol. Biol, 23: 238-252 (1965) and Szoka et al., Proc. Natl Acad. Sci 75: 4194-4198 (1978), incorporated herein by reference. Thus, in one embodiment, one or more of the compounds are administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines. Ligands may also be attached to the liposomes, for instance, to direct these compositions to particular sites of action.

Other pharmaceutically acceptable solvents for use in the pharmaceutical compositions described herein are well known to those of ordinary skill in the art, and are identified in The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics, (G. Banker et al., eds., 3d ed.) (Marcel Dekker, Inc., New York, New York, 1995), The Pharmacological Basis of Therapeutics, (Goodman & Gilman, McGraw Hill Publishing), Pharmaceutical Dosage Forms, (H. Lieberman et al., eds.) (Marcel Dekker, Inc., New York, New York, 1980), Remington's Pharmaceutical Sciences (A. Gennaro, ed., 19th ed.) (Mack Publishing, Easton, PA, 1995), The United States Pharmacopeia 24, The National Formulary 19, (National Publishing, Philadelphia, PA, 2000), and A. J. Spiegel et al., Use of Nonaqueous Solvents in Parenteral Products, Journal of Pharmaceutical Sciences, Vol. 52, No. 10, pp. 917-927 (1963).

Formulations containing the pentaaza macrocyclic ring complex and active agent(s) (e.g., ascorbate compound) may take the form of solid, semi-solid, lyophilized powder, or liquid dosage forms such as, for instance, aerosols, capsules, creams, emulsions, foams, gels/jellies, lotions, ointments, pastes, powders, soaps, solutions, sprays, suppositories, suspensions, sustained-release formulations, tablets, tinctures, transdermal patches, and the like, preferably in unit dosage forms suitable for simple administration of precise dosages. If formulated as a fixed dose, such pharmaceutical compositions or formulation products employ the pentaaza macrocyclic ring complex and active agent(s) within accepted dosage ranges.

In one embodiment, a formulation is provided that contains the ascorbate compound as a part of liquid dosage form, such as a sterile liquid dosage form suitable for injection. For example, the liquid form containing the ascorbate compound can comprise ascorbic acid in combination with one or more further ingredients, such as edetate disodium (EDTA). In one embodiment, the liquid form can comprise EDTA in an amount suitable to act as a preservative and/or metal-chelating agent, such as an amount of about 0.025%. The liquid form can further comprise water, and may also comprise a pH adjuster, such as sodium bicarbonate, for pH adjustment in the range of pH 5.5 to 7.0. An example of a suitable liquid form for the administration of the ascorbate compound is the ascorbic acid injection composition Ascor L 500 available from McGuff Pharmaceuticals Inc. In one embodiment, the pentaaza macrocylic ring complex can also be provided as a part of a sterile liquid dosage form suitable for injection, either in the same liquid dosage form with the ascorbate compound or as a separate dosage form.

Formulations for certain pentaaza macrocyclic ring complexes are also described in, for example, in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041 (each of which is hereby incorporated herein by reference in its entirety).

It is contemplated that co-formulations of the pentaaza macrocyclic ring complex and active agent(s) (e.g., ascorbate compound) may employ conventional formulation techniques for these components individually, or alternative formulation routes, subject to compatibility and efficacy of the various components, in combination.

The above-described pharmaceutical compositions including the pentaaza macrocyclic compound and active agent(s) (e.g., ascorbate compound) may additionally include one or more additional pharmaceutically active components. Suitable pharmaceutically active agents that may be included in the compositions of the present invention include, for instance, antiemetics, anesthetics, antihypertensives, antianxiety agents, anticlotting agents, anticonvulsants, blood glucose-lowering agents, decongestants, antihistamines, antitussives, antineoplastics, beta blockers, antiinflammatory agents, antipsychotic agents, cognitive enhancers, cholesterol-reducing agents, antiobesity agents, autoimmune disorder agents, anti-impotence agents, antibacterial and antifungal agents, hypnotic agents, anti-Parkinsonism agents, anti-Alzheimer's Disease agents, antibiotics, anti-depressants, and antiviral agents. The individual components of such combinations may be administered either sequentially or simultaneously in separate or combined pharmaceutical formulations.

Combination Treatment with Cancer Therapy

In one embodiment, the pentaaza macrocyclic ring complex and active agent(s) (e.g., ascorbate compound selected from the group consisting of ascorbic acid, an ascorbic acid derivative, and/or a pharmaceutically acceptable salt thereof) can be administered in combination with another cancer therapy, to provide therapeutic treatment. For example, the pentaaza macrocyclic ring complex and active agent(s) may be administered as a part of at least one of a chemotherapy treatment and radiation therapy.

In general, the temporal aspects of the administration of the pentaaza macrocyclic ring complex and active agent(s) (e.g., ascorbate compound) may depend for example, on the particular compound, radiation therapy, or chemotherapy that is selected, or the type, nature, and/or duration of the radiation exposure. Other considerations may include the disease or disorder being treated and the severity of the disease or disorder; activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors. For example, the compounds may be administered in various embodiments before, during, and/or after the administration of the cancer therapy (e.g., radiation therapy or chemotherapy). By way of another example, the compounds may be administered in various embodiments before, during, and/or after an exposure to radiation.

If desired, the effective dose can be divided into multiple doses for purposes of administration; consequently, single dose compositions may contain such amounts or submultiples thereof to make up the dose.

In one embodiment, for example, the pentaaza macrocyclic ring complex and active agent(s) (e.g., ascorbate compound) are administered to the patient prior to or simultaneous with the cancer therapy. In another embodiment, for example, the pentaaza macrocyclic ring complex and active agent(s) (e.g., ascorbate compound) are administered to the patient prior to, but not after, the cancer therapy. In yet another embodiment, the pentaaza macrocyclic ring complex and active agent(s) are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the cancer therapy. In still other embodiments, for example, the pentaaza macrocyclic ring complex and active agent(s) are administered to the patient after the cancer therapy; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the cancer treatment.

In another embodiment, for example, the pentaaza macrocyclic ring complex and active agent(s) (e.g., ascorbate compound) are administered to the patient prior to or simultaneous with the radiation exposure. In another embodiment, for example, the compounds are administered to the patient prior to, but not after, the radiation exposure. In yet another embodiment, the pentaaza macrocyclic ring complex and active agent(s) are administered to the patient at least 15 minutes, 30 minutes, 45 minutes, 60 minutes, 90 minutes, 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, prior to the radiation exposure. In still other embodiments, for example, pentaaza macrocyclic ring complex and active agent(s) are administered to the patient after the radiation exposure; thus, for example, the compound may be administered up to 15 minutes, 30 minutes, 45 minutes, 60 minutes, 90 minutes, or 180 minutes, 0.5 days, 1 day, 3 days, 5 days, one week, two weeks, three weeks, four weeks, five weeks, six weeks, seven weeks, eight weeks, nine weeks, ten weeks, eleven weeks, twelve weeks, or longer, after the radiation exposure.

In one embodiment, the pentaaza macrocyclic ring complex and active agent(s) (e.g., ascorbate compound) are administered as a part of a course of therapy that includes the radiation therapy. In radiation therapy, a patient receives a dose of ionizing radiation to kill or control the growth of cancerous cells. The dose of radiation may be directed at a specific part of the body, and the beam of radiation may also be shaped according to a predetermined treatment regimen, to reduce deleterious effects on parts of the body not afflicted with cancer. A typical course of radiation therapy may include one or a plurality of doses of radiation, which can be administered over the course of days, weeks and even months. As is discussed in more detail in the Examples section below, the administration of pentaaza macrocyclic ring complex with the active agent(s) demonstrates unexpected synergistic effects in sensitizing cancer cells to radiation therapy, thereby improving the efficacy of radiation treatment.

In one embodiment, at least one of the pentaaza macrocyclic ring complex and active agent(s) (e.g., ascorbate compound) are administered within a predetermined time period before or after a radiation dose is administered. For example, the pentaaza macrocyclic ring complex and active agent(s) may be administered within 1 week, 48 hours, 24 hours, 12 hours, 6, hours, 2 hours, 1 hour or even within 30 minutes of the patient receiving the radiation dose (either before or after the radiation dose). Other durations between the radiation dose and administration of the compound that result in the enhanced the killing of cancer cells may also be suitable. In one embodiment, one or more of the pentaaza macrocyclic ring complex and active agent(s) (e.g., ascorbate compound) may be administered before the radiation dose, and the remaining one or more of the pentaaza macrocyclic ring complex and active agent(s) can be administered after the dose. One or more of the pentaaza macrocyclic ring complex and active agent(s) may also be administered both before and after administration of a radiation dose.

In one embodiment, a course of radiation therapy includes a plurality of radiation doses given over a predetermined period of time, such as over the course of hours, weeks, days and even months, with the plural doses being either of the same magnitude or varying. That is, course of radiation therapy can comprise the administration of a series of multiple doses of radiation. In one embodiment, pentaaza macrocyclic ring complex and the active agent(s) (e.g. ascorbate compound) can be administered before one or more radiation dose in the series, such as before each radiation dose, or before some fraction of the radiation doses. Furthermore, the administration of the pentaaza macrocyclic ring complex and active agent(s) during the course of radiation therapy can be selected to enhance the cancer treating effects of the radiation therapy, such as by sensitizing cancer cells to the radiation therapy. In one embodiment, the pentaaza macrocyclic ring complex and active agent(s) are administered within a predetermined duration before or after of each dose, such as the predetermined duration discussed above. In another embodiment, the pentaaza macrocyclic ring complex and active agent(s) are administered within a predetermined duration of time before or after only select doses. In yet another embodiment, at least one of the pentaaza macrocyclic ring complex and active agent(s) is administered within a predetermined duration of time before the doses, while another of the pentaaza macrocyclic ring complex and active agent(s) is administered within a predetermined duration of time after the doses. In a further embodiment, at least one of the pentaaza macrocyclic ring complex and active agent(s) is administered only within the predetermined duration before or after select doses, while another of the pentaaza macrocyclic ring complex and active agent(s) is administered only within the predetermined duration before or after doses other than the select doses.

In yet another embodiment, the pentaaza macrocyclic ring complex and active agent(s) (e.g., ascorbate compound) are administered as a part of a course of therapy that includes chemotherapy. In chemotherapy, chemotherapeutic agents are administered to a patient to kill or control the growth of cancerous cells. A typical course of chemotherapy may include one or a plurality of doses of one or more chemotherapeutic agents, which can be administered over the course of days, weeks and even months. Chemotherapeutic agents can include at least one of: alkylating antineoplastic agents such as nitrogen mustards (e.g. cyclophosphamide, chlorambucil), nitrosoureas (e.g. n-nitroso-n-methylurea, carmustine, semustine), tetrazines (e.g. dacarbazine, mitozolimide), aziridines (e.g. thiotepa, mytomycin), platinum-based antineoplastic agents (platinates) (e.g. cisplatin, carboplatin, oxaliplatin, neoplatin, platamin); anti-metabolites such as anti-folates (e.g. methotrexate and pemetrexed), fluoropyrimidines (e.g., fluorouracil, capecitabine), anthracyclines (e.g. doxorubicin, daunorubicin, epirubicin), deoxynucleoside analogs (e.g. cytarabine, gemcitabine, decitabine) and thiopurines (e.g., thioguanine, mercaptopurine); anti microtubule agents such as taxanes (e.g. paclitaxel, docetaxel); topoisomerase inhibitors (e.g. etoposide, doxorubicin, mitoxantrone, teniposide); and antitumor antibiotics (e.g. bleomycin, mitomycin). For example, the chemotherapeutic agent may be selected from the group consisting of all-trans retinoic acid, arsenic trioxide, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine. The administration of many of the chemotherapeutic agents is described in the "Physicians' Desk Reference" (PDR), e.g., 1996 edition (Medical Economics Company, Montvale, N.J. 07645-1742, USA).

In one preferred embodiment, the pentaaza macrocyclic ring complex and the active agent(s) (e.g., ascorbate compound) are administered as a part of a course of therapy that includes a chemotherapeutic agent selected from the group consisting of cisplatin, doxorubicin, bleomycin, and paclitaxel. Without being limited to any particular theory, it is believed that cisplatin, doxorubicin, bleomycin, and paclitaxel may contribute to the generation of superoxide radicals in cells, thereby leading when combined with a manganese pentaaza macrocyclic ring complex to increased oxidative stress and cytotoxicity of the cancer cells. Furthermore, in one embodiment, the chemotherapeutic agent may be selected from the group consisting of a platinum-based antineoplastic agents, a taxane, an anticancer antibiotic, and an anthracycline, which categories of chemotherapeutic agents, without being limited to any particular theory or mechanism, may also be effective in providing chemotherapeutic activity at least in part due to generation of superoxide radicals in cells. Other chemotherapeutic agents that may increase superoxide levels can include arsenic trioxide and 5-FU, which agents can also be used in the methods and compositions described herein. (Alexandre et al., *Cancer Res.* 67: (8), 3512-3517 (2007); Yen et al., *J. Clin. Invest.* 98 (5), 1253-1260 (1996); Masuda et al., *Cancer Chemother. Pharmacol.* 47(2), 155-160 (2001)).

According to yet another embodiment, a chemotherapeutic agent can include at least one of an antimetabolite anti-cancer agents and antimitotic anti-cancer agents, and combinations thereof, which may include some of the agents described above and well as other agents described further herein. Various antimetabolite and antimitotic agents may be employed in the methods and compositions described herein.

Antimetabolic agents typically structurally resemble natural metabolites, which are involved in normal metabolic processes of cancer cells such as the synthesis of nucleic acids and proteins. The antimetabolites, however, differ enough from the natural metabolites such that they interfere with the metabolic processes of cancer cells. In the cell, antimetabolites are mistaken for the metabolites they resemble, and are processed by the cell in a manner analogous to the normal compounds. The presence of the "decoy" metabolites prevents the cells from carrying out vital functions and the cells are unable to grow and survive. For example, antimetabolites may exert cytotoxic activity by substituting these fraudulent nucleotides into cellular DNA, thereby disrupting cellular division, or by inhibition of critical cellular enzymes, which prevents replication of DNA.

In one embodiment, therefore, the antimetabolite agent is a nucleotide or a nucleotide analog. In certain embodiments, for example, the antimetabolite agent may comprise purine (e.g., guanine or adenosine) or analogs thereof, or pyrimidine (cytidine or thymidine) or analogs thereof, with or without an attached sugar moiety.

Suitable antimetabolite agents for use in the present disclosure may be generally classified according to the metabolic process they affect, and can include, but are not limited to, analogues and derivatives of folic acid, pyrimidines, purines, and cytidine. Thus, in one embodiment, the antimetabolite agent(s) is selected from the group consisting of cytidine analogs, folic acid analogs, purine analogs, pyrimidine analogs, and combinations thereof.

In one particular embodiment, for example, the antimetabolite agent is a cytidine analog. According to this embodiment, for example, the cytidine analog may be selected from the group consisting of cytarabine (cytosine arabinodside), azacitidine (5-azacytidine), and salts, analogs, and derivatives thereof.

In another particular embodiment, for example, the antimetabolite agent is a folic acid analog. Folic acid analogs or antifolates generally function by inhibiting dihydrofolate reductase (DHFR), an enzyme involved in the formation of nucleotides; when this enzyme is blocked, nucleotides are not formed, disrupting DNA replication and cell division. According to certain embodiments, for example, the folic acid analog may be selected from the group consisting of denopterin, methotrexate (amethopterin), pemetrexed, pteropterin, raltitrexed, trimetrexate, and salts, analogs, and derivatives thereof.

In another particular embodiment, for example, the antimetabolite agent is a purine analog. Purine-based antimetabolite agents function by inhibiting DNA synthesis, for example, by interfering with the production of purine containing nucleotides, adenine and guanine which halts DNA synthesis and thereby cell division. Purine analogs can also be incorporated into the DNA molecule itself during DNA synthesis, which can interfere with cell division. According to certain embodiments, for example, the purine analog may be selected from the group consisting of acyclovir, allopurinol, 2-aminoadenosine, arabinosyl adenine (ara-A), azacitidine, azathiprine, 8-aza-adenosine, 8-fluoro-adenosine, 8-methoxy-adenosine, 8-oxo-adenosine, cladribine, deoxycoformycin, fludarabine, gancylovir, 8-aza-guanosine, 8-fluoro-guanosine, 8-methoxy-guanosine, 8-oxo-guanosine, guanosine diphosphate, guanosine diphosphate-beta-L-2-am inofucose, guanosine diphosphate-D-arabinose, guanosine diphosphate-2-fluorofucose, guanosine diphosphate fucose, mercaptopurine (6-MP), pentostatin, thiamiprine, thioguanine (6-TG), and salts, analogs, and derivatives thereof.

In yet another particular embodiment, for example, the antimetabolite agent is a pyrimidine analog. Similar to the purine analogs discussed above, pyrimidine-based antimetabolite agents block the synthesis of pyrimidine-containing nucleotides (cytosine and thymine in DNA; cytosine and uracil in RNA). By acting as "decoys," the pyrimidine-based compounds can prevent the production of nucleotides, and/or can be incorporated into a growing DNA chain and lead to its termination. According to certain embodiments, for example, the pyrimidine analog may be selected from the group consisting of ancitabine, azacitidine, 6-azauridine, bromouracil (e.g., 5-bromouracil), capecitabine, carmofur, chlorouracil (e.g. 5-chlorouracil), cytarabine (cytosine arabinoside), cytosine, dideoxyuridine, 3'-azido-3'-deoxythymidine, 3'-dideoxycytidin-2'-ene, 3'-deoxy-3'-deoxythymidin-2'-ene, dihydrouracil, doxifluridine, enocitabine, floxuridine, 5-fluorocytosine, 2-fluorodeoxycytidine, 3-fluoro-3'-deoxythymidine, fluorouracil (e.g., 5-fluorouracil (also known as 5-FU), gemcitabine, 5-methylcytosine, 5-propynylcytosine, 5-propynylthymine, 5-propynyluracil, thymine, uracil, uridine, and salts, analogs, and derivatives thereof. In one embodiment, the pyrimidine analog is other than 5-fluorouracil. In another embodiment, the pyrimidine analog is gemcitabine or a salt thereof.

In certain embodiments, the antimetabolite agent is selected from the group consisting of 5-fluorouracil, capecitabine, 6-mercaptopurine, methotrexate, gemcitabine, cytarabine, fludarabine, pemetrexed, and salts, analogs, derivatives, and combinations thereof. In other embodiments, the antimetabolite agent is selected from the group consisting of capecitabine, 6-mercaptopurine, methotrexate, gemcitabine, cytarabine, fludarabine, pemetrexed, and salts, analogs, derivatives, and combinations thereof. In one particular embodiment, the antimetabolite agent is other than 5-fluorouracil. In a particularly preferred embodiment, the antimetabolite agent is gemcitabine or a salt or thereof (e.g., gemcitabine HCl (Gemzar®)).

Other antimetabolite agents may be selected from, but are not limited to, the group consisting of acanthifolic acid, aminothiadiazole, brequinar sodium, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, Wellcome EHNA, Merck & Co. EX-015, fazarabine, fludarabine phosphate, N-(2'-furanidyl)-5-fluorouracil, Daiichi Seiyaku FO-152, 5-FU-fibrinogen, isopropyl pyrrolizine, Lilly LY-188011; Lilly LY-264618, methobenzaprim, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, tiazofurin, Erbamont TIF, tyrosine kinase inhibitors, Taiho UFT and uricytin, among others.

In one embodiment, the chemotherapeutic agent comprises an antimitotic agent that is a microtubule inhibitor or a mictrotubule stabilizer. In general, microtubule stabilizers, such as taxanes (some of which are also described above) and epothilones, bind to the interior surface of the beta-microtubule chain and enhance microtubule assembly by promoting the nucleation and elongation phases of the polymerization reaction and by reducing the critical tubulin subunit concentration required for microtubules to assemble. Unlike mictrotubule inhibitors, such as the vinca alkaloids, which prevent microtubule assembly, the microtubule stabilizers, such as taxanes, decrease the lag time and dramatically shift the dynamic equilibrium between tubulin dimers and microtubule polymers towards polymerization. In one embodiment, therefore, the microtubule stabilizer is a taxane or an epothilone. In another embodiment, the microtubule inhibitor is a vinca alkaloid.

One element of the therapy described herein includes the use of a taxane or derivative or analog thereof, some of which have also been discussed above. In one embodiment, the taxane may be a naturally derived compound or a related form, or may be a chemically synthesized compound or a derivative thereof, with antineoplastic properties. The taxanes are a family of terpenes, including, but not limited to paclitaxel (Taxol®) and docetaxel (Taxotere®), which are derived primarily from the Pacific yew tree, *Taxus brevifolia*, and which have activity against certain tumors, particularly breast and ovarian tumors. In one embodiment, the taxane is docetaxel or paclitaxel. Paclitaxel is a preferred taxane and is considered an antimitotic agent that promotes the assembly of microtubules from tubulin dimers and stabilizes microtubules by preventing depolymerization. This stability results in the inhibition of the normal dynamic reorganization of the microtubule network that is essential for vital interphase and mitotic cellular functions.

Also included are a variety of known taxane derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; deoxygenated paclitaxel compounds such as those described in U.S. Pat. No. 5,440,056; and taxol derivatives described in U.S. Pat. No. 5,415,869. As noted above, it further includes prodrugs of paclitaxel including, but not limited to, those described in WO 98/58927; WO 98/13059; and U.S. Pat. No. 5,824,701. The taxane may also be a taxane conjugate such as, for example, paclitaxel-PEG, paclitaxel-dextran, paclitaxel-xylose, docetaxel-PEG, docetaxel-dextran, docetaxel-xylose, and the like. Other derivatives are mentioned in "Synthesis and Anticancer Activity of Taxol Derivatives," D. G. I. Kingston et al., Studies in Organic Chemistry, vol. 26, entitled "New Trends in Natural Products Chemistry" (1986), Atta-ur-Rabman, P. W. le Quesne, Eds. (Elsevier, Amsterdam 1986), among other references. Each of these references is hereby incorporated by reference herein in its entirety.

Various taxanes may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267) (each of which is hereby incorporated by reference herein in its entirety), or obtained from a variety of commercial sources, including for example, Sigma-Aldrich Co., St. Louis, MO.

Alternatively, the antimitotic agent can be a microtubule inhibitor; in one preferred embodiment, the microtubule inhibitor is a vinca alkaloid. In general, the vinca alkaloids are mitotic spindle poisons. The vinca alkaloid agents act during mitosis when chromosomes are split and begin to migrate along the tubules of the mitosis spindle towards one of its poles, prior to cell separation. Under the action of these spindle poisons, the spindle becomes disorganized by the dispersion of chromosomes during mitosis, affecting cellular reproduction. According to certain embodiments, for example, the vinca alkaloid is selected from the group consisting of vinblastine, vincristine, vindesine, vinorelbine, and salts, analogs, and derivatives thereof.

The antimitotic agent can also be an epothilone. In general, members of the epothilone class of compounds stabilize microtubule function according to mechanisms similar to those of the taxanes. Epothilones can also cause cell cycle arrest at the G2-M transition phase, leading to cytotoxicity and eventually apoptosis. Suitable epithiolones include epothilone A, epothilone B, epothilone C, epothilone D, epothilone E, and epothilone F, and salts, analogs, and derivatives thereof. One particular epothilone analog is an epothilone B analog, ixabepilone (Ixempra™).

In certain embodiments, the antimitotic anti-cancer agent is selected from the group consisting of taxanes, epothilones, vinca alkaloids, and salts and combinations thereof. Thus, for example, in one embodiment the antimitotic agent is a taxane. More preferably in this embodiment the antimitotic agent is paclitaxel or docetaxel, still more preferably paclitaxel. In another embodiment, the antimitotic agent is an epothilone (e.g., an epothilone B analog). In another embodiment, the antimitotic agent is a vinca alkaloid.

In one embodiment, at least one of the pentaaza macrocyclic ring complex and the active agent(s) (e.g., ascorbate compound) are administered within a predetermined time period before or after a dose of a chemotherapeutic agent is administered. For example, the pentaaza macrocyclic ring complex and active agent(s) may be administered within 1 week, 48 hours, 24 hours, 12 hours, 6, hours, 2 hours, 1 hour or even within 30 minutes of the patient receiving the dose of chemotherapeutic agent (either before or after the dose of chemotherapeutic agent). Other durations between the chemotherapeutic agent dose and administration of the compound that result in the enhanced the killing of cancer cells may also be suitable. In one embodiment, one or more of the pentaaza macrocyclic ring complex and active agent(s) may be administered before the dose of the chemotherapeutic agent, and the remaining one or more of the pentaaza macrocyclic ring complex and active agent(s) can be administered after the dose of the chemotherapeutic agent. One or more of the pentaaza macrocyclic ring complex and active agent(s) may also be administered both before and after administration of the dose of chemotherapeutic agent.

In one embodiment, a course of chemotherapy includes a singular dose of a chemotherapeutic agent. In another embodiment, a course of chemotherapy includes a plurality of doses of a chemotherapeutic agent given over a predetermined period of time, such as over the course of hours, weeks, days and even months. The plural doses may be either of the same magnitude or varying, and can include doses of the same or different chemotherapeutic agents and/or a combination of chemotherapeutic agents. The administration of the pentaaza macrocyclic ring complex and active agent(s) (e.g., ascorbate compound) during the course of chemotherapy can be selected to enhance the cancer treating effects of the chemotherapy, such as by increasing intracellular levels of hydrogen peroxide to promote oxidative stress in the cancer cells. In one embodiment, the pentaaza macrocyclic ring complex and active agent(s) are administered within a predetermined duration before or after each dose, such as the predetermined duration discussed above. In another embodiment, the pentaaza macrocyclic ring complex and active agent(s) are administered within a predetermined duration of time before or after only select doses. In yet another embodiment, at least one of the pentaaza macrocyclic ring complex and active agent(s) are administered within a predetermined duration of time before the doses, while another of the pentaaza macrocyclic ring complex and active agents are administered within a predetermined duration of time after the doses. In a further embodiment, at least one of the pentaaza macrocyclic ring complex and active agent(s) is administered only within the predetermined duration before or after select doses, while another of the pentaaza macrocyclic ring complex and active agent(s) is administered only within the predetermined duration before or after doses other than the select doses.

In yet another embodiment, at least one of the pentaaza macrocyclic ring complex and active agent(s) (e.g., ascorbate compound) is administered in combination with both a radiation therapy and chemotherapy.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

The "ascorbate" (also "Asc") referred to in the examples herein was supplied from an ascorbic acid solution. In particular, to prepare the ascorbate of the examples, L-ascorbic acid stock solution (having a concentration of approximately 1M) was made in water, with the pH adjusted with 1 M NaOH to pH 7, and the concentration of the resulting solution was confirmed spectrophotometrically. An example of a method for preparing an ascorbic acid solution is described in Buettner, *Journal of Biochemical and Biophysical Methods* 16: (1), 27-40 (1988), which describes a solution of ascorbic acid that is stable at pH 7 in the absence of catalytic metals.

The concentration of the ascorbate (i.e. ascorbic acid) added to the in the Examples, was estimated at 2.5 mM for 10 pmol/cell and 5.0 mM for to 20 pmol/cell, for plates having about 1 million cells, and estimated at 5.0 mM for 10 pmol/cell and 10.0 mM for 20 pmol/cell for plates having 2 million cells (with about 4 mL of media on each plate).

Example 1

The effect of ascorbate was tested in a clonogenic cell survivial assay to determine the effects of the compound alone and in combination with a pentaaza macrocyclic ring complex (GC4419). Non-small cell lung cancer cells (H1299) were exponentially grown in culture for 48 hours. The cells were then treated with 5-20 μM GC4419 for 24 hours, and ascorbate (Asc) for one hour, followed by immediate clonogenic assay. The cells were trypsinized, counted, replated at varying lower densities and incubated. Plates were stained and counted for clonogenic survival assays. The results are shown in FIG. 1. The results show that treatment with ascorbate in combination with 5 μM or 20 μM GC4419 resulted in significant enhancements in cell killing, as compared to acorbate or GC4419 monotherapies.

Example 2

Figure 2:
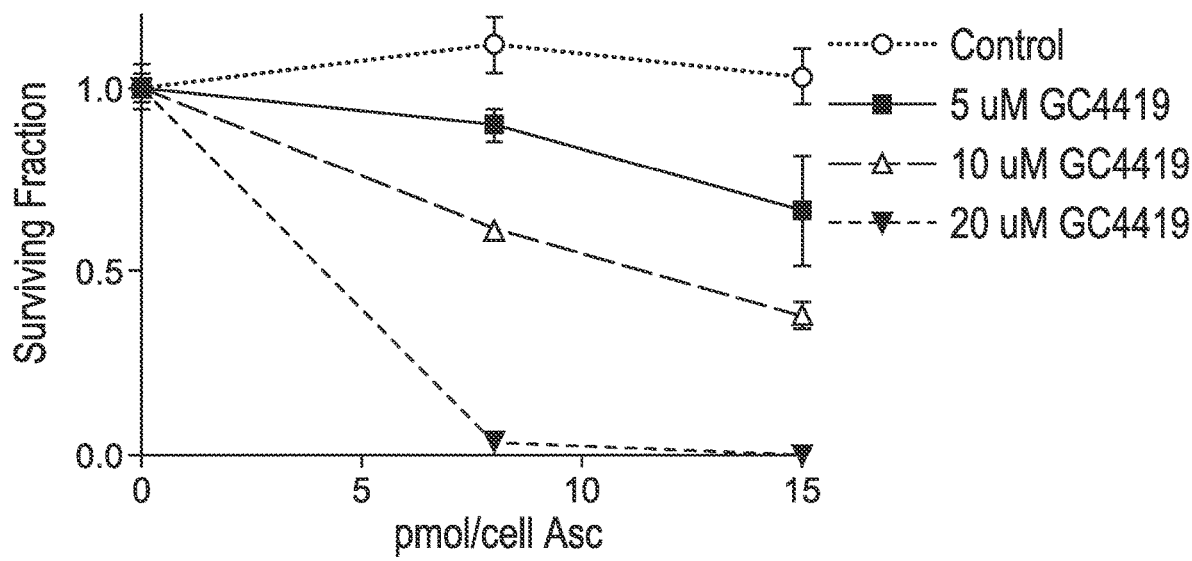
FIG. 2 is a plot showing the surviving fraction of H292 cells for increasing amounts of ascorbate, as determined by a clonogenic cell survivial assay to used determine the effects of the compound alone and in combination with a pentaaza macrocyclic ring complex (GC4419). Lung cancer cells (H292) were exponentially grown in culture for 48 hours. The cells were then treated with 5-20 µM GC4419 for 24 hours, and ascorbate (Asc) for one hour, followed immediately by clonogenic assay. The cells were trypsinized, counted, replated at varying lower densities and incubated. Plates were stained and counted for clonogenic survival assays.

The effect of ascorbate was tested in a clonogenic cell survivial assay to determine the effects of the compound alone and in combination with a pentaaza macrocyclic ring complex (GC4419). Lung cancer cells (H292) were exponentially grown in culture for 48 hours. The cells were then treated with 5-20 μM GC4419 for 24 hours, and ascorbate (Asc) for one hour followed by immediate clonogenic assay. The cells were trypsinized, counted, replated at varying lower densities and incubated. Plates were stained and counted for clonogenic survival assays. The results are shown in FIG. 2. The results show that treatment with ascorbate in combination with 5, 10 or 20 μM GC4419 resulted in significant enhancements in cell killing, as compared to ascorbate or GC4419 monotherapies.

Example 3

Figure 3:
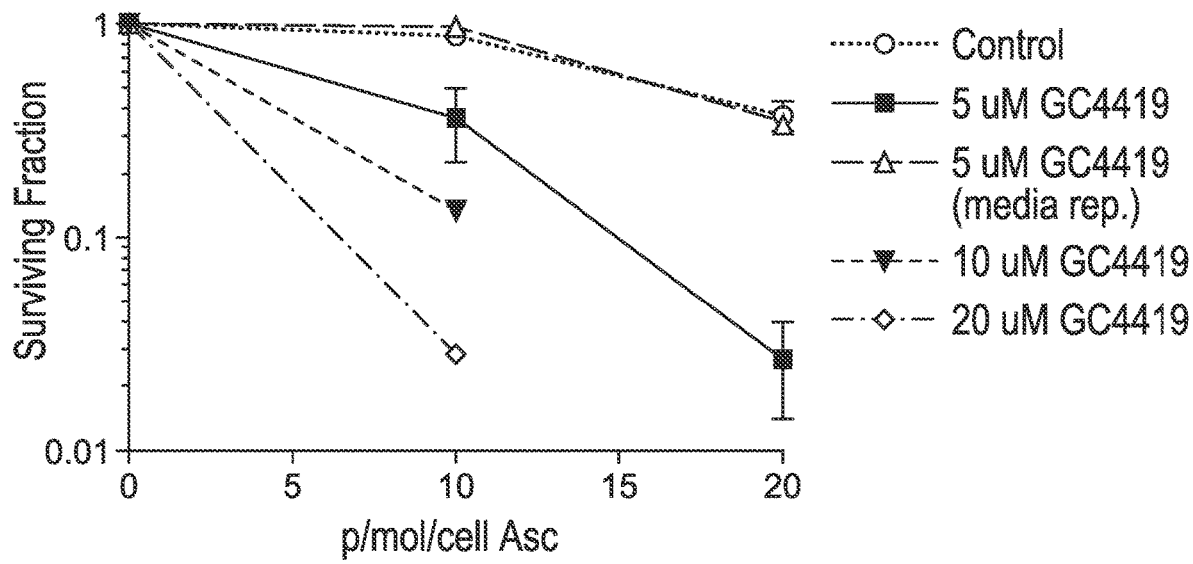
FIG. 3 is a plot showing the surviving fraction of SCC25 cells for increasing amounts of ascorbate, as determined by a clonogenic cell survival assay used to determine the effects of the compound alone and in combination with a pentaaza macrocyclic ring complex (GC4419). Human head and neck squamous cell carcinoma cells (SCC25) were exponentially grown in culture for 24 hours. The cells were then treated with 5-20 µM GC4419 for 24 hours and ascorbate (Asc) for one hour, followed by immediate clonogenic assay. The cells were trypsinized, counted, replated at varying lower densities and incubated. Plates were stained and counted for clonogenic survival assays.

The effect of ascorbate was tested in a clonogenic cell survivial assay to determine the effects of the compound alone and in combination with a pentaaza macrocyclic ring complex (GC4419). Human head and neck squamous cell carcinoma cells (SCC25) were exponentially grown in culture for 24 hours. The cells were then treated with 5-20 μM GC4419 for 24 hours, and ascorbate (Asc) for one hour, followed by immediate clonogenic assay. The cells were trypsinized, counted, replated at varying lower densities and incubated. Plates were stained and counted for clonogenic survival assays. The results are shown in FIG. 3. The results show that treatment with ascorbate in combination with 5, 10 or 20 μM GC4419, when both were present at the same time, resulted in significant enhancements in cell killing, as compared to ascorbate or GC4419 monotherapies, or to sequential treatment with 5 μM GC4419 with complete media replacement between GC4419 and ascorbate-containing culture media.

Example 4

Figure 4:
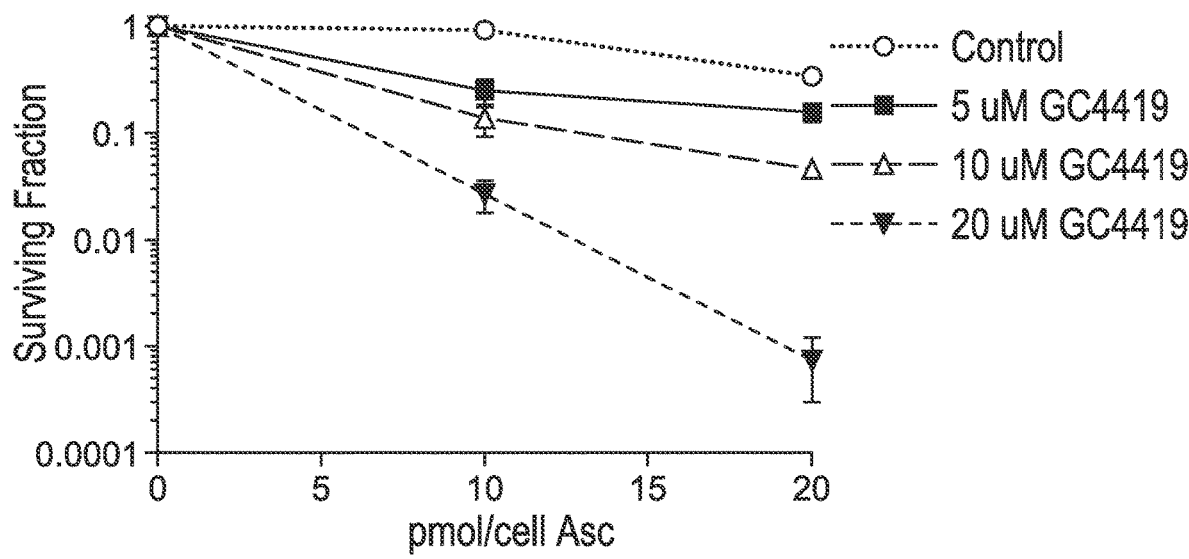
FIG. 4 is a plot showing the surviving fraction of Cal27 cells for increasing amounts of ascorbate, as determined by a clonogenic cell survival assay used to determine the effects of the compound alone and in combination with a pentaaza macrocyclic ring complex (GC4419). Human tongue carcinoma cells (Cal27) were exponentially grown in culture for 48 hours. The cells were then treated with 5-20 µM GC4419 for 24 hours, and ascorbate (Asc) for one hour, followed by immediate clonogenic assay. The cells were trypsinized, counted, replated at varying lower densities and incubated.

The effect of ascorbate was tested in a clonogenic cell survivial assay to determine the effects of the compound alone and in combination with a pentaaza macrocyclic ring complex (GC4419). Human tongue carcinoma cells (Cal27) were exponentially grown in culture for 48 hours. The cells were then treated with 5-20 μM GC4419 for 24 hours, and ascorbate (Asc) for one hour, followed by immediate clonogenic assay. The cells were trypsinized, counted, replated at varying lower densities and incubated. Plates were stained and counted for clonogenic survival assays. The results are shown in FIG. 4. The results show that treatment with ascorbate in combination with 5, 10 or 20 μM GC4419 resulted in significant enhancements in cell killing, as compared to ascorbate or GC4419 monotherapies.

Example 5

Figure 5:
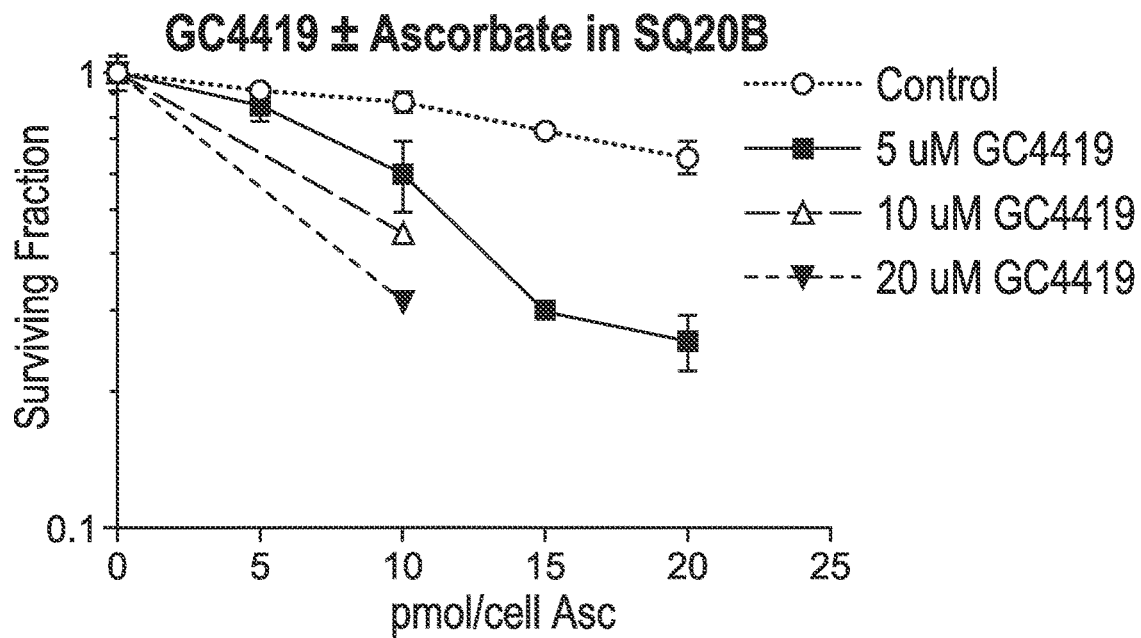
FIG. 5 is a plot showing the surviving fraction of SQ20B cells for increasing amounts of ascorbate, as determined by a clonogenic cell survivial assay used to determine the effects of the compound alone and in combination with a pentaaza macrocyclic ring complex (GC4419). Human head and neck squamous cell carcinoma cells (SQ20B) were exponentially grown in culture for 48 hours. The cells were then treated with 5-20 µM GC4419 for 24 hours, followed by treatment with 5-20 pmol/cell ascorbate for 1 hour. The cells were then trypsinized, counted, replated at varying lower densities and incubated. Plates were stained and counted for clonogenic survival assays.

The effect of ascorbate was tested in a clonogenic cell survivial assay to determine the effects of the compound alone and in combination with a pentaaza macrocyclic ring complex (GC4419). Human head and neck squamous cell carcinoma cells (SQ20B) were exponentially grown in culture for 48 hours. The cells were then treated with 5-20 μM GC4419 for 24 hours, followed by treatment with 5-20 pmol/cell ascorbate for 1 hour. The cells were then trypsinized, counted, replated at varying lower densities and incubated. Plates were stained and counted for clonogenic survival assays. The results are shown in FIG. 5. The results show that treatment with ascorbate in combination with 5, 10 or 20 μM GC4419 increases the cytotoxicity of GC4419 or ascorbate to SQ20B cancer cells.

Example 6

Figure 6:
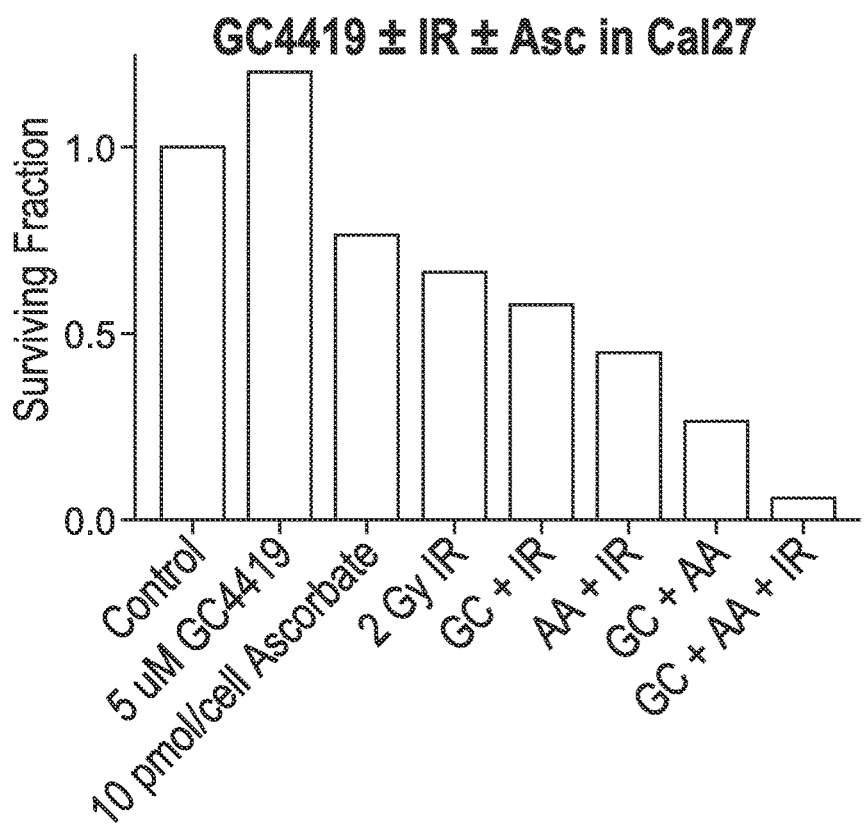
FIG. 6 is a graph showing the surviving fraction of Cal 27 cells treated with ascorbate and combinations with including ascorbate. The effects of ascorbic acid (AA) in combination with a pentaaza macrocyclic ring complex (GC4419) was tested in a clonogenic cell survival assay to determine the effects of the combination alone and when paired with ionizing radiation. Human tongue carcinoma cells (Cal27) were exponentially grown in culture for 48 hours. The cells were then treated with 5 µM GC4419 for 3 hours and 10 pmol/cell ascorbate for 1 hour, either alone, in combination (GC+AA), and/or paired with a dose of ionizing radiation (2 Gy). After the ionizing radiation dose, the cells were trypsinized, counted, replated at varying lower densities and incubated. Plates were stained and counted for clonogenic survival assays.

The effects of ascorbic acid (AA) in combination with a pentaaza macrocyclic ring complex (GC4419) was tested in a clonogenic cell survival assay to determine the effects of the combination alone and when paired with ionizing radiation. Human tongue carcinoma cells (Cal27) were exponentially grown in culture for 48 hours. The cells were then treated with 5 μM GC4419 for 3 hours and 10 pmol/cell ascorbate for 1 hour, either alone, in combination (GC+AA), and/or paired with a dose of ionizing radiation (2 Gy). After the ionizing radiation dose, the cells were trypsinized, counted, replated at varying lower densities and incubated. Plates were stained and counted for clonogenic survival assays. The results are shown in FIG. 6. The results show that treatment with ascorbate in combination with GC4419 resulted in significant enhancements in cell killing, as compared to a control, and as compared to either GC4419 or ascorbate alone. These unexpectedly good results achieved with the combination of GC4419 and ascorbate appear to demonstrate a level of synergistic activity between the two compounds, as the enhancement appears to be more than merely an additive effect. Furthermore, treatment with ascorbate in combination with GC4419 sensitized the cancer cells to radiation, thereby increasing the efficiency of the ionizing radiation in cell killing (GC+AA+IR) as compared to administration of ionizing radiation alone (IR 2Gy). Accordingly, the results show that ascorbate in combination with GC4419 significantly increases the efficacy of ionizing radiation.

Example 7

Figure 7:
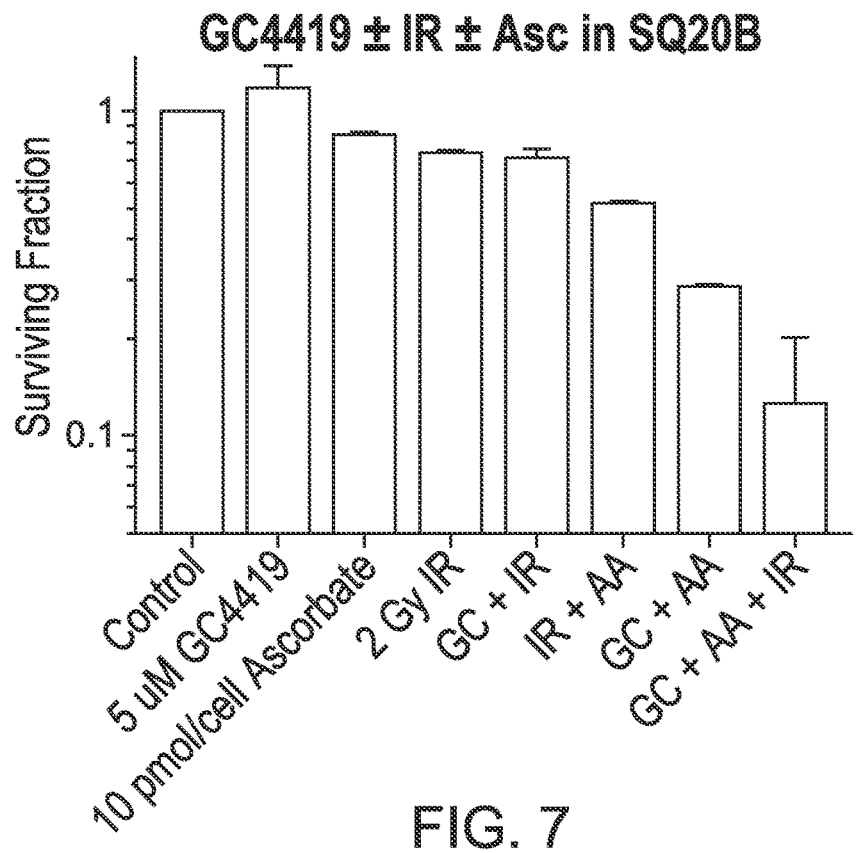
FIG. 7 is a graph showing the surviving fraction of SQ20B cells treated with ascorbate and combinations including ascorbate. The effects of ascorbate in combination with a pentaaza macrocyclic ring complex (GC4419) was tested in a clonogenic cell survival assay to determine the effects of the combination alone and when paired with ionizing radiation. Human head and neck squamous cell carcinoma cells (SQ20B) were plated and grown in culture for 48 hours. The cells were then treated with 5 µM GC4419 for 24 hours and 10 pmol/cell ascorbate (AA) for 1 hour, either alone, in combination (GC+AA), and/or paired with a dose of ionizing radiation (2 Gy). After the ionizing radiation dose, the cells were trypsinized, counted, replated at varying lower densities and incubated. Plates were stained and counted for clonogenic survival assays.

The effects of ascorbate in combination with a pentaaza macrocyclic ring complex (GC4419) was tested in a clonogenic cell survival assay to determine the effects of the combination alone and when paired with ionizing radiation. Human head and neck squamous cell carcinoma cells (SQ20B) were plated and grown in culture for 48 hours. The cells were then treated with 5 μM GC4419 for 24 hours and 10 pmol/cell ascorbate (AA) for 1 hour, either alone, in combination (GC+AA), and/or paired with a dose of ionizing radiation (2 Gy). After the ionizing radiation dose, the cells were trypsinized, counted, replated at varying lower densities and incubated. Plates were stained and counted for clonogenic survival assays. The results are shown in FIG. 7. The results show that treatment with ascorbate in combination with GC4419 resulted in significant enhancements in cell killing, as compared to a control, and as compared to GC4419 and ascorbate alone. These unexpectedly good results achieved with the combination of GC4419 and ascorbate appear to demonstrate a level of synergistic activity between the two compounds, as the enhancement appears to be more than merely an additive effect. Furthermore, treatment with ascorbate in combination with GC4419 sensitized the cancer cells to radiation, thereby increasing the efficiency of the ionizing radiation in cell killing (GC+AA+ IR) as compared to administration of ionizing radiation alone (IR 2Gy). Accordingly, the results show that ascorbate in combination with GC4419 significantly increases the efficacy of ionizing radiation.

Example 8

Figure 8:
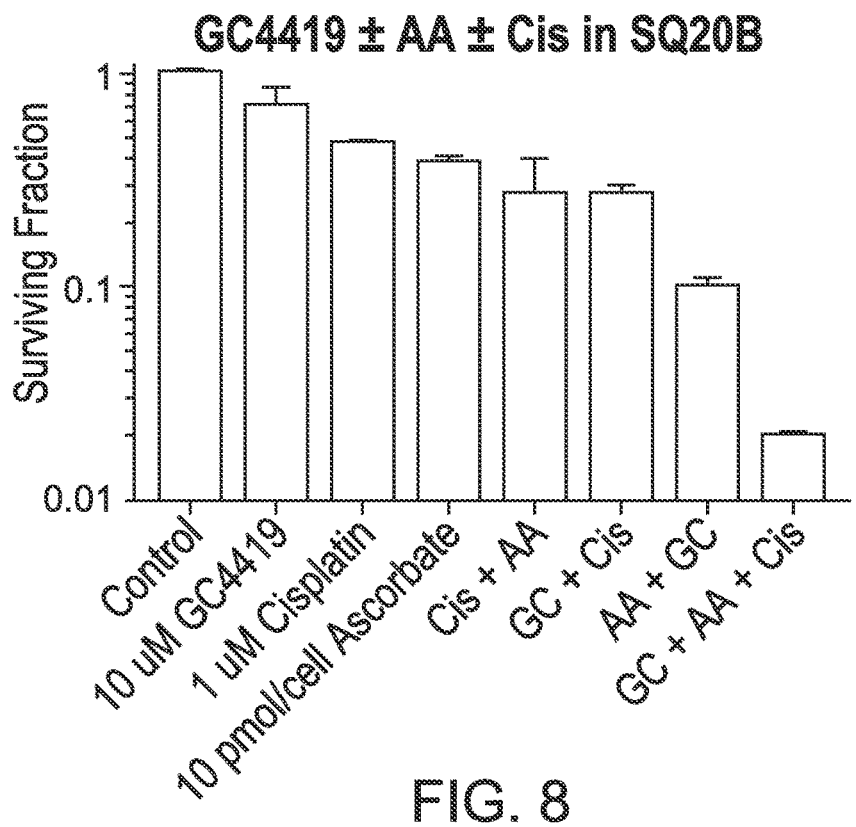
FIG. 8 is a graph showing the surviving fraction of SQ20B cells treated with ascorbate and combinations including ascorbate. The effects of ascorbate in combination with a pentaaza macrocyclic ring complex (GC4419) was tested in a clonogenic cell survival assay to determine the effects of the combination alone and when paired with the chemotherapeutic agent cisplatin. Human head and neck squamous cell carcinoma cells (SQ20B) were plated and grown in culture for 48 hours. The cells were then treated with cisplatin for 6 hours, 10 µM GC4419 for 3 hours, and 10 pmol/cell ascorbate (AA) for 1 hour. The cells were then trypsinized, counted, replated at varying lower densities and incubated. Plates were stained and counted for clonogenic survival assays.

The effects of ascorbate in combination with a pentaaza macrocyclic ring complex (GC4419) was tested in a clonogenic cell survival assay to determine the effects of the combination alone and when paired with the chemotherapeutic agent cisplatin. Human head and neck squamous cell carcinoma cells (SQ20B) were plated and grown in culture for 48 hours. The cells were then treated with cisplatin for 6 hours, 10 μM GC4419 for 3 hours, and 10 pmol/cell ascorbate (AA) for 1 hour. The cells were then trypsinized, counted, replated at varying lower densities and incubated. Plates were stained and counted for clonogenic survival assays. The results are shown in FIG. 8. The results show that treatment with ascorbate and GC4419 in combination with cisplatin resulted in significant enhancements in cell killing, as compared to a control, and to any of cisplatin, GC4419 or ascorbate monotherapies.

Example 9

Figure 9:
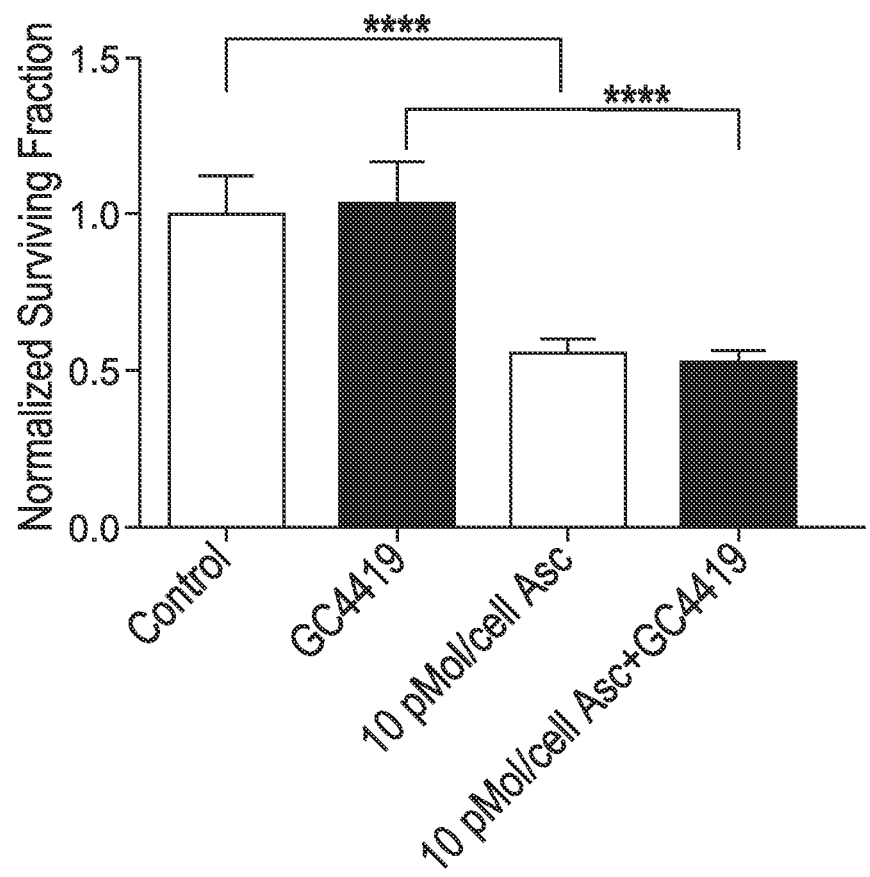
FIG. 9 is a graph showing the normalized surviving fraction of normal human fiborplasts (NHFs) treated with GC4419, ascorbate, and a combination of GC4419 and ascorbate. Normal human fibroblasts (NHFs) were plated and grown in culture (low FBS media) for 48 hours. The NHFs were then treated with 5 µM GC4419 for 24 hours followed by treatment with 10 pmol/cell ascorbate for 1 hour.

Normal human fibroblasts (NHFs) were plated and grown in culture (low FBS media) for 48 hours. The NHFs were then treated with 5 μM GC4419 for 24 hours followed by treatment with 10 pmol/cell ascorbate for 1 hour. The results are shown in FIG. 9 below. The results show that GC4419 does not increase cytotoxicity of ascorbate to NHFs.

Example 10

Figure 10:
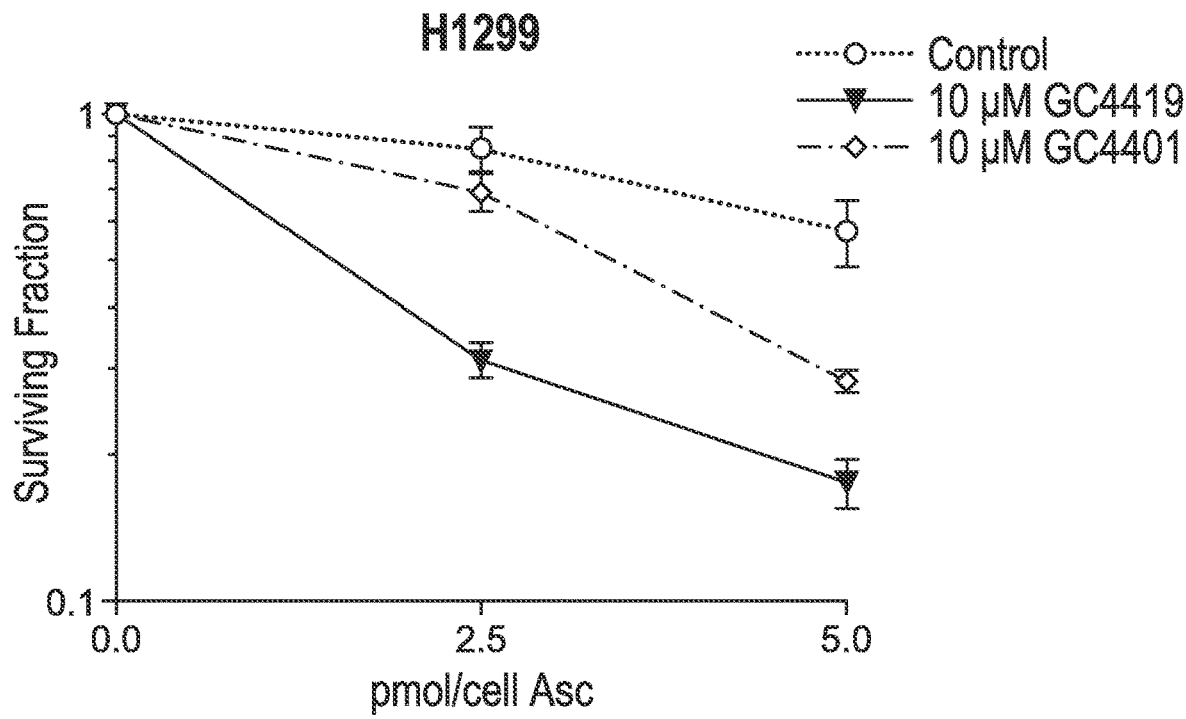
FIG. 10 is a plot showing the surviving fraction of H1299 cells for increasing amounts of ascorbate, as determined by a clonogenic cell survival assay used to determine the effects of the compound alone and in combination with either the pentaaza macrocyclic ring complex (GC4419) or the pentaaza macrocyclic ring complex (GC4401). Non-small cell lung cancer cells (H1299) were exponentially grown in culture for 48 hours. The cells were then treated with ascorbate (Asc) at the concentrations shown for one hour and either 10 µM GC4419 or 10 µM GC4401 for 24 hours. After 24 hours, the cells were trypsinized, counted, replated at varying lower densities and incubated. Plates were stained and counted for clonogenic survival assays.

The effect of ascorbate was tested in a clonogenic cell survivial assay to determine the effects of the compound alone and in combination with the pentaaza macrocyclic ring complex (GC4419) and the pentaaza macrocyclic ring complex (GC4401). Non-small cell lung cancer cells (H1299) were exponentially grown in culture for 48 hours. The cells were then treated with either 10 μM GC4419 or 10 μM GC4401 for 24 hours, and ascorbate (Asc) for one hour, at the concentrations shown, and followed immediately by clonogenic assay. The cells were trypsinized, counted, replated at varying lower densities and incubated. Plates were stained and counted for clonogenic survival assays. The results are shown in FIG. 10. The results show that treatment with ascorbate in combination with 10 μM GC4419 or 10 μM GC4401 resulted in significant enhancements in cell killing, as compared to control.

Example 11

Figure 11:
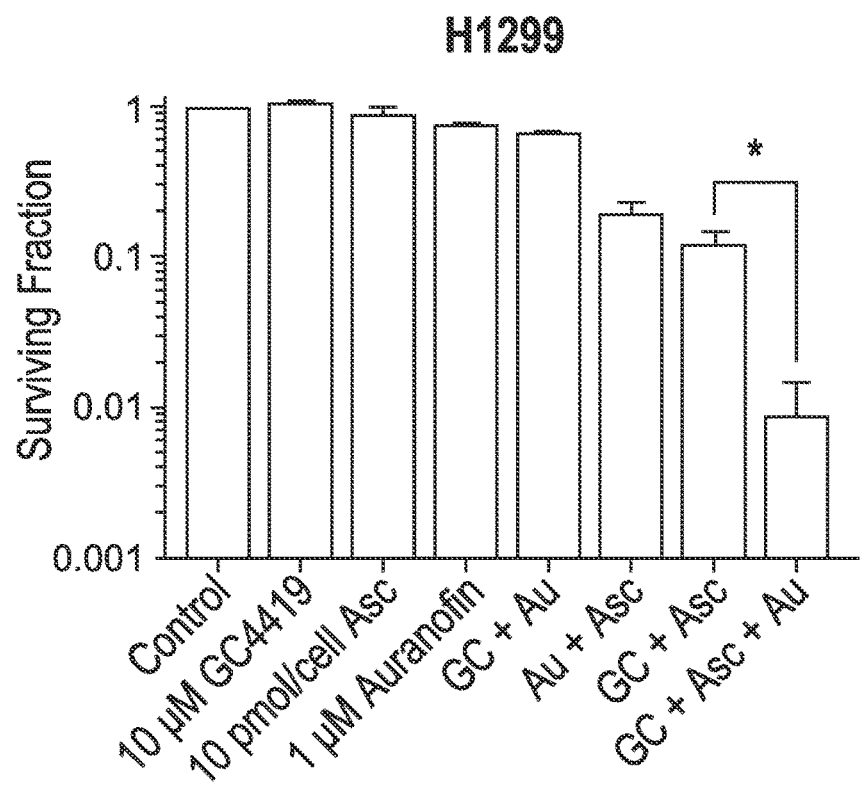
FIG. 11 is a graph showing the surviving fraction of H1299 cells treated with ascorbate and combinations including ascorbate and/or auranofin. The effects of ascorbate in combination with a pentaaza macrocyclic ring complex (GC4419) was tested in a clonogenic cell survival assay to determine the effects of the combination alone and when paired with the auranofin. Non-small cell lung cancer cells (H1299) were plated and grown in culture for 48 hours. The cells were then treated with 1 µM auranofin for 24 hours, 10 µM GC4419 for 24 hours, and 10 pmol/cell ascorbate (AA) for 1 hour. The cells were then trypsinized, counted, replated at varying lower densities and incubated. Plates were stained and counted for clonogenic survival assays.

The effects of ascorbate in combination with a pentaaza macrocyclic ring complex (GC4419) was tested in a clonogenic cell survival assay to determine the effects of the combination alone and when paired with the thioredoxin reductase inhibitor auranofin. Non-small cell lung cancer cells (H1299) were plated and grown in culture for 48 hours. The cells were then treated with 1 μM auranofin for 24 hours, 10 μM GC4419 for 24 hours, and 10 pmol/cell ascorbate (AA) for 1 hour. The cells were then trypsinized, counted, replated at varying lower densities and incubated. Plates were stained and counted for clonogenic survival assays. The results are shown in FIG. 11. The results show that treatment with ascorbate and GC4419 in combination with ascorbate resulted in significant enhancements in cell killing, as compared to a control, and to any of GC4419 or ascorbate monotherapies. The results further show that treatment with ascorbate and GC4419 in combination with auranofin also resulted in significant enhancements in cell killing, as compared to a control, and to any of GC4419, auranofin or ascorbate monotherapies, or pairwise combinations including that of GC4419 and ascorbate.

What is claimed is:

1. A method of treating a cancer selected from the group consisting of glioblastoma, glioma, sarcoma, head and neck cancer, pancreatic cancer, and non-small cell lung cancer, in a mammalian subject afflicted therewith, the method comprising:
administering to the subject an active agent selected from the group consisting of ascorbic acid, an ascorbic acid derivative, and/or a pharmaceutically acceptable salt thereof;
administering to the subject a cancer therapy comprising at least one of radiation therapy and chemotherapy; and
administering to the subject a pentaaza macrocyclic ring complex corresponding to formula (I) below:

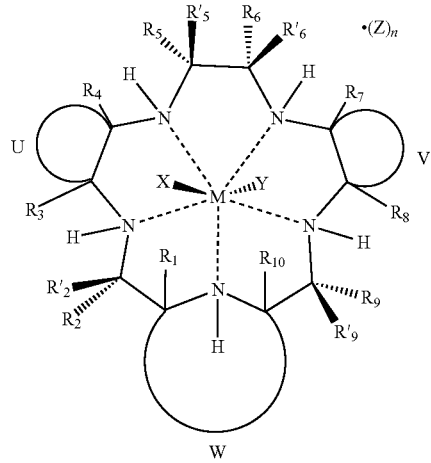

wherein
M is $Mn^{2+}$ or $Mn^{3+}$;
$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently hydrogen, hydrocarbyl, substituted hydrocarbyl, heterocyclyl, an amino acid side chain moiety, or a moiety selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, and $-OP(O)(OR_{11})(OR_{12})$, wherein $R_{11}$ and $R_{12}$ are independently hydrogen or alkyl;
U, together with the adjacent carbon atoms of the macrocycle, forms a fused substituted or unsubstituted, saturated, partially saturated or unsaturated, cycle or heterocycle having 3 to 20 ring carbon atoms;
V, together with the adjacent carbon atoms of the macrocycle, forms a fused substituted or unsubstituted, saturated, partially saturated or unsaturated, cycle or heterocycle having 3 to 20 ring carbon atoms;
W, together with the nitrogen of the macrocycle and the carbon atoms of the macrocycle to which it is attached, forms an aromatic or alicyclic, substituted or unsubstituted, saturated, partially saturated or unsaturated nitrogen-containing fused heterocycle having 2 to 20 ring carbon atoms, provided that when W is a fused aromatic heterocycle the hydrogen attached to the nitrogen which is both part of the heterocycle and the macrocycle and $R_1$ and $R_{10}$ attached to the carbon atoms which are both part of the heterocycle and the macrocycle are absent;
X and Y represent suitable ligands which are derived from any monodentate or polydentate coordinating ligand or ligand system or the corresponding anion thereof;
Z is a counterion;
n is an integer from 0 to 3; and
the dashed lines represent coordinating bonds between the nitrogen atoms of the macrocycle and the transition metal, manganese.

2. The method in accordance with claim 1, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

3. The method in accordance with claim 1, wherein W is an unsubstituted pyridine moiety.

4. The method in accordance with claim 1, wherein U and V are trans-cyclohexanyl fused rings.

5. The method in accordance with claim 1, wherein the pentaaza macrocyclic ring complex is a complex selected from the group consisting of the complexes of formula (2)-(7) below:

2
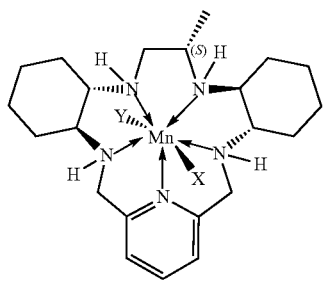

3
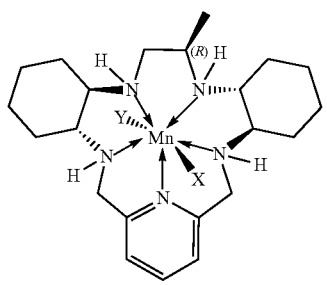

4
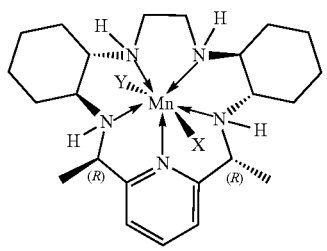

5
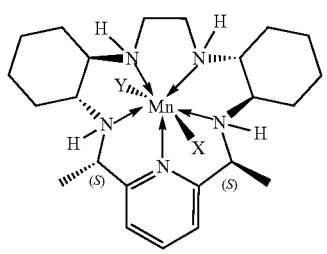

6
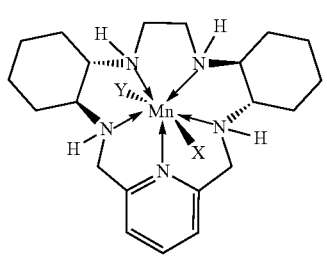

7
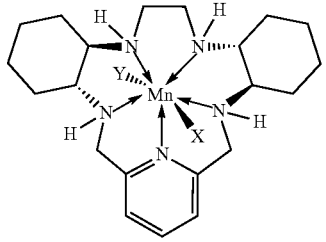

6. The method in accordance with claim 1, wherein X and Y, are independently selected from the group consisting of fluoro, chloro, bromo and iodo anions.

7. The method in accordance with claim 1, wherein X and Y correspond to —O—C(O)—$X_1$, where each $X_1$ is —C($X_2$)($X_3$)($X_4$), and each —C($X_2$)($X_3$)($X_4$) corresponds to any of combinations 1 to 9 appearing in the following table:

| Combination | $X_2$ | $X_3$ | $X_4$ |
|---|---|---|---|
| 1 | Ph | H | H |
| 2 | Ph | OH | H |
| 3 | Ph | $NH_2$ | H |
| 4 | Ph | =O ($X_3$ and $X_4$ in combination) | |
| 5 | Ph | $CH_3$ | H |
| 6 | $CH_3$ | H | H |
| 7 | $CH_3$ | OH | H |
| 8 | $CH_3$ | $NH_2$ | H |
| 9 | $CH_3$ | =O ($X_3$ and $X_4$ in combination) | |

8. The method in accordance with claim 1, wherein the pentaaza macrocyclic ring complex is at least one of the following:

(4403)
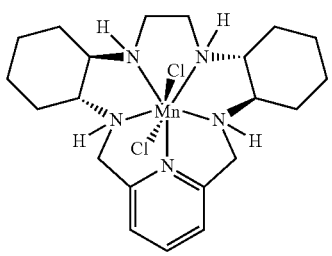

(4419)
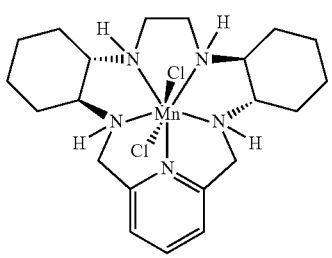

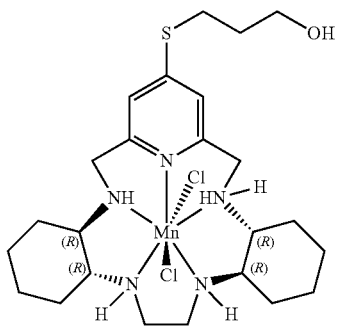
(4432)

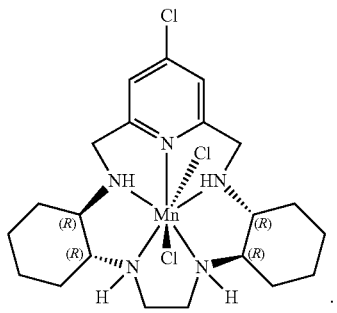
(4409)

9. The method in accordance with claim 1, wherein the active agent comprises an ascorbic acid derivative.

10. The method in accordance with claim 9, wherein the ascorbic acid derivative is an ascorbic acid ester selected from the group consisting of ascorbyl palmitate, ascorbyl acetate, ascorbyl propionate, ascorbyl stearate, ascorbyl laurate, ascorbyl myristate, and ascorbyl behenate.

11. The method in accordance with claim 9, wherein the ascorbic acid derivative is one or more of a phosphorylated form of ascorbic acid, a derivative of ascorbic acid having one or more substitutions at the 2, 3, 4, 5 and 6 carbons of ascorbic acid, an ascorbic acid derivative having a sulfur atom substituted at the C6 position of ascorbic acid that is conjugated to a triphenylphosphonium group via a linker moiety, a 4-benzoyl-3-hydroxyfuran-2-(5H)-one derivative of ascorbic acid, and a 4-acetyl-5-aryl-3,4-dihydro-furan-2 (5H)-one derivatives of ascorbic acid.

12. The method in accordance with claim 1, wherein the active agent is a pharmaceutically acceptable salt of ascorbic acid or an ascorbic acid derivative.

13. The method in accordance with claim 12, wherein the pharmaceutically acceptable salt is selected from the group consisting of sodium ascorbate, magnesium ascorbate, calcium ascorbate and potassium ascorbate.

14. The method in accordance with claim 1, wherein the active agent selected from the group consisting of ascorbic acid, an ascorbic acid derivative, and/or a pharmaceutically acceptable salt thereof, is administered in a ratio of the active agent to the pentaaza macrocyclic ring complex of at least 20:1.

15. The method in accordance with claim 1, wherein the active agent selected from the group consisting of ascorbic acid, an ascorbic acid derivative, and/or a pharmaceutically acceptable salt thereof, is administered in an amount sufficient to provide a peak plasma concentration of at least 1 mM.

16. The method in accordance with claim 1, wherein the active agent selected from the group consisting of ascorbic acid, an ascorbic acid derivative, and/or a pharmaceutically acceptable salt thereof, is administered in a dosage amount of at least 100 mg/kg body weight.

17. The method in accordance claim 1, wherein the mammal is a human patient.

18. The method in accordance with claim 1, wherein the active agent is administered substantially simultaneously with the pentaaza macrocyclic ring complex.

19. The method in accordance with claim 1, wherein the active agent is administered before the pentaaza macrocyclic ring complex.

20. The method in accordance with claim 1, wherein the active agent is administered after the pentaaza macrocyclic ring complex.

21. The method in accordance with claim 1, wherein the active agent and pentaaza macrocyclic ring complex are administered within 24 hours of each other.

22. The method in accordance with claim 1, wherein the active agent and pentaaza macrocyclic ring complex are administered within 1 hour of each other.

23. The method in accordance with claim 1, wherein the active agent and pentaaza macrocyclic ring complex are administered by an administration route selected from the group consisting of oral, parenteral, intravenous, intraarterial, subcutaneous, rectal, subcutaneous, intramuscular, intraorbital, intracapsular, intraspinal, intraperitoneal, intrasternal, topical, nasal, transdermal, intraocular, intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

24. The method in accordance with claim 1, wherein the active agent and pentaaza macrocyclic ring complex are administered prior to the cancer therapy.

25. The method in accordance with claim 1, wherein the active agent and pentaaza macrocyclic ring complex are administered within 24 hours of the cancer therapy.

26. The method in accordance with claim 1, wherein the active agent and pentaaza macrocyclic ring complex are administered within 1 hour of the cancer therapy.

27. The method in accordance with claim 1, wherein at least one of the active agent and pentaaza macrocyclic ring complex are administered after the cancer therapy.

28. The method in accordance with claim 1, wherein the cancer therapy comprises the administration of a series of multiple doses of radiation, and wherein the active agent and pentaaza macrocyclic ring complex are administered before one or more radiation dose in the series.

29. The method in accordance with claim 1, wherein the cancer therapy comprises administration of a chemotherapy dose comprising a chemotherapeutic agent selected from the group consisting of alkylating antineoplastic agents, nitrogen mustards, nitrosoureas, tetrazines, aziridines, platinum-based antineoplastic agents, anti-metabolites, fluoropyrimidines, anthracyclines, deoxynucleoside analogs, thiopurines, anti microtubule agents, taxanes, topoisomerase inhibitors, antitumor antibiotics, antimetabolite anti-cancer agents and antimitotic anti-cancer agents.

30. The method in accordance with claim 29, wherein the cancer therapy comprises administration of a chemotherapy dose comprising a chemotherapeutic agent selected from the group consisting of all-trans retinoic acid, arsenic trioxide, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, and vinorelbine.

31. The method in accordance with claim 29, wherein the cancer therapy comprises administration of a chemotherapy dose comprising at least one of a platinum-based antineoplastic agent, a taxane, an anthracycline and/or an antitumor antibiotic.

32. The method in accordance with claim 31, wherein the cancer therapy comprises administration of a chemotherapy dose comprising a chemotherapeutic agent selected from the group consisting of cisplatin, doxorubicin, bleomycin, and paclitaxel.

* * * * *